United States Patent
Nemoto

(10) Patent No.: US 6,403,818 B1
(45) Date of Patent: Jun. 11, 2002

(54) PROCESS FOR PRODUCING α-HYDROXY-CARBONYL COMPOUND

(75) Inventor: Hisao Nemoto, Tokushima (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/794,140

(22) Filed: Feb. 28, 2001

Related U.S. Application Data

(60) Provisional application No. 60/185,399, filed on Feb. 28, 2000.

(51) Int. Cl.[7] .................................................. C07F 7/10
(52) U.S. Cl. ...................... 556/419; 556/417; 556/463; 556/466; 556/470; 558/414; 544/64; 549/210
(58) Field of Search ................ 556/419, 463, 556/466, 470, 417; 558/414; 544/64; 549/210

(56) References Cited

U.S. PATENT DOCUMENTS

| | | | |
|---|---|---|---|
| 4,430,503 A | * | 2/1984 | Findeisen .................. 556/417 |
| 5,332,825 A | * | 7/1994 | Buckland .................. 556/417 |
| 5,334,610 A | | 8/1994 | Draber et al. |

FOREIGN PATENT DOCUMENTS

| | | |
|---|---|---|
| DE | 3643461 A1 | 6/1988 |
| EP | 0498680 A1 | 8/1992 |
| EP | 0552631 A1 | 7/1993 |
| EP | 0823423 A1 | 2/1998 |
| EP | 0900566 A1 | 3/1999 |
| JP | 08259558 A | 10/1996 |
| JP | 10182601 A | 7/1998 |
| WO | 9505386 A1 | 2/1995 |
| WO | 9511244 A1 | 4/1995 |
| WO | 9632110 A1 | 10/1996 |
| WO | 9721725 A1 | 6/1997 |
| WO | 9729077 A1 | 8/1997 |
| WO | 9805641 A1 | 2/1998 |
| WO | 9857932 A1 | 12/1998 |
| WO | 9905104 A1 | 2/1999 |

OTHER PUBLICATIONS

Ma et al, 199th Annual meeting of the Pharmaceutical society of Japan, Mar. 29, 1999.*

J.J. Chen et al., Bioorganic & Medicinal Chemistry Letters, (1996), 6, pp. 435–438.

H.H. Wasserman et al., Tetrahedron Lett., (1990), 40, pp. 6163–6166.

H. Bienayme, Tetrahedron Lett., (1998), 39, pp. 4255–4258.

Cheng–He Zhou et al., Synthetic Commun., (1994), 24, pp. 43–46.

Robert W. Armstrong et al., Acc. Chem. Res., (1996), 29, pp. 123–131.

M. Hagihara et al., J. Am. Chem. Soc., (1992), 114, pp. 6570–6571.

Bruce E. Maryanoff et al., J. Am. Chem. Soc., (1995), 117, pp. 1225–1239.

Tsuyoshi Satoh et al., J. Org. Chem., (1991), 56, pp. 4129–4134.

Alessandro Dondoni et al., Synthesis, (1995), pp. 181–186.

* cited by examiner

*Primary Examiner*—Shailendra Kumar
(74) *Attorney, Agent, or Firm*—Birch, Stewart, Kolasch & Birch, LLP

(57) ABSTRACT

The invention provides a process for producing an α-hydroxy-carbonyl compound or an α-protected hydroxy-carbonyl compound by reacting a carbonyl compound (I) with a compound (II) and a compound (III). The compounds (I), (II) and (III) are defined below.

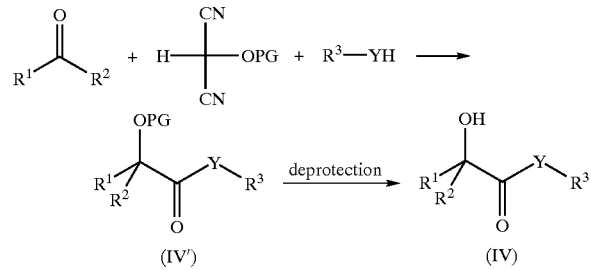

$R^1$, $R^2$, $R^3$ and $R^4$ are an organic group. PG is a protective group for hydroxy group. Y is $R^4N$, S or O. The product is useful in pharmacology.

10 Claims, No Drawings

PROCESS FOR PRODUCING α-HYDROXY-CARBONYL COMPOUND

This application claims priority on provisional Application No. 60/185,399 filed on Feb. 28, 2000, the entire contents of which are hereby incorporated by reference.

BACKGROUNDS OF INVENTION

The invention relates to a process for producing an α-hydroxy-carbonyl compound or an (α-protected hydroxy-carbonyl compound. From three starting compounds by one stepped reaction. The obtained compounds are useful to derive pharmacologically useful compounds. In the process of the invention, an α-hydroxycarbonyl compound, for example an α-hydroxyamide and an α-hydroxyester can be simply obtained. In the process, the amide moiety can be introduced from the corresponding amine moiety and the ester, from the corresponding alcohol.

The α-hydroxycarbonyl compound is observed in many physiological activity. For example, EP-A 900566 published on Mar. 10, 1999, JP-A 98-182601 published on Jul. 07, 1998 and EP-A 498680 published on Aug. 12, 1992 disclose an HIV-1 Protease Inhibitor. WO 98/57932 published on Dec. 23, 1998 and WO 96/32110 published on Oct. 17, 1996 disclose an anticoagulant (thrombin inhibitor). WO 99/05104 published on Feb. 4, 1999 discloses a cyclooxygenase-2 Inhibitor. EP-A 823423 published on Feb. 11, 1998 discloses a muscarinic M Antagonist. WO 98/05641 published on Feb. 12, 1998 discloses a bronchodilator. WO 97/29077 published on Aug. 14, 1997 discloses an antineoplastic. WO 97/21725 published on Jun. 19, 1997 discloses a gpIIb/IIIa Receptor Antagonist. JP-A 96-259558 published on Oct. 8, 1998 and EP-A 552631 published on Jul. 28, 1993 discloses an antidiabetic. WO 95/11244 published on Apr. 27, 1995 discloses an NMDA Receptor Antagonist. WO 95/05386 published on Feb. 23, 1995 discloses a phosphodiesterase IV Inhibitor.

It is evident that there are many physiologically active compounds having the α-hydroxycarbonyl in the structure. This is the reason efficient synthesis of the α-hydroxycarbonyl will be useful to production of a physiologically active compound such as medicines. It will be useful in particular to production of a statine compound.

PRIOR ARTS

In general, the α-hydroxycarbonyl compound, especially an α-hydroxyester and an α-hydroxyamide including many physiologically active compounds, can be obtained by synthesizing the corresponding α-hydroxycarboxylic acid and esterifying or amidating it. The key intermediate compound, the α-hydroxycarboxylic acid, is synthesizd at two stages, a reaction of a nucleophilic agent principally to an aldehyde or ketone and conversion of the residue of the nucleophilic agent to a carbonyl group. Typical examples thereof include production of cyanohydrin by adding cyano to carbonyl and then acid hydrolysis (for example J. J. Chen et al., Bioorg. Med. Chem. Lett., 1996, 6, 435–438, B. E. Maryanoff et al. and J. Am. Chem. Soc., 1995, 117, 1225–1239), addition of an alkenyl anion or an equivalent thereto to a carbonyl compound and then an oxidative cleavage (H. H. Wasserman et al., Tetrahedron Lett., 1990, 40, 6163–6166 and T. Satoh et al. J. Org. Chem., 1991, 56, 4129–4134), addition of an orthoester anion to a carbonyl compound and then acid hydrolysis (M. Hagihara et al., J. Am. Chem. Soc., 1992, 114, 6570–6571), and addition to 2-thiazolygroup to a carbonyl compound and then hydrolysis (A. Dondoni et al., Synthesis, 1995, 181–186).

In order to be converted to α-hydroxyamide and α-hydroxyester, condensaton of the produced carbonyl group with an amine or alcohol will be necessary. Among α-hydroxycarbonyl compounds, α-hydroxyamide and α-hydroxyester were conventionally obtained at three stages of reaction. It is known in FRG Patent 1988, 3643461 (DE-3643461), 88-183834 to produce an α-hydroxyester by addition of methyl isoccyanide to a carbonyl compound in the presence of titanium tetrachloride and in C—H. Zhou et al. Synthetic Commun., 1994, 24, 43–46 to produce α-hydroxyacid by reacting an aromatic aldehyde with chloroform in the presence of α-cyclodextrinand triethylbenzylammonium chloride.

Those arts are involved in problems that reaction conditions are severe, agents are limited and conversion is impossible directly to α-hydroxyamide.

Then Passerini Reaction can produce α-acyloxyamide at a single stage. It is disclosed in I. Ugi et al. Comprehensive Organic Synthesis; Pergamon, N.Y., Vol. 2, pp 1083–1109 and H. Bienayme Tetrahedron Lett., 1998, 39, 4255–4258. Passerini Reaction, however, limits the nucleophilic agent to isocyanide and produces many products with a low yield, this way having a difficulty in application. A few of isocyanides are availale in the commercial market and therefore many isocyanides have to be synthesized to obtain necessary amides.

An example of multi-component reaction, that is, one pot reaction, supporting usefulness of the invention, is disclosed in R. B. Armstrong et al. Acc. Chem. Res., 1996, 29, 123–131.

DISCLOSURE OF INVENTION

The invention provides a process for producing an α-hydroxy-carbonyl compound or an α-protected hydroxy-carbonyl compound by reacting a carbonyl compound (I) with a compound (II) and a compound (III). The compounds (I), (II) and (III) are defined below.

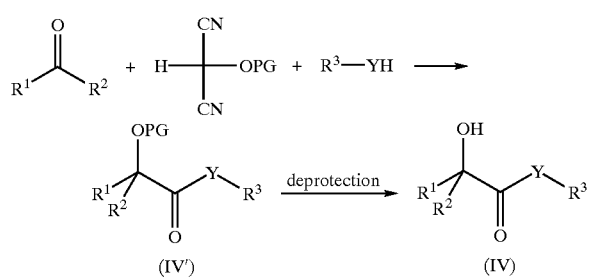

$R^1$, $R^2$, $R^3$ and $R^4$ are an organic group, being different from or the same as one another. They, in particular $R^1$ and $R^2$, may be any organic group that will not disturb the reaction. They may be protected by a protective group or have at least one substituent.

PG is a protective group for hydroxy group. Y is $R^4N$, S or O.

$R^1$, $R^2$, $R^3$ and $R^4$ may have at least one substituent such as an aliphatic group, an alicyclic group or an aromatic hydrocarbon group which may have at least one substituent. $R^1$, $R^2$, $R^3$ and $R^4$ may have at least one substituent, for example, that shown by $Z^1$, $Z^2$ or $Z^3$. $Z^1$, $Z^2$ and $Z^3$ are defined below and are different from or the same as one another.

In the above shown reaction, an aldehyde or ketone compound (I), an amine or alcohol compound (II) and a compound of H-MAC-TBS (III) may be reacted with one another in one pot. The reaction may be conducted in the presence of a base, which is useful when the amine compound (II) is weakly basic. Then it may be conducted with an agent to eliminate a hydrogen cation of the compound (III) or an agent to activate the compound (III). Then the reaction may be effected with the compound (III) activated.

The protective group may include TBDMS, TMS, TBDPS, an acyl group such as acetate, an organic metal or heteroatom group such as $R^2B$, $R^3Ge$ and $R^3Sn$, which can be connected with oxygen atom and then phosphoric acid or sulfonic acid.

The organic group for $R^1$, $R^2$, $R^3$ and $R^4$ may include typically an alkyl such as methyl, ethyl, propyl and butyl, an alkenyl such as ethylene and propylene, an alkynyl such as ethynyl and an aryl such as phenyl.

The reaction of the invention can produce an α-hydroxycarbonyl compound, including statine compounds such as cyclohexylnorstatine and statines having the following formulae. These are useful as HIV inhibitor.

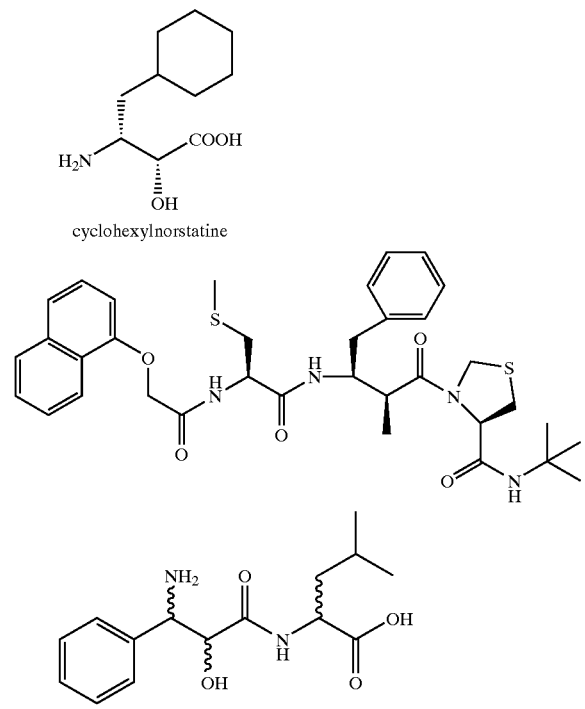

cyclohexylnorstatine

The organic group is not limited, as far as it does not disturb the invention, and for example includes: hydrogen atom, hydroxy group, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, ahalogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5-12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{6-12}$ arylamino group, di($C_{6-12}$ aryl)amino group, a $C_{1-8}$ alkyl ($C_{6-12}$ aryl)amino group, a 5 to 12-membered heteroarylamino group, di(5 to 12-membered heteroaryl)amino group, a $C_{1-8}$ alkyl(5 to 12-membered heteroaryl)amino group, an amino $C_{1-8}$ alkyl group, a $C_{1-8}$ alkylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl) amino $C_{2-8}$ alkenyl group, a 5 to 12-membered heteroarylamino $C_{2-8}$ alkenyl group, di(5 to 12-membered heteroaryl) amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl) amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group.

The substituents $Z^1$, $Z^2$ and $Z^3$, which may be respectively protected if necessary, for example include: hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-8}$ acyloxy group, a $C_{1-12}$ acyl $C_{1-8}$ alkyl group, carbamoyl group, a N-$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl) amino group, a 5 to 12-membered heteroarylamino group, di(5 to 12-membered heteroaryl)amino group, a $C_{1-8}$ alkyl(5 to 12-membered heteroaryl)amino group, a $C_{1-8}$ alkyl group, a $C_{3-8}$ cycloalkyl group, a $C_{4-8}$ bicycloalkyl group, a $C_{1-8}$ alkyl $C_{3-8}$ cyclo alkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkylthio group, a $C_{1-8}$ alkyl sulfonyl $C_{1-8}$ alkyl group, a $C_{1-8}$ alkylsulfinyl $C_{1-8}$ alkyl group, ahalogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryll group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group., a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{1-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, a $C_{1-8}$ alkoxy group, a $C_{3-8}$ cycloalkoxy group, a $C_{4-8}$ bicycloalkoxy group, a $C_{1-8}$ alkyl $C_{3-8}$ cycloalkoxy group, a $C_{1-8}$ alkoxy $C_{1-8}$ alkoxy group, a hydroxy $C_{1-8}$ alkoxy group, a mercapto $C_{1-8}$ alkoxy group, a $C_{1-8}$ alkylthio $C_{1-8}$ alkoxy group, a $C_{1-8}$ alkylsulfonyl $C_{1-8}$ alkoxy group, a $C_{1-8}$ alkylsulfinyl $C_{1-8}$ alkoxy group, a halogeno $C_{1-8}$ alkoxy group, a nitro $C_{1-8}$ alkoxy group, a cyano $C_{1-8}$ alkoxy group, a $C_{1-8}$ alkoxycarbonyl $C_{1-8}$ alkoxy group, a $C_{1-8}$ alkylthiocarbonyl $C_{1-8}$ alkoxy group, a $C_{2-9}$ alkanoyl $C_{1-8}$ alkoxy group, a $C_{2-9}$ alkanoyloxy $C_{1-8}$ alkoxy group, a $C_{2-8}$ alkenyloxy group, a $C_{3-8}$ cycloalkenyloxy group, a $C_{1-8}$ alkyl $C_{3-8}$ cycloalkenyloxy group, a $C_{1-8}$ alkoxy $C_{1-8}$ alkenyloxy group, a hydroxy $C_{1-8}$ alkenyloxy group, a mercapto $C_{1-8}$ alkenyloxy group, a $C_{1-8}$ alkylthio $C_{1-8}$ alkenyloxy group, a $C_{1-8}$ alkylsulfonyl $C_{1-8}$ alkenyloxy group, a $C_{1-8}$ alkylsulfinyl $C_{1-8}$ alkenyloxy group, a halogeno $C_{1-8}$ alkenyloxy group, a nitro $C_{1-8}$ alkenyloxy group, a cyano $C_{1-8}$ alkenyloxy group, a $C_{2-8}$ alkynyloxy group, a $C_{3-8}$ cycloalkynyloxy group, a $C_{1-8}$ alkyl $C_{3-8}$ cycloalkynyl oxy group, a $C_{1-8}$ alkoxy $C_{1-8}$ alkynyloxy group, a hydroxy $C_{1-8}$ alkynyloxy group, a mercapto $C_{1-8}$ alkynyloxy group, a $C_{1-8}$ alkylthio $C_{1-8}$ alkynyloxy group, a $C_{1-8}$ alkylsulfonyl $C_{1-8}$ alkynyloxy group, a $C_{1-8}$ alkylsulfinyl $C_{1-8}$ alkynyloxy group, a halogeno $C_{1-8}$ alkynyloxy group, a nitro $C_{1-8}$ alkynyloxy group, a cyano $C_{1-8}$ alkynyloxy group, a $C_{6-12}$ aryloxy group, a 5 to 12-membered heteroaryloxy group, a $C_{1-8}$ alkyl $C_{6-12}$ aryloxy group, a $C_{2-8}$ alkenyl $C_{6-12}$ aryloxy group, a $C_{2-8}$ alkynyl $C_{6-12}$ aryloxy group, a $C_{1-8}$ alkyl 5 to 12-membered heteroaryloxy group, a $C_{2-8}$ alkenyl 5 to 12-membered heteroaryloxy group, a $C_{5-12}$ alkynyl 5 to 12-membered heteroaryloxy group, a hydroxy $C_{6-12}$ aryloxy group, a mercapto $C_{6-12}$ aryloxy group, a $C_{1-8}$ alkylthio $C_{6-12}$ aryloxy group, a $C_{1-8}$ alkylsulfonyl $C_{6-12}$ aryloxy group, a $C_{1-8}$ alkylsulfinyl $C_{6-12}$ aryloxy group, a hydroxy 5 to 12-membered heteroaryloxy group, a mercapto 5 to 12-membered heteroaryloxy group, a $C_{1-8}$ alkylthio $C_{6-12}$ heteroaryloxy group, a $C_{1-8}$ alkylsulfonyl $C_{6-12}$ heteroaryloxy group, a $C_{1-8}$ alkylsulfinyl $C_{6-12}$ heteroaryloxy group, a halogeno $C_{6-12}$ aryloxy group, a nitro $C_{6-12}$ aryloxy group, a cyano $C_{6-12}$ aryloxy group, a halogeno 5 to 12-membered heteroaryloxy group, a nitro 5 to 12-membered heteroaryloxy group, a cyano 5 to 12-membered heteroaryloxy group, a $C_{6-12}$ aryl $C_{1-8}$ alkoxyl group, a $C_{6-12}$ aryl $C_{2-8}$ alkenyloxy group, a $C_{6-12}$ aryl $C_{2-8}$ alkynyloxy group, a 5 to 12-membered heteroaryl $C_{1-8}$ alkoxy group, a 5 to 12-membered heteroaryl $C_{2-8}$ alkenyloxy group, a 5 to 12-membered heteroaryl $C_{2-8}$ alkynyloxy group, a $C_{1-8}$ alkyl $C_{6-12}$ aryl $C_{1-8}$ alkoxyl group, a $C_{1-8}$ alkyl $C_{6-12}$ aryl $C_{2-8}$ alkenyloxy group, a $C_{1-8}$ alkyl $C_{6-12}$ aryl $C_{2-8}$ alkynyloxy group, a $C_{2-8}$ alkenyl $C_{6-12}$ aryl $C_{1-8}$ alkoxy group, a $C_{2-8}$ alkenyl $C_{6-12}$ aryl $C_{2-8}$ alkenyloxy group, a $C_{2-8}$ alkenyl $C_{6-12}$ aryl $C_{2-8}$ alkynyloxy group, a $C_{2-8}$ alkynyl $C_{6-12}$ aryl $C_{1-8}$ alkoxy group, a $C_{2-8}$ alkynyl $C_{6-12}$ aryl $C_{2-8}$ alkenyloxy group, a $C_{2-8}$ alkynyl $C_{6-12}$ aryl $C_{2-8}$ alkynyloxy group, a $C_{1-8}$ alkyl 5 to 12-membered heteroaryl $C_{1-8}$ alkoxy group, a $C_{1-8}$ alkyl 5 to 12-membered heteroaryl $C_{2-8}$ alkenyloxy group, a $C_{1-8}$ alkyl 5 to 12-membered heteroaryl $C_{2-8}$ alkynyloxy group, a $C_{2-8}$ alkenyl 5 to 12-membered heteroaryl $C_{1-8}$ alkoxy group, a $C_{2-8}$ alkenyl 5 to 12-membered heteroaryl $C_{2-8}$ alkenyloxy group, a $C_{2-8}$ alkenyl 5 to 12-membered heteroaryl $C_{2-8}$ alkynyloxy group, a $C_{2-8}$ alkynyl 5 to 12-membered heteroaryl $C_{1-8}$ alkoxy group, a $C_{2-8}$ alkynyl 5 to 12-membered heteroaryl $C_{2-8}$ alkenyloxy group, a $C_{2-8}$ alkynyl 5 to 12-membered heteroaryl $C_{2-8}$ alkynyloxy group, a $C_{1-8}$ alkylthio group, a $C_{1-8}$ alkylsulfonyl group, a $C_{1-8}$ alkylsulfinyl group, a $C_{3-8}$ cycloalkylthio group, a $C_{3-8}$ cycloalkylsulfonyl group, a $C_{3-8}$ cycloalkylsulfinyl group, a $C_{4-8}$ bicycloalkylthio group, a $C_{4-8}$ bicycloalkylsulfonyl group, a $C_{4-8}$ bicycloalkylsulfinyl group, a $C_{1-8}$ alkyl $C_{3-8}$ cycloalkylthio group, a $C_{1-8}$ alkyl $C_{3-8}$ cycloalkylsulfonyl group, a $C_{1-8}$ alkyl $C_{3-8}$ cycloalkylsulfinyl group, a $C_{1-8}$ alkoxy $C_{1-8}$ alkylthio group, a $C_{1-8}$ alkoxy $C_{1-8}$ alkylsulfonyl group, a $C_{1-8}$ alkoxy $C_{1-8}$ alkylsulfinyl group, a hydroxy $C_{1-8}$ alkylthio group, a hydroxy $C_{1-8}$ alkylsulfonyl group, a hydroxy $C_{1-8}$ alkylsulfinyl group, a mercapto $C_{1-8}$ alkylthio group, a mercapto $C_{1-8}$ alkylsulfonyl group, a mercapto $C_{1-8}$ alkylsulfinyl group, a halogeno $C_{1-8}$ alkylthio group, a halogeno $C_{1-8}$ alkylsulfonyl group, a halogeno $C_{1-8}$ alkylsulfinyl group, a nitro $C_{1-8}$ alkylthio group, a nitro $C_{1-8}$ akylsulfonyl group, a nitro $C_{1-8}$ alkylsulfinyl group, a cyano $C_{1-8}$ alkylthio group, a cyano $C_{1-8}$ alkylsulfonyl group, a cyano $C_{1-8}$ alkylsulfinyl group, a $C_{1-8}$ alkoxycarbonyl $C_{1-8}$ alkylthio group, a $C_{1-8}$ alkoxycarbonyl $C_{1-8}$ alkylsulfonyl group, a $C_{1-8}$ alkoxycarbonyl $C_{1-8}$ alkylsulfinyl group, a $C_{1-8}$ alkylthiocarbonyl $C_{1-8}$ alkylthio group, a $C_{1-8}$ alkylthiocarbonyl $C_{1-8}$ alkylsulfonyl group, a $C_{1-8}$ alkylthiocarbonyl $C_{1-8}$ alkylsulfinyl group, a $C_{2-9}$ alkanoyl $C_{1-8}$ alkylthio group, a $C_{2-9}$ alkanoyl $C_{1-8}$ alkylsulfonyl group, a $C_{2-9}$ alkanoyl $C_{1-8}$ alkylsulfinyl group, a $C_{2-9}$ alkanoyloxy $C_{1-8}$ alkylthio group, a $C_{2-9}$ alkanoyloxy $C_{1-8}$ alkylsulfonyl group, a $C_{2-9}$ alkanoyloxy $C_{1-8}$ alkylsulfinyl group, a $C_{2-8}$ alkenylthio group, a $C_{2-8}$ alkenylsulfonyl group, a $C_{2-8}$ alkenylsulfinyl group, a $C_{3-8}$ cycloalkenylthio group, a $C_{3-8}$ cycloalkenylsulfonyl group, a $C_{3-8}$ cycloalkenylsulfinyl group, a $C_{1-8}$ alkyl $C_{3-8}$ cycloalkenylthio group, a $C_{1-8}$ alkyl $C_{3-8}$ cycloalkenylsulfonyl group, a $C_{1-8}$ alkyl $C_{3-8}$ cycloalkenylsulfinyl group, a $C_{1-8}$ alkoxy $C_{1-8}$ alkenylthio group, a $C_{1-8}$ alkoxy $C_{1-8}$ alkenylsulfonyl group, a $C_{1-8}$ alkoxy $C_{1-8}$ alkenylsulfinyl group, a hydroxy $C_{1-8}$ alkenylthio group, a hydroxy $C_{1-8}$ alkenylsulfonyl group, a hydroxy $C_{1-8}$ alkenylsulfinyl group, a mercapto $C_{1-8}$ alkenylthio group, a mercapto $C_{1-8}$ alkenylsulfonyl group, a mercapto $C_{1-8}$ alkenylsulfinyl group, a $C_{1-8}$ alkylthio $C_{1-8}$ alkenylthio group, a $C_{1-8}$ alkylthio $C_{1-8}$ alkenylsulfonyl group, a $C_{1-8}$ alkylthio $C_{1-8}$ alkenylsulfinyl group, a halogeno $C_{1-8}$ alkenylthio group, a halogeno $C_{1-8}$ alkenylsulfonyl group, a halogeno $C_{1-8}$ alkenylsulfinyl group, a nitro $C_{1-8}$ alkenylthio group, a nitro $C_{1-8}$ alkenylsulfonyl group, a nitro $C_{1-8}$ alkenylsulfinyl group, a cyano $C_{1-8}$ alkenylthio group, a cyano $C_{1-8}$ alkenylsulfonyl group, a cyano $C_{1-8}$ alkenylsulfinyl group, a $C_{2-8}$ alkynylthio group, a $C_{2-8}$ alkynylsulfonyl group, a $C_{2-8}$ alkynylsulfinyl group, a $C_{3-8}$ cycloalkynylthio group, a $C_{3-8}$ cycloalkynylsulfonyl group, a $C_{3-8}$ cycloalkynylsulfinyl group, a $C_{1-8}$ alkyl $C_{3-8}$ cycloalkynylthio group, a $C_{1-8}$ alkyl $C_{3-8}$ cycloalkynylsulfonyl group, a $C_{1-8}$ alkyl $C_{3-8}$ cycloalkynylsulfinyl group, a $C_{1-8}$ alkoxy $C_{1-8}$ alkynylthio group, a $C_{1-8}$ alkoxy $C_{1-8}$ alkynylsulfonyl group, a $C_{1-8}$ alkoxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a mercapto $C_{1-8}$ alkynylthio group, a mercapto $C_{1-8}$ alkynylsulfonyl group, a mercapto $C_{1-8}$ alkynylsulfinyl group, a $C_{1-8}$ alkylthio $C_{1-8}$ alkynylthio group, a $C_{1-8}$ alkylthio $C_{1-8}$ alkynylsulfonyl group, a $C_{1-8}$ alkylthio $C_{1-8}$ alkynylsulfinyl group, a halogeno $C_{1-8}$ alkynylthio group, a halogeno $C_{1-8}$ alkynylsulfonyl group, a halogeno $C_{1-8}$ alkynylsulfinyl group, a nitro $C_{1-8}$ alkynylthio group, a nitro $C_{1-8}$ alkynylsulfonyl group, a cyano $C_{1-8}$ alkynylthio group, a cyano $C_{1-8}$ alkynylsulfonyl group, a cyano $C_{1-8}$ alkynylsulfinyl group, a $C_{6-12}$ arylthio group, a $C_{6-12}$ sulfonyl group, a $C_{6-12}$ arylsulfinyl group, a 5 to 12-membered heteroarylthio group, a 5 to 12-membered heteroarylsulfonyl group, a 5 to 12-membered heteroarylsulfinyl group, a $C_{1-8}$ alkyl $C_{6-12}$ arylthio group, a $C_{1-8}$ alkyl $C_{6-12}$ arylsulfonyl group, a $C_{1-8}$ alkyl $C_{6-12}$ arylsulfinyl group, a $C_{2-8}$ alkenyl $C_{6-12}$ arylthio group, a $C_{2-8}$ alkenyl $C_{6-12}$ arylsulfonyl group, a $C_{2-8}$ alkenyl $C_{6-12}$ arylsulfinyl group, a $C_{2-8}$ alkynyl $C_{6-12}$ arylthio group, a $C_{2-8}$ alkynyl $C_{6-12}$ arylsulfonyl group, a $C_{2-8}$ alkynyl $C_{6-12}$ arylsulfinyl group, a $C_{1-8}$ alkyl 5 to 12-membered heteroarylthio group, a $C_{2-8}$ alkenyl 5 to 12-membered heteroarylthio group, a $C_{5-12}$ alkynyl 5 to 12-membered heteroarylthio group, a hydroxy $C_{6-12}$ arylthio group, a mercapto $C_{6-12}$ arylthio group, a $C_{1-8}$ alkylthio $C_{6-12}$ arylthio group, ahydroxy 5 to 12-membered heteroarylthio group, a hydroxy 5 to 12-membered heteroarylsulfonyl group, a hydroxy 5 to 12-membered heteroarylsulfinyl group, a mercapto 5 to 12-membered heteroarylthio group, a mercapto 5 to 12-membered heteroarylsulfonyl group, a mercapto 5 to 12-membered heteroarylsulfinyl group, a $C_{1-8}$ alkylthio $C_{6-12}$ heteroarylthio group, a $C_{1-8}$ alkylthio $C_{6-12}$ heteroarylsulfonyl group, a $C_{1-8}$ alkylthio $C_{6-12}$ heteroarylsulfinyl group, a halogeno $C_{6-12}$ arylthio group, a halogeno $C_{6-12}$ aryl sulfonyl group, a halogeno $C_{6-12}$ arylsulfinyl group, a nitro $C_{6-12}$ arylthio group, a nitro $C_{6-12}$ arylsulfonyl group, anitro $C_{6-12}$ arylsulfinyl group, a cyano $C_{6-12}$ arylthio group, a cyano $C_{6-12}$ arylsulfonyl group, a cyano $C_{6-12}$ arylsulfinyl group, a halogeno 5 to 12-membered heteroarylthio group, a halogeno 5 to 12-membered heteroaryl sulfonyl group, a halogeno 5 to 12-membered heteroaryl sulfinyl group, a nitro 5 to 12-membered heteroarylthio group, a nitro 5 to 12-membered heteroarylsulfonyl group, a nitro 5 to 12-membered heteroarylsulfinyl group, a cyano 5 to 12-membered heteroarylthio group, a cyano 5 to 12-membered heteroaryl sulfonyl group, a cyano 5 to 12-membered heteroaryl sulfinyl group, a $C_{6-12}$ aryl $C_{1-8}$ alkylthio group, a $C_{6-12}$ aryl $C_{1-8}$ alkylsulfonyl group, a $C_{6-12}$ aryl $C_{1-8}$ alkylsulfinyl group, a $C_{6-12}$ aryl $C_{2-8}$ alkenylthio group, a $C_{6-12}$ aryl $C_{2-8}$ alkenylsulfonyl group, a $C_{6-12}$ aryl $C_{2-8}$ alkenylsulfinyl group, a $C_{6-12}$ aryl $C_{2-8}$ alkynylthio group, a $C_{6-12}$ aryl $C_{2-8}$ alkynylsulfonyl group, a $C_{6-12}$ aryl $C_{2-8}$ alkynylsulfinyl group, a 5 to 12-membered heteroaryl $C_{1-8}$ alkylthio group, a 5 to 12-membered heteroaryl $C_{1-8}$ alkylsulfonyl group, a 5 to 12-membered heteroaryl $C_{1-8}$ alkylsulfinyl group, a 5 to 12-membered heteroaryl $C_{2-8}$ alkenylthio group, a 5 to 12-membered heteroaryl $C_{2-8}$ alkenylsulfonyl group, a 5 to 12-membered heteroaryl $C_{2-8}$ alkenylsulfinyl group, a 5 to 12-membered heteroaryl $C_{2-8}$ alkynylthio group, a 5 to 12-membered heteroaryl $C_{2-8}$ alkynylsulfonyl a 5 to 12-membered heteroaryl $C_{2-8}$ alkynylsulfinyl group, a $C_{1-8}$ alkyl $C_{6-12}$ aryl $C_{1-8}$ alkylthio group, a $C_{1-8}$ alkyl $C_{6-12}$ aryl $C_{1-8}$ alkylsulfonyl group, a $C_{1-8}$ alkyl $C_{6-12}$ aryl $C_{1-8}$ alkylsulfinyl group, a $C_{1-8}$ alkyl $C_{6-12}$ aryl $C_{2-8}$ alkenylthio group, a $C_{1-8}$ alkyl $C_{6-12}$ aryl $C_{2-8}$ alkenylsulfonyl group, a $C_{1-8}$ alkyl $C_{6-12}$ aryl $C_{2-8}$ alkenylsulfinyl group, a $C_{1-8}$ alkyl $C_{6-12}$ aryl $C_{2-8}$ alkynylthio group, a $C_{1-8}$ alkyl $C_{6-12}$ aryl $C_{2-8}$ alkynylsulfonyl group, a $C_{1-8}$ alkyl $C_{6-12}$ aryl $C_{2-8}$ alkynylsulfinyl group, a $C_{2-8}$ alkenyl $C_{6-12}$ aryl $C_{1-8}$ alkylthio group, $C_{2-8}$ alkenyl $C_{6-12}$ aryl $C_{1-8}$ alkylsulfonyl group, a $C_{2-8}$ alkenyl $C_{6-12}$ aryl $C_{1-8}$ alkylsulfinyl group, a $C_{2-8}$ alkenyl $C_{6-12}$ aryl $C_{2-8}$ alkenylthio group, a $C_{2-8}$ alkenyl $C_{6-12}$ aryl $C_{2-8}$ alkenylsulfonyl group, a $C_{2-8}$ alkenyl $C_{6-12}$ aryl $C_{2-8}$ alkenylsulfinyl group, a $C_{2-8}$ alkenyl $C_{6-12}$ aryl $C_{2-8}$ alkynylthio group, a $C_{2-8}$ alkenyl $C_{6-12}$ aryl $C_{2-8}$ alkynylsulfonyl group, a $C_{2-8}$ alkenyl $C_{6-12}$ aryl $C_{2-8}$ alkynylsulfinyl group, a $C_{2-8}$ alkynyl $C_{6-12}$ aryl $C_{1-8}$ alkylthio group, a $C_{2-8}$ alkynyl $C_{6-12}$ aryl $C_{1-8}$ alkylsulfonyl group, a $C_{2-8}$ alkynyl $C_{6-12}$ aryl $C_{1-8}$ alkylsulfinyl group, a $C_{2-8}$ alkynyl $C_{6-12}$ aryl $C_{2-8}$ alkenylthio group, a $C_{2-8}$ alkynyl $C_{6-12}$ aryl $C_{1-8}$ alkenylsulfonyl group, a $C_{2-8}$ alkynyl $C_{6-12}$ aryl $C_{2-8}$ alkenylsulfinyl group, a $C_{2-8}$ alkynyl $C_{6-12}$ aryl $C_{2-8}$ alkynylthio group, a $C_{2-8}$ alkynyl $C_{6-12}$ aryl $C_{2-8}$ alkynylsulfonyl group, a $C_{2-8}$ alkynyl $C_{6-12}$ aryl $C_{2-8}$ alkynylsulfinyl group, a $C_{1-8}$ alkyl 5 to 12-membered heteroaryl $C_{1-8}$ alkylthio group, a $C_{1-8}$ alkyl 5 to 12-membered heteroaryl $C_{1-8}$ alkylsulfonyl group, a $C_{1-8}$ alkyl 5 to 12-membered heteroaryl $C_{1-8}$ alkylsulfinyl group, a $C_{1-8}$ alkyl 5 to 12-membered heteroaryl $C_{2-8}$ alkenylthio group, a $C_{1-8}$ alkyl 5 to 12-membered heteroaryl $C_{2-8}$ alkenylsulfonyl group, a $C_{1-8}$ alkyl 5 to 12-membered heteroaryl $C_{2-8}$ alkenylsulfinyl group, a $C_{1-8}$ alkyl 5 to 12-membered heteroaryl $C_{2-8}$ alkynylthio group, a $C_{1-8}$ alkyl 5 to 12-membered heteroaryl $C_{2-8}$ alkynylsulfonyl group, a $C_{1-8}$ alkyl 5 to 12-membered heteroaryl $C_{2-8}$ alkynylsulfinyl group, a $C_{2-8}$ alkenyl 5 to 12-membered heteroaryl $C_{1-8}$ alkylthio group, a $C_{2-8}$ alkenyl 5 to 12-membered heteroaryl $C_{1-8}$ alkylsulfonyl group, a $C_{2-8}$ alkenyl 5 to 12-membered heteroaryl $C_{1-8}$ alkylsulfinyl group, a $C_{2-8}$ alkenyl 5 to 12-membered heteroaryl $C_{2-8}$ alkenylthio group, a $C_{2-8}$ alkenyl 5 to 12-membered heteroaryl $C_{2-8}$ alkenylsulfonyl group, a $C_{2-8}$ alkenyl 5 to 12-membered heteroaryl $C_{2-8}$ alkenylsulfinyl group, a $C_{2-8}$ alkenyl 5 to 12-membered heteroaryl $C_{2-8}$ alkynylthio group, a $C_{2-8}$ alkenyl 5 to 12-membered heteroaryl $C_{2-8}$ alkynylsulfonyl group, a $C_{2-8}$ alkenyl 5 to 12-membered heteroaryl $C_{2-8}$ alkynylsulfinyl group, a $C_{2-8}$ alkynyl 5 to 12-membered heteroaryl $C_{1-8}$ alkylthio group, a $C_{2-8}$ alkynyl 5 to 12-membered heteroaryl $C_{1-8}$ alkylsulfonyl group, a $C_{2-8}$ alkynyl 5 to 12-membered heteroaryl $C_{1-8}$ alkylsulfinyl group, a $C_{2-8}$ alkynyl 5 to 12-membered heteroaryl $C_{2-8}$ alkenylthio group, a $C_{2-8}$ alkynyl 5 to 12-membered heteroaryl $C_{2-8}$ alkenylsulfonyl group, a $C_{2-8}$ alkynyl 5 to 12-membered heteroaryl $C_{2-8}$ alkenylsulfinyl group, a $C_{2-8}$ alkynyl 5 to 12-membered heteroaryl $C_{2-8}$ alkynylthio group, a $C_{2-8}$ alkynyl 5 to 12-membered heteroaryl $C_{2-8}$ alkynylsulfonyl group, a $C_{2-8}$ alkynyl 5 to 12-membered heteroaryl $C_{2-8}$ alkynyl sulfinyl group, an amino $C_{1-8}$ alkyl group, a $C_{1-8}$ alklyamino $C_{1-8}$ alkyl group, di($C_{1-8}$ alkyl)amino $C_{1-8}$alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroaryamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkodyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membererd heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{1-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl gorup, 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group; and Y represents oxygen atom, sulfur atom or the formula $R^4N$ (wherein $R^4$ represents hydrogen atom, hydroxy group, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{1-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio $C_{6-12}$ heteroaryl group, a $C_{1-8}$ alkylsulfonyl $C_{6-12}$ heteroaryl group, $C_{1-8}$ alkylsulfinyl $C_{6-12}$ heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino $C_{1-8}$ alkyl group, a $C_{1-8}$ alkylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl) amino $C_{2-6}$ alkenyl group, a 5 to 12-membered heteroarylamino $C_{2-8}$ alkenyl group, di(5 to 12-membered heteroaryl) amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl) amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected if necessary and may be substituted by at least one $Z^4$, and $R^4$ may form, together with $R^3$, 5, 6 or 7-membered heterocyclic group of monocycle or bicycle, which may further contains 0 to 4 hetero atoms selected from N, O, $S(O)_n$ (wherein, n represents 0, 1 or 2))

The invention includes the following embodiments (1) to (5):

Embodiment (1)

A process for producing an α-hydroxy-carbonyl compound or an α-protected hydroxy-carbonyl compound represented by the formula (IV) or (IV'):

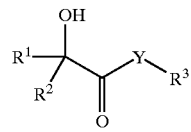

(IV)

or

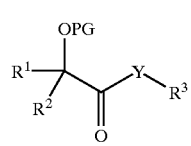

(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

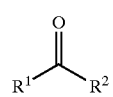

(I)

wherein, $R^1$ and $R^2$ are the same as or different from each other and each represents an organic group;

$$R^3\text{—YH} \quad (II)$$

wherein, $R^3$ represents an organic group, and Y represents oxygen atom, sulfur atom or the formula $R^4N$ (wherein $R^4$ represents an organic group); and

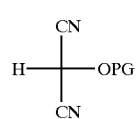

(III)

wherein, PG represents:
a) a silyl group which may be substituted by at least one selected from the group consisting of an alkyl group, an alkoxy group, a cycloalkyl group, an optionally substituted aryl group and an optionally substituted heteroaryl group;
b) an alkanoyl group;
c) an alkenoyl group;
d) an alkynoyl group;
e) an aryloyl group;
f) a heteroaryloyl group;
g) an arylalkanoyl group;
h) a heteroarylalkanoyl group;
i) an alkylarylalkanoyl group;
j) an alkylsulfonyl group;
k) an alkylsulfinyl group;
l) an arylsulfonyl group;
m) an arylsulfinyl group;
n) a heteroarylsulfonyl group;
o) a heteroarylsulfinyl group;

p) an arylalkylsulfonyl group;
q) an arylalkylsulfinyl group;
r) a heteroarylalkylsulfonyl group;
s) a heteroarylalkylsulfinyl group;
t) an alkylarylsulfonyl group;
u) an alkylarylsulfinyl group;
v) an alkylheteroarylsulfonyl group;
w) an alkylheteroarylsulfinyl group;
x) an alkylphonphonyl group;
y) an arylphosphonyl group; or
z) a heteroarylphosphonyl group.

Embodiment (2)

A process for producing an α-hydroxy-carbonyl compound or an α-protected hydroxy-carbonyl compound represented by the formula (IV) or (IV'):

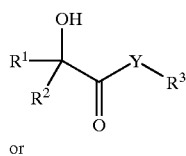
(IV)

or

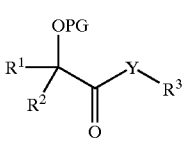
(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

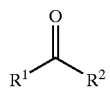
(I)

wherein, $R^1$ and $R^2$ are the same as or different from each other and each represents an aliphatic, alicyclic or aromatic hydrocarbon group, which may be protected, have at least one substituent and have at least one heteroatom;

(II)

wherein, $R^3$ represents an aliphatic, alicyclic or aromatic hydrocarbon group, which may be protected, have at least one substituent and have at least one heteroatom, and an amino group or alkoxy group, which may be protected, have at least one substituent and have at least one heteroatom; and Y represents oxygen atom, sulfur atom or the formula $R^4N$ (wherein $R^4$ represents an aliphatic, alicyclic or aromatic hydrocarbon group, which may be protected, have at least one substituent and have at least one heteroatom); and

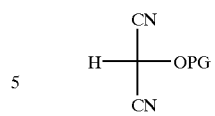
(III)

wherein, PG represents:
a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
b) a $C_{2-9}$ alkanoyl group;
c) a $C_{3-9}$ alkenoyl group;
d) a $C_{3-9}$ alkynoyl group;
e) a $C_{7-13}$ aryloyl group;
f) a 5 to 12-membered heteroaryloyl group;
g) a $C_{6-12}$ aryl $C_{2-9}$ alkanoyl group;
h) a 5 to 12-membered heteroaryl $C_{2-9}$ alkanoyl group;
i) a $C_{1-8}$ alkyl $C_{6-12}$ aryl $C_{2-9}$ alkanoyl group;
j) a $C_{1-8}$ alkylsulfonyl group;
k) a $C_{1-8}$ alkylsulfinyl group;
l) a $C_{6-12}$ arylsulfonyl group;
m) a $C_{6-12}$ arylsulfinyl group;
n) a 5 to 12-membered heteroarylsulfonyl group;
o) a 5 to 12-membered heteroarylsulfinyl group;
p) a $C_{6-12}$ aryl $C_{1-8}$ alkylsulfonyl group;
q) a $C_{6-12}$ aryl $C_{1-8}$ alkylsulfinyl group;
r) a 5 to 12-,membered heteroaryl $C_{1-8}$ alkylsulfonyl group;
s) a 5 to 12-membered heteroaryl $C_{1-8}$ alkylsulfinyl group;
t) a $C_{1-8}$ alkyl $C_{6-12}$ arylsulfonyl group;
u) a $C_{1-8}$ alkyl $C_{6-12}$ arylsulfinyl group;
v) a $C_{1-8}$ alkyl 5 to 12-membered heteroarylsulfonyl group;
w) a $C_{1-8}$ alkyl 5 to 12-membered heteroarylsulfinyl group;
x) a $C_{1-8}$ alkylphosphonyl group;
y) a $C_{6-12}$ arylphosphonyl group; or
z) a 5 to 12-membered heteroarylphosphonyl group.

Embodiment (3)

A process for producing an α-hydroxy-carbonyl compound or an α-protected hydroxy-carbonyl compound represented by the formula (IV) or (IV'):

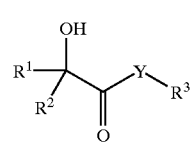
(IV)

or

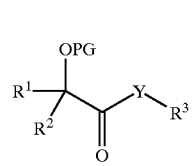
(IV')

(wherein, $R^1$, $R^2$, $R^3$, PG and Y respectively have the same meanings as defined below), which comprises the steps of reacting the compound represented by the formula (I):

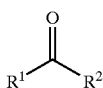

(I)

(wherein, R¹ and R² are the same as or different from each other and each represents hydrogen atom, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ a alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ B alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl alkenyl group, a $C_{1-8}$ alkylsulfinyl alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonylalkynyl group, a $C_{1-8}$ alkylsulfinylalkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5- to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ aklynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl a $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino $C_{1-8}$ alkyl group, a $C_{1-8}$ alkylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-8}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl) amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl) amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membered heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected if necessary, and are independent of each other and may be substituted by at least one optional group selected from the group represented by $Z^1$ (wherein, $Z^1$ has the same meaning as $Z^3$); provided that the compound in which both R¹ and R² are hydrogen atoms is excluded.), the compound represented by the formula (II):

$$R^3-YH \qquad (II)$$

(wherein, R³ represents hydrogen atom, hydroxy group, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ 6 alkyl $C_{3-8}$ cycloalkenyl group, a $C_{1-8}$ alkoxyl $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5-12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{6-12}$ arylamino group, di($C_{6-12}$ aryl)amino group, a $C_{1-8}$ alkyl($C_{6-12}$ aryl)amino group, a 5 to 12-membered heteroarylamino group, di(5 to 12-membered heteroaryl)amino group, a $C_{1-8}$ alkyl(5 to 12-membered heteroaryl)amino group, an amino $C_{1-8}$ alkyl group, a $C_{1-8}$ alkylamino $C_{1-8}$ alkyl group, di($C_{1-8}$ alkyl)amino $C_{1-8}$ alkyl gorup, a $C_{1-8}$ alkoxyamino $C_{1-8}$ alkyl gorup, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl) amino $C_{2-8}$ alkenyl group, a 5 to 12-membered heteroarylamino $C_{2-8}$ alkenyl group, di(5 to 12-membered heteroaryl) amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl) amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N-$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl) amino group, a 5 to 12-membered heteroarylamino group, di(5 to 12-membered heteroaryl)amino group, a $C_{1-8}$ alkyl(5 to 12-membered heteroaryl)amino group, a $C_{1-8}$ alkyl group, a $C_{3-8}$ cycloalkyl group, a $C_{4-8}$ bicycloalkyl group, a $C_{1-8}$ alkyl $C_{3-8}$ cyclo alkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkylthio group, a $C_{1-8}$ alkyl sulfonyl $C_{1-8}$ alkyl group, a $C_{1-8}$ alkylsulfinyl $C_{1-8}$ alkyl group, a halogeno $C_{1-8}$ alkyl gorup, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryll group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, a $C_{1-8}$ alkoxy group, a $C_{3-8}$ cycloalkoxy group, a $C_{4-8}$ bicycloalkoxy group, a $C_{1-8}$ alkyl $C_{3-8}$ cycloalkoxy group, a $C_{1-8}$ alkoxy $C_{1-8}$ alkoxy group, a hydroxy $C_{1-8}$ alkoxy group, a mercapto $C_{1-8}$ alkoxy group, a $C_{1-8}$ alkylthio $C_{1-8}$ alkoxy group, a $C_{1-8}$ alkylsulfonyl $C_{1-8}$ alkoxy group, a $C_{1-8}$ alkylsulfinyl $C_{1-8}$ alkoxy group, a halogeno $C_{1-8}$ alkoxy group, a nitro $C_{1-8}$ alkoxy group, a cyano $C_{1-8}$ alkoxy group, a $C_{1-8}$ alkoxycarbonyl $C_{1-8}$ alkoxy group, a $C_{1-8}$ alkylthiocarbonyl $C_{1-8}$ alkoxy group, a $C_{2-9}$ alkanoyl $C_{1-8}$ alkoxy group, a $C_{2-9}$ alkanoyloxy $C_{1-8}$ alkoxy group, a $C_{2-8}$ alkenyloxy group, a $C_{3-8}$ cycloalkenyloxy group, a $C_{1-8}$ alkyl $C_{3-8}$ cycloalkenyloxy group, a $C_{1-8}$ alkoxy $C_{1-8}$ alkenyloxy group, a hydroxy $C_{1-8}$ alkenyloxy group, a mercapto $C_{1-8}$ alkenyloxy group, a $C_{1-8}$ alkylthio $C_{1-8}$ alkenyloxy group, a $C_{1-8}$ alkylsulfonyl $C_{1-8}$ alkenyloxy group, a $C_{1-8}$ alkylsulfinyl $C_{1-8}$ alkenyloxy group, a halogeno $C_{1-8}$ alkenyloxy group, a nitro $C_{1-8}$ alkenyloxy group, a cyano $C_{1-8}$ alkenyloxy group, a $C_{2-8}$ alkynyloxy group, a $C_{3-8}$ cycloalkynyloxy group, a $C_{1-8}$ alkyl $C_{3-8}$ cycloalkynyloxy group, a $C_{1-8}$ alkoxy $C_{1-8}$ alkynyloxy group, a hydroxy $C_{1-8}$ a alkynyloxy group, a mercapto $C_{1-8}$ alkynyloxy group, a $C_{1-8}$ alkylthio $C_{1-8}$ alkynyloxy group, a $C_{1-8}$ alkylsulfonyl $C_{1-8}$ alkynyloxy group, a $C_{1-8}$ alkylsulfinyl $C_{1-8}$ alkynyloxy group, a halogeno $C_{1-8}$ alkynyloxy group, a nitro $C_{1-8}$ alkynyloxy group, a cyano $C_{1-8}$ alkynyloxy group, a $C_{6-12}$ aryloxy group, a 5 to 12-membered heteroaryloxy group, a $C_{1-8}$ alkyl $C_{6-12}$ aryloxy group, a $C_{2-8}$ alkenyl $C_{6-12}$ aryloxy group, a $C_{2-8}$ alkynyl $C_{6-12}$ aryloxy group, a $C_{1-8}$ alkyl 5 to 12-membered heteroaryloxy group, a $C_{2-8}$ alkenyl 5 to 12-membered heteroaryloxy group, a $C_{5-12}$ alkynyl 5 to 12-membered heteroaryloxy group, a hydroxy $C_{6-12}$ aryloxy group, a mercapto $C_{6-12}$ aryloxy group, a $C_{1-8}$ alkylthio $C_{6-12}$ aryloxy group, a $C_{1-8}$ alkylsulfonyl $C_{6-12}$ aryloxy group, a $C_{1-8}$ alkylsulfinyl $C_{6-12}$ aryloxy group, a hydroxy 5 to 12-membered heteroaryloxy group, a mercapto 5 to 12-membered heteroaryloxy group, a $C_{1-8}$ alkylthio $C_{6-12}$ heteroaryloxy group, a $C_{1-8}$ alkylsulfonyl $C_{6-12}$ heteroaryloxy group, a $C_{1-8}$ alkylsulfinyl $C_{6-12}$ heteroaryloxy group, a halogeno $C_{6-12}$ aryloxy group, a nitro $C_{6-12}$ aryloxy group, a cyano $C_{6-12}$ aryloxy group, a halogeno 5 to 12-membered heteroaryloxy group, a nitro 5 to 12-membered heteroaryloxy group, a cyano 5 to 12-membered heteroaryloxy group, a $C_{6-12}$ aryl $C_{1-8}$ alkoxyl group, a $C_{6-12}$ aryl $C_{2-8}$ alkenyloxy group, a $C_{6-12}$ aryl $C_{2-8}$ alkynyloxy group, a 5 to 12-membered heteroaryl $C_{1-8}$ alkoxy group, a 5 to 12-membered heteroaryl $C_{2-8}$ alkenyloxy group, a 5 to 12-membered heteroaryl $C_{2-8}$ alkynyloxy group, a $C_{1-8}$ alkyl $C_{6-12}$ aryl $C_{1-8}$ alkoxyl group, a $C_{1-8}$ alkyl $C_{6-12}$ aryl $C_{2-8}$ alkenyloxy group, a $C_{1-8}$ alkyl $C_{6-12}$ aryl $C_{2-8}$ alkynyloxy group, a $C_{2-8}$ alkenyl $C_{6-12}$ aryl $C_{1-8}$ alkoxy group, a $C_{2-8}$ alkenyl $C_{6-12}$ aryl $C_{2-8}$ alkenyloxy group, a $C_{2-8}$ alkenyl $C_{6-12}$ aryl $C_{2-8}$ alkynyloxy group, a $C_{2-8}$ alkynyl $C_{6-12}$ aryl $C_{1-8}$ alkoxy group, a $C_{2-8}$ alkynyl $C_{6-12}$ aryl $C_{2-8}$ alkenyloxy group, a $C_{2-8}$ alkynyl $C_{6-12}$ aryl $C_{2-8}$ alkynyloxy group, a $C_{1-8}$ alkyl 5 to 12-membered heteroaryl $C_{1-8}$ alkoxy group, a $C_{1-8}$ alkyl 5 to 12-membererd heteroaryl $C_{2-8}$ alkenyloxy group, a $C_{1-8}$ alkyl 5 to 12-membered heteroaryl $C_{2-8}$ alkynyloxy group, a $C_{2-8}$ alkenyl 5 to 12-membered heteroaryl $C_{1-8}$ alkoxy group, a $C_{2-8}$ alkenyl 5 to 12-membered heteroaryl $C_{2-8}$ alkenyloxy group, a $C_{2-8}$ alkenyl 5 to 12-membererd heteroaryl $C_{2-8}$ alkynyloxy group, a $C_{2-8}$ alkynyl 5 to 12-membered heteroaryl $C_{1-8}$ alkoxy group, a $C_{2-8}$ alkynyl 5 to 12-membered heteroaryl $C_{2-8}$ alkenyloxy group, a $C_{2-8}$ alkynyl 5 to 12-membered heteroaryl $C_{2-8}$ alkynyloxy group, a $C_{1-8}$ alkylthio group, a $C_{1-8}$ alkylsulfonyl group, a $C_{1-8}$ alkylsulfinyl group, a $C_{3-8}$ cycloalkylthio group, a $C_{3-8}$ cycloalkylsulfonyl group, a $C_{3-8}$ cycloalkylsulfinyl group, a $C_{4-8}$ bicycloalkylthio group, a $C_{4-8}$ bicycloalkylsulfonyl group, a $C_{4-8}$ bicycloalkylsulfinyl group, a $C_{1-8}$ alkyl $C_{3-8}$ cycloalkylthio group, a $C_{1-8}$ alkyl $C_{3-8}$ cycloalkylsulfonyl group, a $C_{1-8}$ alkyl $C_{3-8}$ cycloalkylsulfinyl group, a $C_{1-8}$ alkoxy $C_{1-8}$ alkylthio group, a $C_{1-8}$ alkoxy $C_{1-8}$ alkylsulfonyl group, a $C_{1-8}$ alkoxy $C_{1-8}$ alkylsulfinyl group, a hydroxy $C_{1-8}$ alkylthio group, a hydroxy $C_{1-8}$ alkylsulfonyl group, a hydroxy $C_{1-8}$ alkylsulfinyl group, a mercapto $C_{1-8}$ alkylthio group, a mercapto $C_{1-8}$ alkylsulfonyl group, a mercapto $C_{1-8}$ alkylsulfinyl group, a halogeno $C_{1-8}$ alkylthio group, a halogeno $C_{1-8}$ alkylsulfonyl group, a halogeno $C_{1-8}$ alkylsulfinyl group, a nitro $C_{1-8}$ alkylthio group, a nitro $C_{1-8}$ akylsulfonyl group, a nitro $C_{1-8}$ alkylsulfinyl group, a cyano $C_{1-8}$ alkylthio group, a cyano $C_{1-8}$ alkylsulfonyl group, a cyano $C_{1-8}$ alkylsulfinyl group, a $C_{1-8}$ alkoxycarbonyl $C_{1-8}$ alkylthio group, a $C_{1-8}$ alkoxycarbonyl $C_{1-8}$ alkylsulfonyl group, a $C_{1-8}$ alkoxycarbonyl $C_{1-8}$ alkylsulfinyl group, a $C_{1-8}$ alkylthiocarbonyl $C_{1-8}$ alkylthio group, a $C_{1-8}$ alkylthiocarbonyl $C_{1-8}$ alkylsulfonyl group, a $C_{1-8}$ alkylthiocarbonyl $C_{1-8}$ alkylsulfinyl group, a $C_{2-9}$ alkanoyl $C_{1-8}$ alkylthio group, a $C_{2-9}$ alkanoyl $C_{1-8}$ alkylsulfonyl group, a $C_{2-9}$ alkanoyl $C_{1-8}$ alkylsulfinyl group, a $C_{2-9}$ alkanoyloxy $C_{1-8}$ alkylthio group, a $C_{2-9}$ alkanoyloxy $C_{1-8}$ alkylsulfonyl group, a $C_{2-9}$ alkanoyloxy $C_{1-8}$ alkylsulfinyl group, a $C_{2-8}$ alkenylthio group, a $C_{2-8}$ alkenylsulfonyl group, a $C_{2-8}$ alkenylsulfinyl group, a $C_{3-8}$ cycloalkenylthio group, a $C_{3-8}$ cycloalkenylsulfonyl group, a $C_{3-8}$ cycloalkenylsulfinyl group, a $C_{1-8}$ alkyl $C_{3-8}$ cycloalkenylthio group, a $C_{1-8}$ alkyl $C_{3-8}$ cycloalkenylsulfonyl group, a $C_{1-8}$ alkyl $C_{3-8}$ cycloalkenylsulfinyl group, a $C_{1-8}$ alkoxy $C_{1-8}$ alkenylthio group, a $C_{1-8}$ alkoxy $C_{1-8}$ alkenylsulfonyl group, a $C_{1-8}$ alkoxy $C_{1-8}$ alkenylsulfinyl group, a hydroxy $C_{1-8}$ alkenylthio group, a hydroxy $C_{1-8}$ alkenylsulfonyl group, a hydroxy $C_{1-8}$ alkenylsulfinyl group, a mercapto $C_{1-8}$ alkenylthio group, a mercapto $C_{1-8}$ alkenylsulfonyl group, a mercapto $C_{1-8}$ alkenylsulfinyl group, a $C_{1-8}$ alkylthio $C_{1-8}$ alkenylthio group, a $C_{1-8}$ alkylthio $C_{1-8}$ alkenylsulfonyl group, a $C_{1-8}$ alkylthio $C_{1-8}$ alkenylsulfinyl group, a halogeno $C_{1-8}$ alkenylthio group, a halogeno $C_{1-8}$ alkenylsulfonyl group, a halogeno $C_{1-8}$ alkenylsulfinyl group, a nitro $C_{1-8}$ alkenylthio group, a nitro $C_{1-8}$ alkenylsulfonyl group, a nitro $C_{1-8}$ alkenylsulfinyl group, a cyano $C_{1-8}$ alkenylthio group, a cyano $C_{1-8}$ alkenylsulfonyl group, a cyano $C_{1-8}$ alkenylsulfinyl group, a $C_{2-8}$ alkynylthio group, a $C_{2-8}$ alkynylsulfonyl group, a $C_{2-8}$ alkynylsulfinyl group, a $C_{3-8}$ cycloalkynylthio group, a $C_{3-8}$ cycloalkynylsulfonyl group, a $C_{3-8}$ cycloalkynylsulfinyl group, a $C_{1-8}$ alkyl $C_{3-8}$ cycloalkynylthio group, a $C_{1-8}$ alkyl $C_{3-8}$ cycloalkynylsulfonyl group, a $C_{1-8}$ alkyl $C_{3-8}$ cycloalkynylsulfinyl group, a $C_{1-8}$ alkoxy $C_{1-8}$ alkynylthio group, a $C_{1-8}$ alkoxy $C_{1-8}$ alkynylsulfonyl group, a $C_{1-8}$ alkoxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a mercapto $C_{1-8}$ alkynylthio group, a mercapto $C_{1-8}$ alkynylsulfonyl group, a mercapto $C_{1-8}$ alkynylsulfinyl group, a $C_{1-8}$ alkylthio $C_{1-8}$ alkynylthio group, a $C_{1-8}$ alkylthio $C_{1-8}$ alkynylsulfonyl group, a $C_{1-8}$ alkylthio $C_{1-8}$ alkynylsulfinyl group, a halogeno $C_{1-8}$ alkynylthio group, a halogeno $C_{1-8}$ alkynylsulfonyl group, a halogeno $C_{1-8}$ alkynylsulfinyl group, a nitro $C_{1-8}$ alkynylthio group, a nitro $C_{1-8}$ alkynylsulfonyl group, a nitro $C_{1-8}$ alkynylsulfinyl group, a cyano $C_{1-8}$ alkynylthio group, a cyano $C_{1-8}$ alkynylsulfonyl group, a cyano $C_{1-8}$ alkynylsulfinyl group, a $C_{6-12}$ arylthio group, a $C_{6-12}$ sulfonyl group, a $C_{6-12}$ arylsulfinyl group, a 5 to 12-membered heteroarylthio group, a 5 to 12-membered heteroarylsulfonyl group, a 5 to 12-membered heteroarylsulfinyl group, a $C_{1-8}$ alkyl $C_{6-12}$ arylthio group, a $C_{1-8}$ alkyl $C_{6-12}$ arylsulfonyl group, a $C_{1-8}$ alkyl $C_{6-12}$ arylsulfinyl group, a $C_{2-8}$ alkenyl $C_{6-12}$ arylthio group, a $C_{2-8}$ alkenyl $C_{6-12}$ arylsulfonyl group, a $C_{2-8}$ alkenyl $C_{6-12}$ arylsulfinyl group, a $C_{2-8}$ alkynyl $C_{6-12}$ arylthio group, a $C_{2-8}$ alkynyl $C_{6-12}$ arylsulfonyl group, a $C_{2-8}$ alkynyl $C_{6-12}$ arylsulfinyl group, a $C_{1-8}$ alkyl 5 to 12-membered heteroarylthio group, a $C_{2-8}$ alkenyl 5 to 12-memnbered heteroarylthio group, a $C_{5-12}$ alkynyl 5 to 12-membered heteroarylthio group, a hydroxy $C_{6-12}$ arylthio group, a mercapto $C_{6-12}$ arylthio group, a $C_{1-8}$ alkylthio $C_{6-12}$ arylthio group, a hydroxy 5 to 12-membered heteroarylthio group, a hydroxy 5 to 12-membered heteroarylsulfonyl group, a hydroxy 5 to 12-membered heteroarylsulfinyl group, a mercapto 5 to 12-membered heteroarylthio group, a mercapto 5 to 12-membered heteroarylsulfonyl group, a mercapto 5 to 12-membered heteroarylsulfinyl group, a $C_{1-8}$ alkylthio $C_{6-12}$ heteroarylthio group, a $C_{1-8}$ alkylthio $C_{6-12}$ heteroarylsulfonyl group, a $C_{1-8}$ alkylthio $C_{6-12}$ heteroarylsulfinyl group, a halogeno $C_{6-12}$ arylthio group, a halogeno $C_{6-12}$ aryl sulfonyl group, a halogeno $C_{6-12}$ arylsulfinyl group, a nitro $C_{6-12}$ arylthio group, a nitro $C_{6-12}$ arylsulfonyl group, a nitro $C_{6-12}$ arylsulfinyl group, a cyano $C_{6-12}$ arylthio group, a cyano $C_{6-12}$ arylsulfonyl group, a cyano $C_{6-12}$ arylsulfinyl group, a halogeno 5 to 12-membered heteroarylthio group, a halogeno 5 to 12-membered heteroaryl sulfonyl group, a halogeno 5 to 12-membered heteroaryl sulfinyl group, a nitro 5 to 12-membered heteroarylthio group, a nitro 5 to 12-membered heteroarylsulfonyl group, a nitro 5 to 12-membered heteroarylsulfinyl group, a cyano 5 to 12-membered heteroarylthio group, a cyano 5 to 12-membered heteroaryl sulfonyl group, a cyano 5 to 12-membered heteroaryl sulfinyl group, a $C_{6-12}$ aryl $C_{1-8}$ alkylthio group, a $C_{6-12}$ aryl $C_{1-8}$ alkylsulfonyl group, a $C_{6-12}$ aryl $C_{1-8}$ alkylsulfinyl group, a $C_{6-12}$ aryl $C_{2-8}$ alkenylthio group, a $C_{6-12}$ aryl $C_{2-8}$ alkenylsulfonyl group, a $C_{6-12}$ aryl $C_{2-8}$ alkenylsulfinyl group, a $C_{6-12}$ aryl $C_{2-8}$ alkynylthio group, a $C_{6-12}$ aryl $C_{2-8}$ alkynylsulfonyl group, a $C_{6-12}$ aryl $C_{2-8}$ alkynylsulfinyl group, a 5 to 12-membered heteroaryl $C_{1-8}$ alkylthio group, a 5 to 12-membered heteroaryl $C_{1-8}$ alkylsulfonyl group, a 5 to 12-membered heteroaryl $C_{1-8}$ alkylsulfinyl group, a 5 to 12-membered heteroaryl $C_{2-8}$ alkenylthio group, a 5 to 12-membered heteroaryl $C_{2-8}$ alkenylsulfonyl group, a 5 to 12-membered heteroaryl $C_{2-8}$ alkenylsulfinyl group, a 5 to 12-memnbered heteroaryl $C_{2-8}$ alkynylthio group, a 5 to 12-membered heteroaryl $C_{2-8}$ alkynylsulfonyl a 5 to 12-membered heteroaryl $C_{2-8}$ alkynylsulfinyl group, a $C_{1-8}$ alkyl $C_{6-12}$ aryl $C_{1-8}$ alkylthio group, a $C_{1-8}$ alkyl $C_{6-12}$ aryl $C_{1-8}$ alkylsulfonyl group, a $C_{1-8}$ alkyl $C_{6-12}$ aryl $C_{1-8}$ alkylsulfinyl group, a $C_{1-8}$ alkyl $C_{6-12}$ aryl $C_{2-8}$ alkenylthio group, a $C_{1-8}$ alkyl $C_{6-12}$ aryl $C_{2-8}$ alkenylsulfonyl group, a $C_{1-8}$ alkyl $C_{6-12}$ aryl $C_{2-8}$ alkenylsulfinyl group, a $C_{1-8}$ alkyl $C_{6-12}$ aryl $C_{2-8}$ alkynylthio group, a $C_{1-8}$ alkyl $C_{6-12}$ aryl $C_{2-8}$ alkynylsulfonyl group, a $C_{1-8}$ alkyl $C_{6-12}$ aryl $C_{2-8}$ alkynylsulfinyl group, a $C_{2-8}$ alkenyl $C_{6-12}$ aryl $C_{1-8}$ alkylthio group, $C_{2-8}$ alkenyl $C_{6-12}$ aryl $C_{1-8}$ alkylsulfonyl group, a $C_{2-8}$ alkenyl $C_{6-12}$ aryl $C_{1-8}$ alkylsulfinyl group, a $C_{2-8}$ alkenyl $C_{6-12}$ aryl $C_{2-8}$ alkenylthio group, a $C_{2-8}$ alkenyl $C_{6-12}$ aryl $C_{2-8}$ alkenylsulfonyl group, a $C_{2-8}$ alkenyl $C_{6-12}$ aryl $C_{2-8}$ alkenylsulfinyl group, a $C_{2-8}$ alkenyl $C_{6-12}$ aryl $C_{2-8}$ alkynylthio group, a $C_{2-8}$ alkenyl $C_{6-12}$ aryl $C_{2-8}$ alkynylsulfonyl group, a $C_{2-8}$ alkenyl $C_{6-12}$ aryl $C_{2-8}$ alkynylsulfinyl group, a $C_{2-8}$ alkynyl $C_{6-12}$ aryl $C_{1-8}$ alkylthio group, a $C_{2-8}$ alkynyl $C_{6-12}$ aryl $C_{1-8}$ alkylsulfonyl group, a $C_{2-8}$ alkynyl $C_{6-12}$ aryl $C_{1-8}$ alkylsulfinyl group, a $C_{2-8}$ alkynyl $C_{6-12}$ aryl $C_{2-8}$ alkenylthio group, a $C_{2-8}$ alkynyl $C_{6-12}$ aryl $C_{2-8}$ alkenylsulfonyl group, a $C_{2-8}$ alkynyl $C_{6-12}$ aryl $C_{2-8}$ alkenylsulfinyl group, a $C_{2-8}$ alkynyl $C_{1-12}$ aryl $C_{2-8}$ alkynylthio group, a $C_{2-8}$ alkynyl $C_{6-12}$ aryl $C_{2-8}$ alkynylsulfonyl group, a $C_{2-8}$ alkynyl $C_{6-12}$ aryl $C_{2-8}$ alkynylsulfinyl group, a $C_{1-8}$ alkyl 5 to 12-membered heteroaryl $C_{1-8}$ alkylthio group, a $C_{1-8}$ alkyl 5 to 12-membered heteroaryl $C_{1-8}$ alkylsulfonyl group, a $C_{1-8}$ alkyl 5 to 12-membered heteroaryl $C_{1-8}$ alkylsulfinyl group, a $C_{1-8}$ alkyl 5 to 12-membered heteroaryl $C_{2-8}$ alkenylthio group, a $C_{1-8}$ alkyl 5 to 12-membered heteroaryl $C_{2-8}$ alkenylsulfonyl group, a $C_{1-8}$ alkyl 5 to 12-membered heteroaryl $C_{2-8}$ alkenylsulfinyl group, a $C_{1-8}$ alkyl 5 to 12-membered heteroaryl $C_{2-8}$ alkynylthio group, a $C_{1-8}$ alkyl 5 to 12-membererd heteroaryl $C_{2-8}$ alkynylsulfonyl group, a $C_{1-8}$ alkyl 5 to 12-membered heteroaryl $C_{2-8}$ alkynylsulfinyl group, a $C_{2-8}$ alkenyl 5 to 12-membered heteroaryl $C_{1-8}$ alkylthio group, a $C_{2-8}$ alkenyl 5 to 12-membered heteroaryl $C_{1-8}$ alkylsulfonyl group, a $C_{2-8}$ alkenyl 5 to 12-membered heteroaryl $C_{1-8}$ alkylsulfinyl group, a $C_{2-8}$ a alkenyl 5 to 12-membered heteroaryl $C_{2-8}$ alkenylthio group, a $C_{2-8}$ alkenyl 5 to 12-membered heteroaryl $C_{2-8}$ alkenylsulfonyl group, a $C_{2-8}$ alkenyl 5 to 12-membered heteroaryl $C_{2-8}$ alkenylsulfinyl group, a $C_{2-8}$ alkenyl 5 to 12-membered heteroaryl $C_{2-8}$ alkynylthio group, a $C_{2-8}$ alkenyl 5 to 12-membered heteroaryl $C_{2-8}$ alkynylsulfonyl group, a $C_{2-8}$ alkenyl 5 to 12-membered heteroaryl $C_{2-8}$ alkynylsulfinyl group, a $C_{2-8}$ alkynyl 5 to 12-membered heteroaryl $C_{1-8}$ alkylthio group, a $C_{2-8}$ alkynyl 5 to 12-membered heteroaryl $C_{1-8}$ alkylsulfonyl group, a $C_{2-8}$ alkynyl 5 to 12-membered heteroaryl $C_{1-8}$ alkylsulfinyl group, a $C_{2-8}$ alkynyl 5 to 12-membered heteroaryl $C_{2-8}$ alkenylthio group, a $C_{2-8}$ alkynyl 5 to 12-membered heteroaryl $C_{2-8}$ alkenylsulfonyl group, a $C_{2-8}$ alkynyl 5 to 12-membered heteroaryl $C_{2-8}$ alkenylsulfinyl group, a $C_{2-8}$ alkynyl 5 to 12-membered heteroaryl $C_{2-8}$ alkynylthio group, a $C_{2-8}$ alkynyl 5 to 12-membered heteroaryl $C_{2-8}$ alkynylsulfonyl group, a $C_{2-8}$ alkynyl 5 to 12-membered heteroaryl $C_{2-8}$ alkynyl sulfinyl group, an amino $C_{1-8}$ alkyl group, a $C_{1-8}$ alklylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroaryamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{1-8}$ alkenyl group, a $C_{1-8}$ alkodyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membererd heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl gorup, 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected); Y represents oxygen atom, sulfur atom or the formula $R^4N$ (wherein $R^4$ represents hydrogen atom, hydroxy group, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio $C_{6-12}$ heteroaryl group, a $C_{1-8}$ alkylsulfonyl $C_{6-12}$ heteroaryl group, $C_{1-8}$ alkylsulfinyl $C_{6-12}$ heteroaryl group, a halogeno $C_{6-12}$ aryl group, a nitro $C_{6-12}$ aryl group, a cyano $C_{6-12}$ aryl group, a halogen 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino $C_{1-8}$ alkyl group, a $C_{1-8}$ alkylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl) amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl) amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membered heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected if necessary and may be substituted by at least one $Z^4$ which have the same meaning as $Z^3$, and $R^4$ may form, together with $R^3$, 5, 6 or 7-membered heterocyclic group of monocycle or bicycle, which may further contains 0 to 4 hetero atoms selected from N, O, $S(O)_n$ (wherein, n represents 0, 1 or 2); provided that the case $R^3$ is hydrogen atom or hydroxy group when Y is oxygen atom or sulfur atom is excluded.), and the compound represented by the formula (III):

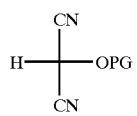

(III)

(wherein, PG represents:
  a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
  b) a $C_{2-9}$ alkanoyl group;
  c) a $C_{3-9}$ alkenoyl group;
  d) a $C_{3-9}$ alkynoyl group;
  e) a $C_{7-13}$ aryloyl group;

f) a 5 to 12-membered heteroaryloyl group;

g) a $C_{6-12}$ aryl $C_{2-9}$ alkanoyl group;

h) a 5 to 12-membered heteroaryl $C_{2-9}$ alkanoyl group;

i) a $C_{1-8}$ alkyl $C_{6-12}$ aryl $C_{2-9}$ alkanoyl group;

j) a $C_{1-8}$ alkylsulfonyl group;

k) a $C_{1-8}$ alkylsulfinyl group;

l) a $C_{6-12}$ arylsulfonyl group;

m) a $C_{6-12}$ arylsulfinyl group;

n) a 5 to 12-memnbered heteroarylsulfonyl group;

o) a 5 to 12-membered heteroarylsulfinyl group;

p) a $C_{6-12}$ aryl $C_{1-8}$ alkylsulfonyl group;

q) a $C_{6-12}$ aryl $C_{1-8}$ alkylsulfinyl group;

r) a 5 to 12-membered heteroaryl $C_{1-8}$ alkylsulfonyl group;

s) a 5 to 12-membered heteroaryl $C_{1-8}$ alkylsulfinyl group;

t) a $C_{1-8}$ alkyl $C_{6-12}$ arylsulfonyl group;

u) a $C_{1-8}$ alkyl $C_{6-12}$ arylsulfinyl group;

v) a $C_{1-8}$ alkyl 5 to 12-membered heteroarylsulfonyl group;

w) a $C_{1-8}$ alkyl 5 to 12-membered heteroarylsulfinyl group;

x) a $C_{1-6}$ alkylphosphonyl group;

y) a $C_{6-12}$ arylphosphonyl group or z) a 5 to 12-membered heteroarylphosphonyl group.) by one-pot under the condition of, if necessary, activating the compound represented by the above formula (III); and deprotecting, if necessary.

Embodiment (4)

A process for producing an α-hydroxy-carbonyl compound or an α-protected hydroxy-carbonyl compound represented by the formula (IV) or (IV'):

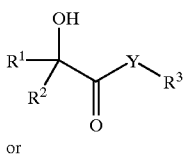

(IV)

or

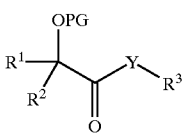

(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

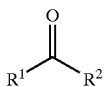

(I)

wherein, $R^1$ and $R^2$ are the same as or different from each other and each represents hydrogen atom, a $C_{1-8}$ alkyl group, a $C_{3-8}$ cycloalkyl group, a $C_{2-8}$ alkenyl group, a $C_{6-12}$ aryl group, a $C_{1-8}$ alkyl $C_{6-12}$ aryl group, a $C_{2-8}$ alkenylaryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group, a $C_{1-8}$ alkyl $C_{6-12}$ aryl $C_{1-8}$ alkyl group or a 5 to 12-membered heteroaryl group, which may be respecteively protected if necessary, and are independent of each other and may be substituted by at least one optional group selected from the group represented by $Z^1$ (wherein, $Z^1$ has the same meaning as $Z^3$), provided that the compound in which both $R^1$ and $R^2$ are hydrogen atoms is excluded;

$$R^3—YH \quad (II)$$

wherein, $R^3$ represents hydrogen atom, a hydroxy group, a $C_{1-8}$ alkyl group, a $C_{3-8}$ cycloalkyl group, a $C_{2-8}$ alkenyl group, a $C_{6-12}$ aryl group, a $C_{1-8}$ alkyl $C_{6-12}$ aryl group, a $C_{2-8}$ alkenylaryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group, a $C_{1-8}$ alkyl $C_{6-12}$ aryl $C_{1-8}$ alkyl group, a 5 to 12-membered heteroaryl group, an amino group or a $C_{1-6}$ alkylamino group, which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N-$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl) amino group, a 5 to 12-membered heteroarylamino group, di(5 to 12-membered heteroaryl)amino group or a $C_{1-8}$ alkyl(5 to 12-membered heteroaryl)amino group, which may be respectively protected if necessary); Y represents oxygen atom, sulfur atom or the formula $R^4N$ (wherein $R^4$ represents hydrogen atom, a hydroxy group, a $C_{1-8}$ alkyl group, a $C_{3-8}$ cycloalkyl group, a $C_{1-8}$ hydroxyalkyl group, a $C_{1-8}$ alkoxycarbonyl $C_{1-8}$ alkyl group, a $C_{2-8}$ alkenyl group, a $C_{6-12}$ aryl group, a $C_{1-8}$ alkyl $C_{6-12}$ aryl group, a $C_{2-8}$ alkenyl $C_{6-12}$ aryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group or a $C_{1-8}$ alkyl $C_{6-12}$ aryl $C_{1-8}$ alkyl group, which may be respectively protected if necessary and may be substituted by at least one $Z^4$ which have the same meaning as $Z^3$, or, in case of $R^4$ forming together with $R^3$, 5, 6 or 7-membered heterocyclic group of monocycle or bicycle, which may further contains 0 to 4 hetero atoms selected from N, O, S(O)$_n$ (wherein, n represents 0, 1 or 2)); provided that the case $R^3$ is hydrogen atom or hydroxy group when Y is oxygen atom or sulfur atom is excluded;

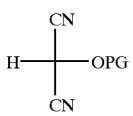 (III)

wherein, PG represents:
a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
b) a $C_{2-9}$ alkanoyl group;
c) a $C_{3-9}$ alkenoyl group;
d) a $C_{3-9}$ alkynoyl group;
e) a $C_{7-13}$ aryloyl group;
f) a 5 to 12-membered heteroaryloyl group;
g) a $C_{6-12}$ aryl $C_{2-9}$ alkanoyl group;
h) a 5 to 12-membered heteroaryl $C_{2-9}$ alkanoyl group;
i) a $C_{1-8}$ alkyl $C_{6-12}$ aryl $C_{2-9}$ alkanoyl group;
j) a $C_{1-8}$ alkylsulfonyl group;
k) a $C_{1-8}$ alkylsulfinyl group;
l) a $C_{6-12}$ arylsulfonyl group;
m) a $C_{6-12}$ arylsulfinyl group;
n) a 5 to 12-membered heteroarylsulfonyl group;
o) a 5 to 12-membered heteroarylsulfinyl group;
p) a $C_{6-12}$ aryl $C_{1-8}$ alkylsulfonyl group;
q) a $C_{6-12}$ aryl $C_{1-8}$ alkylsulfinyl group;
r) a 5 to 12-membered heteroaryl $C_{1-8}$ alkylsulfonyl group;
s) a 5 to 12-membered heteroaryl $C_{1-8}$ alkylsulfinyl group;
t) a $C_{1-8}$ alkyl $C_{6-12}$ arylsulfonyl group;
u) a $C_{1-8}$ alkyl $C_{6-12}$ arylsulfinyl group;
v) a $C_{1-8}$ alkyl 5 to 12-membered heteroarylsulfonyl group;
w) a $C_{1-8\,alkyl}$ 5 to 12-membered heteroarylsulfinyl group;
x) a $C_{1-6}$ alkylphosphonyl group;
y) a $C_{6-12}$ arylphosphonyl group; or
z) a 5 to 12-membered heteroarylphosphonyl group.

Embodiment (5)

A process for producing an α-hydroxy-carbonyl compound or an α-protected hydroxy-carbonyl compound represented by the formula (IV) or (IV'):

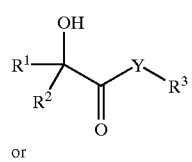 (IV)

or

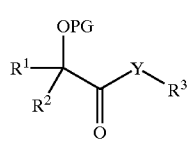 (IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

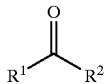 (I)

wherein, $R^1$ and $R^2$ are the same as or different from each other and each represents hydrogen atom, a $C_{1-8}$ a alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respectively protected if necessary, and are independent of each other and may be substituted by at least one optional group selected from the group represented by $Z^1$ (wherein, $Z^1$ has the same meaning as $Z^3$), provided that the compound in which both $R^1$ and $R^2$ are hydrogen atoms is excluded;

 (II)

wherein, $R^3$ represents hydrogen atom, a hydroxy group, a $C_{1-8}$ alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N-$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl)amino group, a 5 to 12-membered heteroarylamino group, di(5 to 12-membered heteroaryl)amino group or a $C_{1-8}$ alkyl(5 to 12-membered heteroaryl)amino group, which may be respectively protected if necessary); Y represents oxygen atom or the formula. $R^4$N (wherein $R^4$ represents hydrogen atom, a hydroxy group, a $C_{1-8}$ alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respectively protected if necessary and may be substituted by at least one $Z^4$ which have the same meaning as $Z^3$, or, in case of $R^4$ forming together with $R^3$, 5 or 6-membered heterocyclic group, which may further contains 0 to 4 hetero atoms selected from N, O, S(O)$_n$ (wherein, n represents 0, 1 or 2)); provided that the case $R^3$ is hydrogen atom or hydroxy group when Y is oxygen atom is excluded;

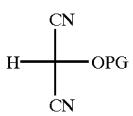
(III)

wherein, PG represents:
a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
b) a $C_{2-9}$ alkanoyl group;
c) a $C_{3-9}$ alkenoyl group;
d) a $C_{3-9}$ alkynoyl group;
e) a $C_{7-13}$ aryloyl group;
f) a 5 to 12-membered heteroaryloyl group;
g) a $C_{6-12}$ aryl $C_{2-9}$ alkanoyl group;
h) a 5 to 12-membered heteroaryl $C_{2-9}$ alkanoyl group;
i) a $C_{1-8}$ alkyl $C_{6-12}$ aryl $C_{2-9}$ alkanoyl group;
j) a $C_{1-8}$ alkylsulfonyl group;
k) a $C_{1-8}$ alkylsulfinyl group;
l) a $C_{6-12}$ arylsulfonyl group;
m) a $C_{6-12}$ arylsulfinyl group;
n) a 5 to 12-membered heteroarylsulfonyl group;
o) a 5 to 12-membered heteroarylsulfinyl group;
p) a $C_{6-12}$ aryl $C_{1-8}$ alkylsulfonyl group;
q) a $C_{6-12}$ aryl $C_{1-8}$ alkylsulfinyl group;
r) a 5 to 12-membered heteroaryl $C_{1-8}$ alkylsulfonyl group;
s) a 5 to 12-membered heteroaryl $C_{1-8}$ alkylsulfinyl group;
t) a $C_{1-8}$ alkyl $C_{6-12}$ arylsulfonyl group;
u) a $C_{1-8}$ alkyl $C_{6-12}$ arylsulfinyl group;
v) a $C_{1-8}$ alkyl 5 to 12-membered heteroarylsulfonyl group;
w) a $C_{1-8}$ alkyl 5 to 12-membered heteroarylsulfinyl group;
x) a $C_{1-6}$ alkylphosphonyl group;
y) a $C_{6-12}$ arylphosphonyl group; or
z) a 5 to 12-membered heteroarylphosphonyl group.

DETAILED DESCRIPTION OF INVENTION

It is preferable in the process of production of the invention that the compound shown by the formula (III) is activated in the presence of a base, in the presence of a Pd complex or at a very high pressure. The base may be a tertiary amine or $K_2CO_3$.

The compounds obtained by the invention include compounds in which PG is trimethylsilyl, t-butyldimethylsilyl or t-butyldiphenylsilyl. In addition PG may be a $C_{2-9}$ alkanoyl, a $C_{7-13}$ aryloyl, a 5–17 membered heteroaryloyl, a $C_{6-12}$ aryl-$C_{2-9}$ alkanoyl, a 5–12 membered heteroaryl-$C_{2-9}$ alkanoyl or a $C_{1-8}$ alkyl-$C_{6-12}$ aryl-$C_{2-9}$ alkanoyl.

The reaction can be effected under conditions used conventionally in organic synthesis. For example the reaction temperature is in the range between −78 and 200° C., preferably between 25° C. and the room temperature. As the solvent a solvent not to be involved in the reaction may be basically used. Alternatively the compound R3-Yh may be also used, such as ethanol, methanol, an aqueous ammonia and diethylamine. Preferable are acetonitrile, diethylether, tetrahydrofuran, dioxane, toluene, benzene, chlorofolm, methylene chloride, hexane, cyclohexane, pentane, N,N-dimethylfolmaldehyde, pyridine and water, in particular diethylether. In order to prevent the reactants from decomposing, the atmosphere of an inert gas such as argon and nitrogen gas or a dehydrating agent such s molecular sieves, magnesium sulfate and sodium sulfate may be used when necessary. The reaction time depends on reactivity of the used reactants, ranging from just after addition of the reactants to several days. Five minutes to 24 hours are appropriate.

Working examples of the invention will be below described.

Synthesis of amides and esters will be experimentally described, referring first to siloxyamide, then hydroxyamide, siloxyester and hydoxyester.

Hereinafter 1 means 2-[(tert-butyldimethylsilyl)oxy] malonitrile and TBS means 2-(tert-butyldimethylsilyl).

Experimental Section

IR spectra were measured with PERKIN-ELMER 1720 Infrared Fourier Transfer Spectrometer indicating with $cm^{-1}$. 1H- and $^3$C-NMR spectra were measured with JEOL JMN-AL300 Spectrometer at 300 MHz and 75 MHz, respectively, in chloroform-d and indicated as δ value. High Resolution Mass Spectra (HRMS) were measured with JEOL JMS-DX303. All aldehydes and ketones were distilled or recrystallized before use. Acetonitrile was distilled over calcium hydride. Anhydrous tetrahydrofuran (THF) and anhydrous ether were purchased from Kanto Chemicals. All the reactions were carried out under nitrogen atmosphere unless otherwise noted.

A Representative Procedure for the Synthesis of α-siloxyamides

To a solution of p-tolualdehyde (120 mg, 1.0 mmol) and 1 of Scheme 1 of page 79 (236 mg, 1.2 mmol) in acetonitrile (3 ml) was added n-butylamine (80 mg, 1.1 mmol) at 0° C. After stirring for 5 min, the reaction mixture was concentrated in vacuo. The residue was purified with silica gel column chromatography by using hexane-ethyl acetate (10/1) as an eluent to give N-butyl-2-[(tert-butyldimethylsilyl) oxy]-2-(4-methylphenyl)acetamide: as a colorless oil (322 mg, 0.96 mmol, 96% yield).

N-Butyl-2-[(tert-butyldimethlylsilyl)oxy]-2-(4-methylphenyl)acetamide

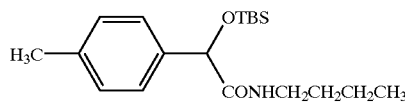

Colorless oil, FT-IR ($CHCl_3$): 3422, 2958, 2932, 1670, 1526, 1090, 870, 840 $cm^{-1}$; $^1$H-NMR (300 MHz): 7.31 (d, J=8.1 Hz, 2H), 7.12 (d, J=8.1 Hz, 2H), 6.79 (br, —NH, 1H), 5.03 (s, 1H), 3.39–3.26 (m, 1H), 3.21–3.09 (m, 1H), 2.32 (s, 3H), 1.52–1.42 (m, 2H), 1.41–1.28 (m, 2H), 0.93 (s, 9H), 0.92 (t, J=7.5 Hz, 3H), 0.08 (s, 3H), −0.04 (s, 3H). $^{13}$C-NMR (100 MHz): 172.0, 137.5, 137.0, 128.9, 126.0, 75.6, 38.5, 31.6, 25.7, 21.1, 20.0, 18.1, 13.6, −4.8, −5.4; EI-HRMS Calcd for $C_{19}H_{33}NO_2Si$ ($M^+$): 335.2280, Found 335.2267.

N-Butyl-2-[(tert-butyldimethylsilyl)oxy]-2-(2-hydroxyphenyl)acetamide

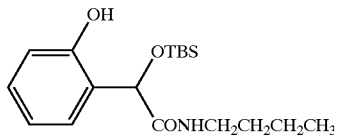

Colorless crystals, mp 72–74° C., FT-IR (CHCl$_3$): 3415, 3180 (br), 2958, 2932, 1651, 1540, 1484, 1265, 1122, 871, 840 cm$^{-1}$; $^1$H-NMR (300 MHz): 9.91 (s, Ar—OH, 1H), 7.34 (brd, J=7.6 Hz, 1H), 7.19 (brt, J=7.6 Hz, 1H), 6.98 (brd, J=7.6 Hz, 1H), 6.90 (brt, J=7.6 Hz, 1H), 6.88 (br, —NR, 1H), 5.41 (s, 1H), 3.46–3.21 (m, 1H), 3.20–3.05 (m, 1H), 1.57–1.43 (m, 2H), 1.43–1.26 (m, 2H), 0.99 (s, 9H), 0.92 (t, J=7.2 Hz, 3H), 0.10 (s, 3H), 0.07 (s, 3H). $^{13}$C-NMR (75 MHz): 174.5, 154.5, 129,0 126.2, 124.6, 119.9, 118.3, 70.8, 38.8, 31.3, 25.7, 19.8, 18.2, 13.5, –5.0, –5.7; Anal. Calcd for C$_{18}$H$_{31}$NO$_3$Si: C, 64.05; H, 9.26; N, 4.15. Found C, 63.82; H, 9.21; N, 4.06.

N-Butyl-2-[(tert-butyldimethylsilyl)oxy]-2-(2-furyl)acetamide

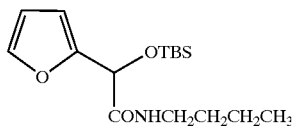

Colorless oil, FT-IR (CHCl$_3$): 3421, 2958, 2932, 1676, 1530, 1088, 841 cm$^{-1}$; $^1$H-NMR (300 MHz): 7.36 (s, 1H), 6.92 (br, —NH, 1H), 6.32 (brs, 2H), 5.21 (brs, 1H), 3.47–3.21 (m, 2H), 1.61–1.47 (m, 2H), 1.47–1.31 (m, 2H), 0.94 (t, J=7.2 Hz, 3H), 0.90 (s, 9H), 0.11 (s, 3H), 0.05 (s, 3H). $^{13}$C-NMR (75 MHz): 169.6, 152.1, 142.5, 110.4, 108.6, 69.7, 38.8, 31.6, 25.7, 20.0, 18.1, 13.7, –5.1, –5.5; EI-HRMS Calcd for C$_{12}$H$_{20}$NO$_3$Si (M-'Bu)$^+$: 254.1212, Found 254.1214.

N-Butyl-2-[(tert-butyldimethylsilyl)oxy]-2-(2-bromophenyl)acetamide

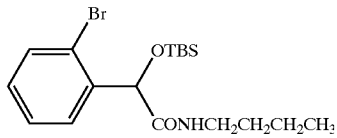

Colorless crystals, mp 38–39° C., FT-IR (CHCl$_3$): 3423, 2957, 2932, 1673, 1525, 1092, 870, 840 cm$^{-1}$; $^1$H-NMR (300 MHz): 7.54 (d, J=7.9 Hz, 1H), 7.19 (brd, J=7.9 Hz, 1H), 7.28 (t, J=7.9 Hz, 1H), 7.13 (brt, J=7.9 Hz, 1H), 6.92 (br, —NH, 1H), 5.57 (s, 1H), 3.39–3.16 (m, 2H), 1.59–1.45 (m, 2H), 1.45–1.28 (m, 2H), 0.93 (t, J=7.3 Hz, 3H), 0.91 (s, 9H), 0.10 (s, 3H), –0.11 (s, 3H). $^{13}$C-NMR (75 MHz): 170.8, 139.8, 132.8, 129.4, 128.3, 127.4, 123.4, 74.2, 38.5, 31.5, 25.6, 19.9, 17.9, 13.6, –4.9, –5.4; Anal. Calcd for C$_{18}$H$_{30}$BrNO$_2$Si: C, 53.99; H, 7.55; N, 3.50. Found: C, 53.86; H, 7.60; N, 3.48.

N-Butyl-2-[(tert-butyldimethylsilyl)oxy]-2-(4-cyanophenyl)acetamide

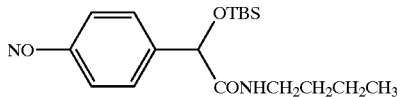

Colorless oil, FT-IR (CHCl$_3$): 3423, 2957, 2933, 2232, 1673, 1525, 1094, 866, 841 cm$^{-1}$; $^1$H-NMR (300 MHz): 7.63 (d, J=8.8 Hz, 2H), 7.59 (d, J=8.8 Hz, 2H), 6.75 (br, —NH, 1H), 5.11 (s, 1H), 3.41–3.23 (m, 1H), 3.23–3.05 (m, 1H), 1.54–1.41 (m, 2H), 1.41–1.24 (m, 2H), 0.95 (s, 9H), 0.91 (t, J=7.2 Hz, 3H), 0.10 (s, 3H), 0.00 (s, 3H). $^{13}$C-NMR (75 MHz): 170.5, 145.0, 131.9, 126.6, 118.6, 111.6, 74.8, 38.6, 31.4, 25.5, 19.8, 18.0, 13.5, –5.0, –5.5; EI-HRMS Calcd for C$_{19}$H$_{31}$N$_2$O$_2$Si (MH)$^+$: 347.21, Found 347.2164.

(3E)-N-Butyl-2-[(tert-butyldimethylsilyl)oxy]-4-phenyl-but-3-enamide

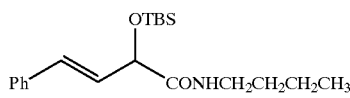

Colorless oil, FT-IR (CHCl$_3$): 3422, 2958, 2932, 1670, 1526, 1258, 1128, 839 cm$^{-1}$; $^1$H-NMR (300 MHz): 7.45–7.18 (m, 5H), 6.70 (d, J=15.6Hz, 1H), 6.65 (br, —NH, 1H), 6.31 (dd, J=15.6 and 4.8 Hz, 1H), 4.76 (d, J=4.8 Hz, 1H), 3.45–3.28 (m, 1H), 3.28–13.09 (m, 1H), 1.59–1.43 (m, 2H), 1.43–1.27 (m, 2H), 0.98 (s, 9H), 0.93 (t, J=7.2Hz, 3H), 0.14 (s, 3H), 0.13 (s, 3H). $^{13}$C-NMR (75 MHz): 171.5, 136.4, 130.5, 128.5, 127.8, 127.7, 126.6, 74.4, 38.6, 31.6, 25.8, 20.0, 18.2, 13.7, –4.7, –5.4; EI-HRMS Calcd for C$_{20}$H$_{33}$NO$_2$Si (M$^+$): 347.2281, Found 347.2250.

(3E)-N-Butyl-2-[(tert-butyldimethylsilyl)oxy]-pent-3-enamide

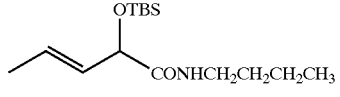

Colorless oil, FT-IR (CHCl$_3$): 3421, 2958, 2932, 1665, 1526, 1259, 840 cm$^{-1}$; $^1$H-NMR (300 MHz): 6.64 (br, —NH, 1H), 5.78 (dqd, J=15.6, 6.3, 1.3 Hz, 1H), 5.53 (ddd, J=15.6, 6.0 and 1.5 Hz, 1H), 4.50 (brd, J=6.0 Hz, 1H), 3.41–3.25 (m, 1H), 3.25–3.10 (m, 1H), 1.71 (brd, J=6.3 Hz, 3H), 1.57–141.43 (m, 2H), 1.43–1.24 (m, 2H), 0.927 (s, 9H), 0.926 (t, J=7.2 Hz, 3H), 0.09 (s, 6H). $^{13}$C-NMR (75 MHz): 172.1, 129.3, 127.7, 74.5, 38.5, 31.5, 25.6, 19.9, 18.0, 17.5, 13.6, –4.7, –5.4; EI-HRMS Calcd for C$_{15}$H$_{31}$NO$_2$Si (M$^+$): 285.2124, Found 285.2105.

N-Butyl-2-[(tert-butyldimethylsilyl)oxy]-4-phenylbutanamide

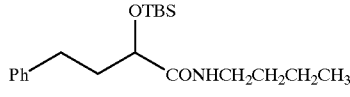

Colorless oil, FT-IR (CHCl$_3$): 3424, 2958, 2931, 1665, 1530, 1104, 839 cm$^{-1}$; $^1$H-NMR (300 MHz): 7.34–7.21 (m, 2H), 7.24–17.13 (m, 3H), 6.64 (br, —NH, 1H), 4.22 (t, J=4.8 Hz, 1H), 3.40–3.15 (m, 2H), 2.76–2.52 (m, 2H), 2.20–1.89 (m, 2H), 1.56–1.43 (m, 2H), 1.43–1.27 (m, 2H), 0.96 (s, 9H), 0.94 (t, J=7.5 Hz, 3H), 0.13 (s, 3H), 0.09 (s, 3H). $^{13}$C-NMR (75 MHz): 173.2, 141.7, 128.41, 128.36, 125.8, 73.1, 38.5, 37.1, 31.7, 30.5, 25.7, 20.1, 18.0, 13.7, −4.8, −53; EI-HRMS Calcd for $C_{16}H_{26}NO_2Si$ (M-'Bu)$^+$: 292.1733, Found 292.1745.

N-n-Butyl-2-[(tert-butyldimethylsilyl)oxy]-3-ethylheptanamide

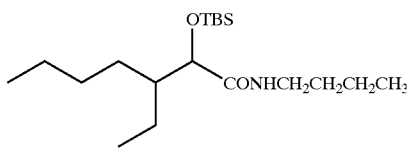

Colorless oil, FT-IR (CHCl$_3$): 3428, 2960, 2932, 1661, 1526, 1465, 1256, 1079, 839 cm$^{-1}$; $^1$H-NMR (300 MHz): 6.53 (br, —NH, 1H), 4.13 (d, J=2.4 Hz 1H), 3.37–3.19 (m, 2H), 1.71–1.53 (m, 2H), 1.53–1.16 (m, 10H), 0.94 (s, 9H), 1.07–0.80 (m, 6H), 0.90 (t, J=7.5 Hz, 3H), 0.09 (s, 3H), 0.05 (s, 3H). $^{13}$C-NMR (75 MHz): 173.4 and 173.4, 75.1 and 75.0, 44.8 and 44.5, 38.4 and 38.4, 31.6 and 31.6, 29.75 and 29.73, 29.4 and 28.5, 25.7 and 25.7, 23.05 and 23.01, 22.8 and 21.8, 20.0 and 20.0, 17.9 and 17.9, 13.97 and 13.92, 13.6 and 13.6, 12.2 and 12.0, −4.95 and −4.97, −5.2 and −5.2; EI-HRMS Calcd for $C_{15}H_{32}NO_2Si$ (M-'Bu)$^+$: 286.2202, Found 286.2205.

N-n-Butyl-2-[(Tert-butyldimethylsilyl)oxy]-3,3-diphenylpropanamide

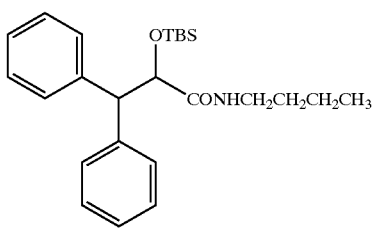

Colorless crystals, mp 73–74° C., FT-IR (KBr): 3280, 2960, 2940, 1654, 1570, 1110, 850 cm$^{-1}$; $^1$H-NMR (300 MHz): 7.52 (d, J=7.5 Hz, 2H), 7.35 (d, J=7.5 Hz, 2H), 7.32–7.14 (m, 6H), 6.19 (br, —NR, 1H), 4.64 (d, J=3.9 Hz, 1H), 4.54 (d, J=3.9 Hz, 1H), 3.12–2.98(m, 1H), 2.98–2.84(m, 1H), 1.16–0.96(m, 4H), 0.88(s, 9H), 0.77(t, J=6.4 Hz, 3H), −0.14(s, 3H), −0.45 (s, 3H). $^{13}$C-NMR(75 Mz): 171.2, 141.3, 138.8, 130.4, 129.0, 128.2, 128.0, 126.9, 126.5, 78.8, 54.9, 38.4, 31.3, 25.8, 19.8, 18.0, 13.6, −5.6, −6.0; Anal. Calcd for $C_{25}H_{37}NO_2Si$: C, 72.94; H, 9.06; N, 3.40. Found: C, 72.78; H, 9.06; N, 3.43.

N-Butyl-2-[(tert-butyldimethylsilyl)oxy]-3,3-dimethylbutanamide

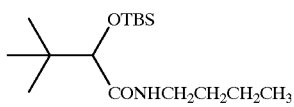

Colorless crystals, mp 41–42°C., FT-IR (CHCl$_3$): 3431, 2959, 2932, 1661, 1525, 1087, 868, 840 cm$^{-1}$; $^1$H-NMR (300 MHz): 6.30 (br, —NH, 1H), 3.72 (s, 1H), 3.25 (dt, J=6.6, 6.6 Hz, 2H), 1.56–1.28 (m, 4H), 0.95 (s, 18H), 0.93 (t, J=7.5 Hz, 3H), 0.08 (s, 3H), 0.03 (s, 3H). $^{13}$C-NMR (75 MHz): 172.2, 81.2, 38.4, 35.2, 31.8, 26.2, 25.8, 20.2, 18.0, 13.7, −5.16, −5.18; Anal. Calcd for $C_{16}H_{35}NO_2Si$: C, 63.73; H, 11.70; N, 4.64. Found: C, 63.38; H, 11.57; N, 4.74.

N-Butyl-2-[(tert-butyldimethylsilyl)oxy]-2-(4-methylphenyl)propanamide

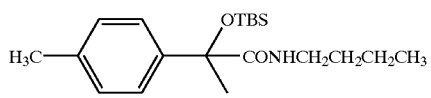

Colorless oil, FT-IR (CHCl$_3$): 3425, 2958, 2932, 1666, 1520, 1261, 1139, 985, 839 cm$^{-1}$; $^1$H-NMR (300 MHz): 7.34 (d, J=7.8 Hz, 2H), 7.11 (d, J=7.8 Hz, 2H), 6.98 (br, —NH, 1H), 3.30–3.12 (m, 2H), 2.31 (s, 3H), 1.84 (s, 3H), 1.56–1.42 (m, 2H), 1.42–1.23 (m, 2H), 0.97 (s, 9H), 0.91 (t, J=7.5 Hz, 3H), 0.08 (s, 3H), −0.16 (s, 3H). $^{13}$C-NMR (75 MHz): 174.9, 141.0, 137.2, 128.8, 125.5, 79.4, 39.0, 31.6, 26.0, 25.9, 21.0, 20.0, 18.3, 13.7, 31 2.4, 31 3.0; EI-HRMS Calcd for $C_{16}H_{26}NO_2Si$ (M-tBu)+: 292.1733, Found 292.1706.

N-Butyl-2-[(tert-butyldimethylsilyl)oxy]-2-(4-nitrophenyl)propanamide

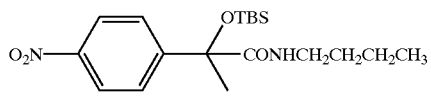

Colorless crystals, mp 49–50° C., FT-IR (CHCl$_3$): 3429, 2958, 2933, 1673, 1524, 1263, 1145, 985, 862, 838 cm$^{-1}$; $^1$H-NMR (300 MHz): 8.18 (d, J=9.0 Hz, 2H), 7.68 (d, J=9.0 Hz, 2H), 6.91 (br, —NH, 1H), 3.32–3.12 (m, 2H), 1.90 (s, 3H), 1.55–1.41 (m, 2H), 1.41–1.25 (m, 2H), 1.01 (s, 9H), 0.91 (t, J=7.5 Hz, 3H), 0.16 (s, 3H), −0.07 (s, 3H). $^{13}$C-NMR (75 MHz): 173.4, 151.5, 147.3, 126.5, 123.3, 79.3, 39.1, 31.5, 26.3, 26.0. 20.0, 18.3, 13.7, −2.3, −2.7; Anal. Calcd for $C_{19}H_{32}N_2O_4Si$: C, 59.97 H, 8.48; N, 7.36. Found: C, 59.83; H, 8.51; N, 7.35.

N-Butyl-[(tert-butyldimethylsilyloxy)cyclohexyl]carboxamide

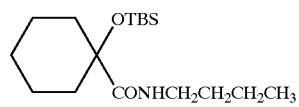

Colorless crystals, mp 47–48° C., FT-IR (CHCl$_3$): 3441, 2933, 1662, 1520, 1261, 838 cm$^{-1}$; $^1$H-NMR (300 MHz): 6.37 (br, —NH, 1H), 3.21 (dt, J=6.2, 6.2 Hz, 2H), 2.00–1.83 (m, 2H), 1.78–1.25 (m, 12H), 0.93 (s, 9H), 0.92 (t, J=7.5 MHz, 3H), 0.13 (s, 3H), 0.00 (s, 3H). $^{13}$C-NMR (75 MHz): 176.4, 77.9, 38.8, 36.5, 31.6, 25.9, 253, 22.2, 20.1, 18.4, 13.7, −2.4; Anal. Calcd for $C_{17}H_{35}NO_2Si$: C, 6.12; H, 11.2; N, 4.47. Found: C, 64.81; H, 11.26; N, 4.50.

N-Butyl-2-ethyl-2-[(tert-butyldimethylsilyl)oxy]-butanamide

Colorless oil, FR-IR (CHCl$_3$): 3424, 2957, 2932, 1657, 1525, 1260, 1162, 1020, 838 cm$^{-1}$; $^1$H-NMR (300 MHz): 6.94 (br, 1H), 3.26 (dt, J=6.4, 6.4 Hz, 2H), 2.00 (dq, J=14.8 and 7.4 Hz, 2H), 1.58–1.28 (m, 6H), 1.01 (s, 9H), 0.95 (t, J=7.5 Hz, 3H), 0.85 (t, J=7.4 Hz, 6H), 0.21 (s, 6H). $^{13}$C-NMR (75 MHz): 174.2, 84.1, 38.6, 32.8, 31.7, 26.2, 20.0, 18.6, 13.7, 8.3, −2.4; EI-HRMS Calcd for C$_{12}$H$_{26}$NO$_2$Si (M−tBu)+: 244.1733. Found 244.1770.

2-[(tert-butyldimethylsilyl)oxy]-2-(4-methylphenyl)acetamide

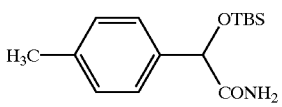

Colorless crystals, mp 108–110° C., FT-IR (CHCl$_3$): 3523, 3405, 1691, 1561, 1092, 868, 840 cm$^{-1}$; $^1$H-NMR (300 MHz): 7.33 (d, J=7.8 Hz, 2H), 7.14 (d, J=7.8 Hz, 2H), 6.73 (br, —NH, 1H), 5.62 (br, —NH, 1H), 5.03 (s, 1H), 2.33 (s, 3), 0.92 (s, 9H), 0.09 (s, 3H), −0.05 (s, 3H). $^{13}$C-NMR (75 MHz): 176.0, 137.8, 136.7, 129.0, 126.3, 75.6, 25.7, 21.2, 18.1, −4.8, −5.3; Anal. Calcd for C$_{15}$H$_{25}$NO$_2$Si: C, 64.47; H, 9.02; N, 5.01. Found: C, 64.36; H, 8.99; N, 4.99.

N-Hydroxy-2-[(tert-butyldimethylsilyl)oxy]-2-(4-methylphenyl)acetamide

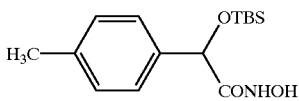

Colorless crystals, mp 109–111° C. (unstable at room temperature), FT-IR (CHCl$_3$): 3428, 3170 (br), 2956, 2931, 1677, 1257, 1094, 861, 841 cm$^{-1}$; $^1$H-NMR (300 MHz): 9.07 (s, —OH, 1H), 7.90 (br, —NH, 1H), 7.27 (d, J=7.8 Hz, 2H), 7.13 (d, J=7.8 Hz, 2H), 5.12 (s, 1H), 2.33 (s, 3H), 0.89 (s, 9H), 0.06 (s, 3H), −0.10 (s, 3H). $^{13}$C-NMR (75 MHz): 169.9, 138.2, 135.9, 129.1, 126.6, 75.2, 25.7, 21.2, 18.0, −4.9, −5.3; EI-HRMS Calcd for C$_{11}$H$_{16}$NO$_3$Si (M−$^t$Bu)$^+$: 238.0899, Found 238.0917.

N-Phenyl-2-[(tert-butyldimethylsilyl)oxy]-2-(4-methylphenyl)acetamide

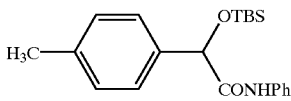

Colorless oil, FT-IR (CHCl$_3$): 3386, 3023, 2955, 2931, 1689, 1602, 1526, 1445, 1091, 881, 842 cm$^{-1}$; $^1$H-NMR (300 MHz): 8.68 (s, —NH, 1H), 7.54 (d, J=7.9 Hz, 2H), 7.37 (d, J=7.9 Hz, 2H), 7.32 (t, J=7.9 Hz, 2H), 7.15 (d, J=7.9 Hz, 2H), 7.09 (t, J=7.9 Hz, 1H), 5.14 (s, 1H), 2.33 (s, 3H), 0.99 (s, 9H), 0.14 (s, 3H), 0.00 (s, 3H). $^{13}$C-NMR (75 MHz): 170.1, 137.9, 137.4, 136.4, 129.1, 129.0, 126.2, 124.3, 119.3, 75.9, 25.8, 21.1, 18.1, −4.7, −5.3; EI-HRMS Calcd for C$_{17}$H$_{20}$NO$_2$Si (M−$^t$Bu)$^+$: 298.1263, Found 298.1283.

N-Methoxycarbonylmethyl-2-[(tert-butyldimethylsilyl)oxy]-2-(4-methylphenyl)acetamide

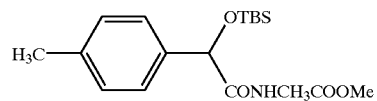

Colorless oil, FT-IR (CHCl$_3$): 3418, 2956, 2931, 1747, 1678, 1511, 1256, 1235, 1093, 866, 840 cm$^{-1}$; $^1$H-NMR (300 MHz): 7.36 (br, —NH, 1H), 7.33 (d, J=7.8 Hz, 2H), 7.13 (d, J=7.8 Hz, 2H), 5.08 (s, 1H), 4.16 (dd, J=18.9 and 5.7 Hz, 1H), 3.93 (dd, J=18.9 and 5.7 Hz, 1H), 3.76 (s, 3H), 2.32 (s, 3H), 0.95 (s, 9H), 0.11 (s, 3H), −0.04 (s, 3H). $^{13}$C-NMR (75 MHz): 172.5, 170.1, 137.8, 136.6, 129.0, 126.2, 75.5, 52.3, 40.8, 25.7, 21.2, 18.1, −4.8, −5.3; EI-HRMS Calcd for C$_{18}$H$_{29}$NO$_4$Si (M$^+$): 351.1866, Found 351.1874.

N-(2-Hydroxy)ethyl-2-[(tert-butyldimethylsilyl)oxy]-2-(4-methylphenyl)acetamide

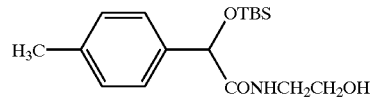

Colorless crystals, mp 69–70° C., FT-IR (CHCl$_3$): 3422, 3270 (br), 2931, 1669, 1536, 1256, 1093, 867, 840 cm$^{-1}$; $^1$H-NMR (300 MHz): 7.32 (d, J=7.8 Hz, 2H), 7.13 (d, J=7.8 Hz, 2H), 5.06 (s, 1H), 4.72 (s, 1H), 3.71 (dt, J=5.0 and 5.0 Hz, 2H), 3.55–3.31 (m, 2H), 2.46 (t, J=5.4 Hz, —OH, 1H), 2.33 (s, 3H), 0.93 (s, 9H), 0.09 (s, 3H), 310.04 (s, 3H). $^{13}$C-NMR (75 MHz): 173.6, 137.8, 136.8, 129.1, 126.2, 75.7, 62.1, 41.9, 25.8, 21.2, 18.2, −4.7, −5.3; Anal. Calcd for C$_{17}$H$_{29}$NO$_3$Si: C, 63.12; H, 9.04; N, 4.33. Found: C, 62.88; H, 8.97; N, 4.33.

N-((1R)-1-phenylethyl)-2-[(tert-butyldimethylsilyl)oxy]-2-(4-methylphenyl)acetamide

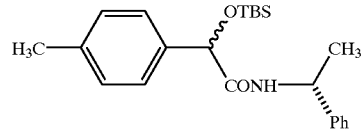

Colorless oil, FT-IR (CHCl$_3$): 3413, 2955, 2931, 1669, 1510, 1089, 865, 840 cm$^{-1}$; $^1$H-NMR (300 MHz): 7.40–7.01 (m, 9H), 5.15–5.00 (m, 1H), 5.07 and 5.01(s, 1H), 2.33 and 2.31 (s, 3H), 1.52 and 1.44 (d, J=6.8 Hz, 3H), 0.94 and 0.85 (s, 9H), 0.11, −0.01, −0.03 and −0.08 (s, 6H). $^{13}$C-NMR (75 MHz): 171.3 and 171.2, 143.1 and 143.0, 137.6 and 137.6, 136.8 and 136.7, 128.99 and 128.96, 128.62 and 128.59, 127.36 and 127.19, 126.10 and 126.07, 126.04 and 125.84, 75.6 and 75.5, 48.3 and 48.0, 25.7 and 25.6, 22.1 and 21.7, 21.15 and 21.12, 18.1 and 18.0, −4.76 and −4.84, −5.37 and −5.46; EI-HRMS Calcd for C$_{19}$H$_{24}$NO$_2$Si (M−$^t$Bu)$^+$: 326.1576, Found 326.1579.

N,N-Diethyl-2-[(tert-butyldimethylsilyl)oxy]-2-(4-methylphenyl)acetamide

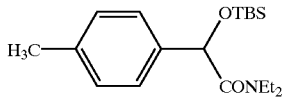

Colorless oil, FT-IR (CHCl₃): 2958, 2932, 1631, 1464, 1256, 1098, 869, 840 cm⁻¹; ¹H-NMR (300 MHz): 7.31 (d, J=8.1 Hz, 2H), 7.14 (d, J=8.1 Hz, 2H), 5.49 (s, 1H), 3.54–3.37 (m, 2H), 3.24–3.05 (m, 2H), 2.33 (s, 3H), 1.08 (t, J=6.9 Hz, 3H), 0.97 (s, 9H), 0.68 (t, J=6.9 Hz, 3H), 0.13 (s, 6H). ¹³C-NMR (75 MHz): 171.0, 136.9, 136.7, 129.0, 124.8, 77.7, 40.3, 39.8, 25.9, 21.1, 18.4, 13.2, 12.4, −4.8, −5.2; EI-HRMS Calcd for $C_{15}H_{24}NO_2Si$ (M−'Bti)⁺: 278.1576, Found 278.1566.

2-[(tert-Butyldimethylsilyl)oxy]-2-(4-methylphenyl)-1-morpholin-4-ylethan-1-one

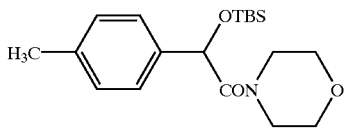

Colorless crystals, mp 64–65° C., FT-IR (CHCl₃): 2958, 2930, 1636, 1463, 1252, 1113, 866, 841 cm⁻¹; ¹H-NMR (300 MHz): 7.31 (d, J=8.0 Hz, 2H), 7.15 (d, J=8.0 Hz, 2H), 5.52 (s, 1H), 3.73–3.28 (m, 7H), 3.17–2.97 (m, 1H), 2.34 (s,3H), 0.98 (s, 3H), 0.150 (s, 3H), 0.145 (s, 3H). ¹³C-NMR (75 MHz): 170.5, 137.1, 136.0, 129.2, 124.4, 77.6, 66.7, 66.4, 45.6, 42.7, 25,8, 21.1, 18.3, −4.9, −5.4; Annl. Calcd for $C_{19}H_{31}NO_3Si$: C, 65.29; H, 8.94; N, 4.01. Found: C, 65.03; H, 8.82; N, 4.00.

N-Methoxy-N-methyl-2-[(tert-butyldimethylsilyl)oxy]-2-(4-methylphenyl)acetamide

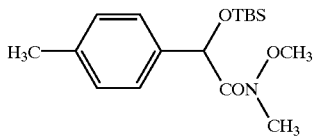

Colorless oil, FT-IR (CHCl₃): 2931, 1670, 1255, 1086, 999, 867, 840 cm⁻; ¹H-NMR (300 MHz): 7.32 (d, J=8.0 Hz, 2H), 7.13 (d, J=8.0 Hz, 2H), 5.55 (s, 1H), 3.51 (s, 3H), 3.13 (s, 3H), 2.33 (s, 3H), 0.91 (s, 9H), 0.12 (s, 3H), 0.00 (s, 3H). ¹³C-NMR (75 MHz at 55° C.): 172.7, 137.5, 136.7, 129.0, 126.8, 73.6, 60.7, 33.3, 25.9, 21.1, 18.4, −4.8, −5.0. Anal. Calcd for $C_{17}H_{29}NO_3Si$: C, 63.12; H, 9.04; N, 4.33. Found: C, 62.75; H, 8.92; N, 4.28.

A Representative Procedure for One-pot Synthesis of α-hydroxyamides

To a solution of p-tolualdehyde (131 mg, 1.0 mmol) and 1 (216 mg, 1.2 mmol) in acetonitrile (3 ml) was added n-butylamine (80 mg, 1.1 mmol) at 0° C. After stirring for 5 min, the reaction mixtures was added dropwise THF solution of tetrabutylammonium fluoride (1.0 N, 1.5 ml, 1.5 mmol), and then stirred at 0° C. for 20 min. The resulting reaction solution was concentrated and purified with silica gel column chromatography by using hexane-ethyl acetate (3/1) as an eluent to give N-butyl-2-hydroxy-2-(4-methylphenyl)acetamide as a colorless powder (218 mg, 0.94 mmol, 94%).

N-Butyl-2-hydroxy-2-(4-methylphenyl)acetamide

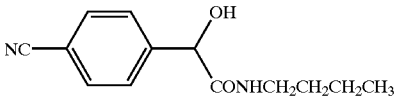

mp 55–57° C.; FT-IR (CHCl₃): 3426, 3360 (br), 2963, 2232, 1677, 1531 cm⁻¹; ¹H-NMR (300 MHz): 7.62 (d, J=8.0 Hz, 2H), 7.54 (d, J=8.0 Hz, 2H), 6.65 (br, 1H), 5.05 (s, 1H), 4.40 (br, —OH, 1H), 3.20 (dt, J=6.8, 6.8 Hz, 2H), 1.52–1.37 (m, 2H), 1.35–1.17 (m, 2H), 0.89 (t, J=7.2 Hz, 3H). ¹³C-NMR (75 MHz): 171.0, 144.9, 132.3, 127.2, 118.6, 111.9, 73.3, 39.2, 31.4, 19.9, 13.7; Anal. Calcd for $C_{13}H_{16}N_2O_2$: C, 67.22; H, 6.94; N, 12.06. Found: C, 67.14; H, 6.88; N, 11.94.

A Typical Procedure for the Synthesis of α-silyloxyesters

A mixture of p-tolualdehyde (120 mg, 1.0 mmol), 1 (216 mg, 1.1 mmol) and pyridine (79 mg, 1.0 mmol) in methanol (5 ml) was stirred for 2 h and then concentrated in vacuo. The residue was purified with silica gel column chromatography by using hexane-ethyl acetate (20/1) as an eluent to give methyl α-[(tert-butyldimethylsilyl)oxy]-2-(4-methylphenyl)acetate as a colorless oil (268 mg, 0.91 mmol, 91% yield).

Methyl 2-[tert-butyldimethylsilyl)oxy]-2-(4-methylphenyl)acetate

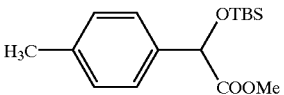

Colorless oil; FT-IR (CHCl₃): 2955, 2931, 2859, 1753, 1256, 1131, 840 cm⁻¹; ¹H NMR (400 MHz): 7.35 (d, J=8.0 Hz, 2H), 7.14 (d, J=8.0 Hz, 2H), 5.20 (s, 1H), 3.67 (s, 3H), 2.34 (s, 3H), 0.91 (s, 9H), 0.10 (s, 3H), 0.03 (s, 3H). ¹³C NMR (100 MHz): 172.7, 137.8, 136.2, 129.0, 126.3, 74.3, 52.1, 25.7, 21.2, 18.3, −5.10, −5.13; EL-HRMS Calcd for $C_{16}H_{27}O_3Si$ (MH⁺): 295.1729. Found 295.1725.

Methyl 2-[(tert-butyldimethylsilyl)oxy]-2-(2-hydroxyphenyl)acetate

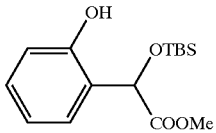

Colorless crystals, mp 103–104° C.; FT-IR (CHCl₃): 3397, 2956, 2932, 1751, 1244, 1100, 841 cm⁻¹; ¹H NMR (300 MHz): 7.79 (s, 1H), 7.21 (dd, J=7.6, 7.6 Hz, 1H), 7.13 (d, J=7.6 Hz, 1H), 6.88 (d, J=7.6 Hz, 1H), 6.85 (dd, J=7.6, 7.6 Hz, 1H), 5.24 (s, 1H), 3.72 (s, 3H), 0.92 (s, 9H), 0.15 (s, 3H), 0.07 (s, 3H). ¹³C NMR (75 MHz): 172.0, 155.9, 130.0, 128.3, 122.4, 119.8, 117.5, 75.1, 52.6, 25.5, 18.1, −5.3, −5.5; Anal. Calcd for $C_{15}H_{24}O_4Si$: C, 60.78; H, 8.16. Found: C, 60.57; H,8.23.

Methyl 2-[(tert-butyldimethylsilyl)oxy]-2-(2-furyl)acetate

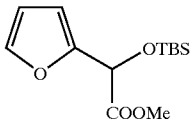

Colorless oil; FT-IR (CHCl$_3$): 2956, 2932, 2859, 1757, 1260, 1153, 1119, 841 cm$^{-1}$; $^1$H NMR (400 MHz): 7.39 (s, 1H), 6.34 (s, 2H), 5.28 (s, 1H), 3.77 (s, 3H ), 0.90 (s, 9H), 0.11 (s, 3H), 0.04 (s, 3H). $^1$C NMR (100 MHz): 170.6, 151.6, 142.6, 110.4, 108.1, 68.7, 52.4, 25.6, 18.4, −5.2, −5.3; EI-MS: 271 (MH$^+$).

Methyl 2-[(tert-butyldimethylsilyl)oxy]-2-(4-cyanophenyl)acetate

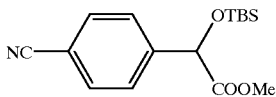

Colorless oil; FT-IR (CHCl$_3$): 2955, 2932, 2860, 2232, 1757, 1261, 1136, 841, 796 cm$^{-1}$; $^1$H NMR (300 MHz): 7.65 (d, J=8.81 Hz, 2H), 7.60 (d, J=8.8 Hz, 2H), 5.27 (s, 1H), 3.70 (s, 3H), 0.92 (s, 9H), 0.13 (s, 3H), 0.06 (s, 3H). $^{13}$C NMR (75 MHz): 171.4, 144.1, 132.1, 126.9, 118.5, 111.9, 73.7, 52.4, 25.5, 18.2, −5.2, −5.4; EI-HRMS Calcd for C$_{16}$H$_{24}$NO$_3$Si (MH$^+$): 306.1525. Found 306.1502.

Methyl (3E)-2-[(tert-butyldimethylsilyl)oxy]-4-phenylbut-3-enoate

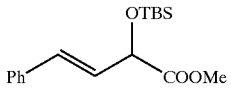

Colorless oil; FT-IR (CHCl$_3$): 2955, 2931, 2859, 1752, 1472, 1259, 1152, 839 cm$_{-1}$; $^1$H NMR (400 MHz): 7.39 (d, J=7.3 Hz, 2H), 7.32 (dd, J=7.3, 7.3 Hz, 2H), 7.24 (dd, J=7,3, 7.3 Hz, 1H), 6.75 (d, J=15.6 Hz, 1H), 6.31 (dd, J=15.6, 5.6 Hz, 2H), 4.89 (d, J=5.6 Hz, 1H), 3.75 (s, 3H), 0.95 (s, 9H), 0.15 (s, 3H), 0.12 (s, 3H). $^{13}$C NMR (100 MHz): 172.3, 136.4, 131.6, 128.6, 127.9, 126.7, 126.6, 73.2, 52.2, 25.8, 18.5, −5.0, −5.1; EI-HRMS Calcd for C$_{17}$H$_{27}$O$_3$Si (MH$^+$): 307.1729. Found 307.1766.

Methyl (3E)-2-[(tert-butyldimethylsilyl)oxy]pent-3-enoate

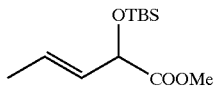

Colorless oil; FT-IR (CHCl$_3$): 2955, 2931, 2859, 1751, 1257, 1156, 840 cm$^{-1}$; $^1$H NMR (400 MHz): 5.83 (dqd, J=15.1, 6.8, 1.5 Hz, 1H), 5.57 (ddq, J=15.1, 5.8, 1.5 Hz, 1H), 4.66 (brd, J=5.8 Hz, 1H), 3.73 (s, 3H), 1.72 (ddd, J=6.8, 1.5, 1.5 Hz, 3H), 0.91 (s, 9H), 0.10 (s, 3H), 0.07 (s, 3H). $^{13}$C NMR (100 MHz): 172.8, 128.3, 128.3, 73.1, 52.0, 25.8, 18.4, 17.6, −5.0, −5.1; EI-HRMS Calcd for C$_{12}$H$_{25}$O$_3$Si (MH$^+$): 245.1573. Found 245.1596.

Methyl 2-[(tert-butyldimethylsilyl)oxy]-4-phenylbutanoate

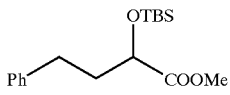

Colorless oil; FT-IR (CHCl$_3$): 2955, 2931, 2859, 1751, 1259, 1132, 839 cm$^{-1}$; $^1$H NMR (400 MHz): 7.32–7.25 (m, 2H), 7.20–7.13 (m, 3H), 4.26 (t, J=5.8 Hz, 1H), 3.70 (s, 3H), 2.80–2.64 (m, 2H), 2.10–1.98 (m, 2H), 0.93 (s, 9H), 0.09 (s, 3H), 0.07 (s, 3H). $^{13}$C NMR (100 MHz): 174.0, 141.5, 128.4, 128.4, 128.3, 125.9, 71.7, 51.8, 36.9, 31.4, 25.8, 18.4, −4.9, −5.3; EI-HRMS Calcd for C$_{17}$H$_{29}$O$_3$Si (MH$^+$): 309.1886. Found 309.1847.

Methyl 2-[(tert-butyldimethylsilyl)oxy]-3-methylbutanoate

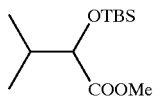

Colorless oil; FT-IR (CHCl$_3$): 2960, 2932, 2859, 1748, 1259, 1146, 838 cm$^{-1}$; $^1$H NMR (300 MHz): 3.97 (d, J=5.0 Hz, 1H), 3.71 (s, 3H), 2.13–1.94 (m, 1H), 0.93 (d, J=7.0 Hz, 3H), 0.91 (s, 9H), 0.90 (d, J=7.0 Hz, 3H), 0.05 (s, 3H), 0.04 (s, 3H). $^{13}$C NMR (75 MHz): 174.0, 77.1, 51.5, 32.9, 25.7, 19.0, 18.3, 17.0, −5.0, −5.4; EI-HRMS Calcd for C$_8$H$_{17}$O$_3$Si (M−$^t$Bu)$^+$: 189.0947. Found 189.0952.

Methyl 2-[(tert-butyldimethylsilyl)oxy]-3,3-dimethylbutanoate

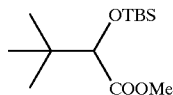

Coloress oil; FT-IR (CHCl$_3$): 2957, 2859, 1747, 1260, 1230, 1122, 839 cm$^{-1}$; $^1$NMR (400 MHz): 3.83 (s, 1H), 3.69 (s, 3H), 0.94 (s, 9H), 0.91 (s, 9H), 0.03 (s, 3H), 0.00 (s, 3H). $^{13}$C NMR (100 MHz): 173.2, 80.1, 51.1, 35.3, 2.59, 25.7, 18.2, −5.3, −5.5; EI-HRMS Calcd for C$_9$H$_{19}$O$_3$Si (M−$^t$Bu)$^+$: 203.1103. Found 203.1087.

Methyl 2-[(tert-butyldimethlylsilyl)oxy]-2-(4-methylphenyl)propanate

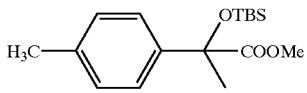

Colorless oil; FT-IR (CHCl$_3$): 2955, 2931, 1735, 1261, 1163, 1122, 1006, 839 cm$^{-1}$; $^1$H NMR (400 MHz): 7.40 (d, J=8.0 Hz, 2H), 7.13 (d, J=8.0 Hz, 2H), 3.65 (s, 3H), 2.33 (s, 3H), 1.78 (s, 3H), 0.96 (s, 9H), 0.12 (s, 3H), 0.07 (s, 3H). $^{13}$C NMR (100 MHz): 174.9, 141.4, 137.1, 128.8, 124.9, 78.4, 52.1, 28.3, 25.9, 21.0, 18.5, −2.9, −3.5; EI-HRMS Calcd for C$_{13}$H$_{19}$O$_3$Si (M−$^t$Bu)$^+$: 251.1103. Found 251.1135.

Methyl 2-[(tert-butyldimethylsilyl)oxy]-2-phenylpropanoate

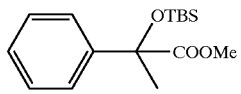

Colorless oil; FT-IR (CHCl$_3$): 2955, 2931, 2858, 1733, 1261, 1166, 839 cm$^{-1}$; $^1$H NMR (300 MHz): 7.58–7.47(m, 2H), 7.40–7.22 (m, 3H), 3.66 (s, 3H), 1.80 (s, 3H), 1.00 (s, 9H), 0.13 (s, 3H), 0.08 (s, 3H). $^{13}$C NMR (100 MHz): 174.8, 144.4, 128.1, 127.4, 125.0, 78.6, 52.2, 28.3, 25.9, 18.5, −2.8, −3.5; EI-HRMS Calcd for C$_{12}$H$_{17}$O$_3$Si (M−$^t$Bu)$^+$: 237.0947. Found 237.0937.

Methyl 2-[(tert-butyldimethylsilyl)oxy]-2-(4-nitrophenyl)propanoate

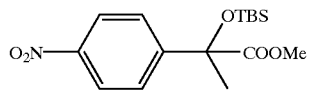

Colorless recrystals, mp 65–66° C.; FT-IR (CHCl$_3$): 2956, 1735, 1524, 1351, 1262, 1167, 840 cm$^{-1}$; $^1$H NMR (400 MHz): 8.18(d, J=8.8 Hz, 2H), 7.70 (d, J=8.8 Hz, 2H), 3.69 (s, 3H), 1.82 (s, 3H), 0.98 (s, 9H), 0.17 (s, 3H), 0.13 (s, 3H). $^{13}$C NMR (100 MHz): 173.6, 151.4, 147.4, 126.0, 123.4, 78.5, 52.60, 28.3, 25.8, 18.5, −2.8, −3.6; Anal. Calcd for C$_{14}$H$_{25}$NO$_5$Si: C, 56.61; H, 7.42; N, 4.13. Found: C, 56.55; H,7.50; N, 4.12.

Methyl 1-[(tert-butyldimethylsilyloxy)]cyclohex-2-enecarboxylate

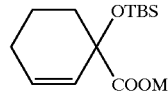

Colorless oil; FT-IR (CHCl$_3$): 2953, 2857, 1733, 1256, 1038, 838 cm$^{-1}$; $^1$H NMR (300 MHz): 5.94 (dt, J=10.2 and 3.6 Hz, 1H), 5.78 (brd, J=10.2 Hz, 1H), 3.72 (s, 3H), 2.20–1.60 (m, 6H), 0.87 (s, 9H), 0.09 (s, 3H), 0.05 (s, 3H). $^{13}$C NMR (75 MHz): 175.4, 131.5, 128.4, 74.0, 52.0, 34.7, 257, 24.8, 18.3, 18.2, −2.9, −3.0; EI-HRMS Calcd for C$_{14}$H$_{26}$O$_3$Si (M$^+$): 270.1651. Found 270.1642.

Methyl 3-{[(dicyano[(tert-butyldimethylsilyl)oxy]methyl}-1[(tert-butyldimethylsilyloxy)]cyclohexanecarboxylate

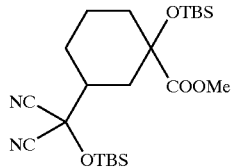

Colorless crystals, mp 71–73° C.; FT-IR (CHCl$_3$): 2956, 2246, 1740, 1257, 1139, 841 cm$^{-1}$; $^1$H NMR (300 MHz): 3.74 (s, 3H), 2.42 (tt, J=12.3, 3.4 Hz, 1H), 2.19 (brd, J=12.8 Hz, 1H), 2.04 (brd, J=12.3 Hz, 1H), 1.89 (brd, J=13.4 Hz, 1H), 1.85–1.72 (m, 2H), 1.72–1.54 (m, 2H), 1.36–1.17 (m, 1H), 0.93 (s, 9H), 0.91 (s, 9H), 0.36 (s, 6H), 0.09 (s, 3H), 0.09 (s, 3H). $^{13}$C NMR (75 MHz): 174.5, 114.7, 114.4, 75.9, 67.8, 52.2, 44.2, 35.7, 35.0, 26.0, 25.8, 2.2, 19.9, 18.7, 18.1, −3.4, −4.6, −4.6; Anal. Calcd for C$_{23}$H$_{42}$N$_2$O$_4$Si$_2$: C, 59.18; H, 9.07; N, 6.00. Found: C, 59.18; H,9.20; N, 5.97.

Methyl 1-[(tert-butyldimethylsilyloxy)]cyclohexanecarboxylate

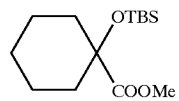

Colorless oil; FT-IR (CHCl$_3$): 2936, 2857, 1733, 1250, 1156, 1084, 1062, 839 cm$^{-1}$; $^1$H NMR (400 MHz): 3.70 (s, 3H), 1.86–1.74 (m, 2H), 1.74–1.60 (m, 4H), 1.57–1.42 (m, 3H), 1.35–1.23 (m, 1H), 0.90 (s, 9H), 0.06 (s, 6H). $^{13}$C NMR (100 MHz): 175.5, 76.5, 51.6, 36.0, 26.0, 25.3, 21.7, 18.6, −3.2; EI-HRMS Calcd for C$_{14}$H$_{29}$O$_3$Si (MH$^+$): 273.1886, Found 273.1872.

Methyl 2-[(tert-butyldimethylsilyl)oxy]-2-ethyl-butanoate

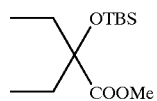

Colorless oil; FT-IR (CHCl$_3$): 2955, 2931, 1740, 1252, 1188, 1147, 1088, 838 cm$^{-1}$; $^1$H NMR (300 MHz): 3.70 (s, 3H), 1.84–1.60 (m, 4H), 0.89 (s, 9H), 0.85 (t, J=7.5 Hz, 6H), 0.12 (s, 6H). $^{13}$C NMR (75 MHz): 175.5, 81.7, 51.6, 32.2, 26.0, 18.8, 8.4, −2.7; EI-HRMS Calcd for C$_9$H$_9$O$_3$Si(M−$^t$Bu)$^+$: 203.1103. Found 203.1158.

n-Propyl 2-[(tert-butyldimethylsilyl)oxy]-2-(4-methylphenyl)acetate

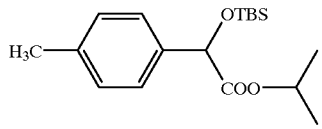

Colorless oil; FT-IR (CHCl$_3$): 2931, 2859, 1742, 1256, 1104, 874, 839 cm$^{-1}$; $^1$H NMR (400 MHz): 7.35 (d, J=8.0 Hz, 2H), 7.13 (d, J=8.0 Hz, 2H), 5.14 (s, 1H), 5.03–4.93 (m, 1H), 2.33 (s, 3H), 1.22 (d, J=6.4 Hz, 3H), 1.15 (d, J=6.4 Hz, 3H), 0.92 (s, 9H), 0.11 (s, 3H), 0.04 (s, 3H). $^{13}$C NMR (100 MHz): 171.9, 137.6, 136.5, 128.9, 126.2, 74.4, 68.4, 25.8, 21.7, 21.6, 21.2, 18.4, −5.0, −5.1; EI-HRMS Calcd for C$_{14}$H$_{21}$O$_3$Si (M−$^t$Bu)$^+$: 265.1260. Found 265.1271.

Benzyl 2-[(tert-butyldimethylsilyl)oxy]-2(4-methylphenyl)acetate

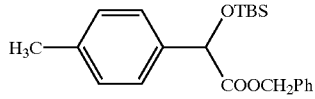

Colorless oil; FT-IR (CHCl$_3$): 2957, 2931, 1751, 1256, 1168, 1130, 867, 840 cm$^{-1}$; $^1$H NMR (400 MHz): 7.35 (d, J=8.0 Hz, 2H), 7.33–7.26 (m, 2H), 7.26–7.19 (m, 3H), 7.14 (d, J=8.0 Hz, 2H), 5.23 (s, 1H), 5.11 (s, 2H), 2.34 (s, 3H), 0.89 (s, 9H), 0.06 (s, 3H), 0.00 (s, 3H). $^{13}$C NMR (100 MHz): 172.1, 137.8, 136.1, 135.7, 129.0, 128.4, 128.1, 128.0, 126.4, 74.3, 66.6, 25.7, 21.2, 18.3, −5.1, −5.2; EI-HRMS Calcd for $C_{18}H_{21}O_3Si$ (M−$^t$Bu)$^+$: 313.1260. Found 313.1251.

Allyl 2-[(tert-butyldimethylsilyl)oxy]-2-(4-methylphenyl)acetate

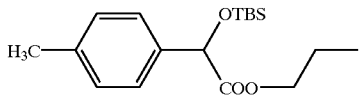

Colorless oil; FT-IR (CHCl$_3$): 2956, 2859, 1751, 1255, 1177, 864, 840 cm$^{-1}$; $^1$H NMR (400 MHz): 7.36 (d, J=8.0 Hz, 2H), 7.14 (d, J=8.0 Hz, 2H), 5.90–5.78 (m, 1H), 5.22 (s, 1H), 5.26–5.14 (m, 2H), 4.57 (dt, J=5.2, 1.2 Hz, 2H), 2.34 (s, 3H), 0.91 (s, 9H), 0.10 (s, 3H), 0.03 (s, 3H). $^{13}$C NMR (100 MHz): 172.0, 137.8, 136.2, 131.8, 129.0, 126.3, 118.2, 74.3, 65.5, 25.7, 21.2, 18.4, −5.0, −5.1; EI-HRMS Calcd for $C_{14}H_{19}O_3Si$ (M−$^t$Bu)±: 263.1103. Found 263.1096.

Phenyl 2-[(tert-butyldimethylsilyl)oxy]-2-(4-methylphenyl)acetate

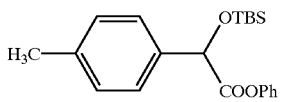

Colorless oil; FT-IR (CHCl$_3$): 2931, 1772, 1493, 1256, 1192, 1126, 872, 840 cm$^{-1}$; $^1$H NMR (400 MHz): 7.46 (d, J=8.0 Hz, 2H), 7.37–7.28 (m, 2H), 7.23–7.13 (m, 3H), 6.98 (d, J=8.0 Hz, 2H), 5.41(s, 1H), 2.36 (s, 3H), 0.95 (s, 9H), 0.17 (s, 3H), 0.09 (s, 3H). $^{13}$C NMR (100 MHz): 170.8, 150.7, 138.1, 135.8, 129.4, 129.2, 128.6, 125.8, 121.2, 74.4, 25.8, 21.2, 18.4, −5.0, −5.1; EI-HRMS Calcd for $C_{21}H_{29}O_3Si$ (MH$^+$): 357.1886. Found 357.1914.

[(tert-butyldimethylsilyl)oxy][hydroxy(4-methylphenyl)methyl]-1,1-dicarbonitrile

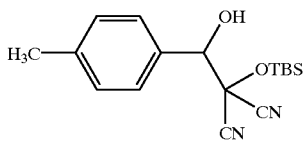

$^1$H NMR(300 MHz): 7.43 (d, J=8.0 Hz, 2H), 7.22 (d, J=8.0 Hz, 2H), 4.97 (s, 1H), 2.38 (s, 3H), 0.90 (s, 9H), 0.35 (s, 3H), 0.24 (s, 3H). $^{13}$C NMR (75 Hz): 139.8, 131.2, 129.0, 128.8, 114.6, 113.7, 78.4, 69.0, 25.2, 21.2, 18.0, −4.6, −4.8; EI-HRMS Calcd for $C_{17}H_{24}N_2O_2Si$ (M$^+$): 316.1607. Found 316.1611.

A Typical Procedure for One-pot Synthesis of α-hydroxyesters

A mixture of 4-cyanobenzaldehyde (131 mg, 1.0 mmol), H-MAC-TBS (216 mg, 1.1 mmol) and pyridine (79 mg, 1.0 mmol) in methanol was stirred for 2 h and then concentrated in vacuo. The residue was dissolved in THF (5 ml). To the solution was added dropwise TBAF (1.0 M solution in THF) (1.5 ml, 1.5 mmol) at 0° C. After stirring at 0° C. for additional 20 min, the reaction mixture was concentrated in vacuo and purified with silica gel column chromatography by using hexane-ethyl acetate (4/1) as an eluent to give methyl 2-hydroxy-2-(4-cyanophenyl)acetate as a white solid (168 mg, 0.88 mmol, 88% yield).

Methyl 2-hydroxy-2-(4-cyanophenyl)acetate

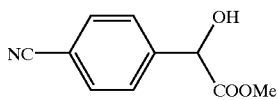

mp 51–52° C.; FT-IR (CHCl$_3$): 3528, 2928, 2233, 1738, 1256, 1088 cm$^{-1}$; $^1$H NMR(300 MHz): 7.67 (d, J=8.3 Hz, 2H), 7.58 (d, J=8.3 Hz, 2H), 5.24 (s, 1H), 3.79 (s, 3H), 3.57 (br, 1H). $^{13}$C NMR (75 MHz): 173.0, 143.1, 132.3, 127.3, 118.5, 112.3, 72.2, 53.4; Anal. Calcd for $C_{10}H_9NO_3$: C, 62.82; H, 4.74; N, 7.33. Found: C, 62.76; H,4.89; N, 7.33.

threo-Methyl 3-N-benzyloxycarbonylamino-2-(tert-butyldimethylsilyloxy)-4-phenylbutane

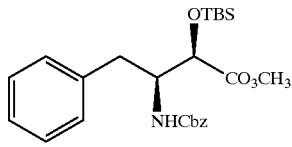

Colorless oil; FT-IR (CHCl$_3$): 3437, 2953, 1753, 1717, 1504, 1146, 840 cm$^{-1}$; $^1$H NMR (300 MHz): 7.40–7.10 (m. 10H), 5.17 (brd, J=8.5 Hz, NH), 5.01 (d, J=12.3 Hz, 1H), 4.97 (d, J=12.3 Hz, 1H), 4.41–4.29 (m, 1H), 4.23 (d, J=1.4 Hz, 1H), 3.64 (s, 3H), 2.87 (d, J=7.5 Hz, 2H), 0.96 (s, 9H), 0.10 (s, 3H), 0.05 (s, 3H). $^{13}$C NMR (75 MHz): 172.2, 155.7, 137.5, 136.5, 129.2, 128.5, 128.5, 128.1, 128.0, 126.6, 72.1, 66.6, 55.5, 52.0, 38.1, 25.8, 18.4, −4.7, −5.3; EI-HRMS Calcd for $C_{25}H_{35}NO_5Si$ (MH$^+$): 457.6421. Found 357.1914.

erythro-Methyl 3-N-benzyloxycarbonylamino-2-(tert-butyldimethylsilyloxy)-4-phenylbutane

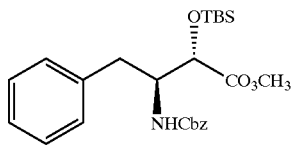

Colorless oil; FT-IR (CHCl$_3$): 3443, 2954, 1753, 1719, 1507, 1254, 1150, 838 cm$^{-1}$; $^1$H NMR (300 MHz): 7.39–7.10 (m. 10H), 5.03 (s, 2H), 4.86 (brd, J=7.6 Hz, NH), 4.45 (d, J=3.1 Hz, 1H), 4.50–4.25 (m, 1H), 3.64 (s, 3H), 2.87–2.62 (m, 2H), 0.93 (s, 9H), 0.08 (s, 3H), 0.01 (s, 3H). $^{13}$C NMR (75 MHz): 171.7, 155.6, 137.3, 136.4, 129.4, 128.5, 128.4, 128.1, 128.0, 126.7, 73.3, 66.7, 55.0, 51.8, 35.5, 25.7, 18.3, −5.0, −5.5; EI-HRMS Calcd for $C_{25}H_{35}NO_5Si$ (MH$^+$): 457.6421. Found 357.1914.

Then the compound (I) is reacted with the compound (III) in which PG is TBS and the compound (II) of NH—R$^3$R$^4$ to obtain the compound (IV). PG is TBS and Y is NR$^4$. A one-pot method for the synthesis of α-siloxyamides by the homologation of aldehydes or ketones was developed using H-MAC-TBS reagents.

TABLE 1

Reaction of 4-CH$_3$C$_6$H$_4$CHO to 4-CH$_3$C$_6$H$_4$CH(OTBS)-CONR$^3$R$^4$ with various amines (1.1 eq) and H-MAC-TBS (1.2 eq) at 0° C. for 5 min in acetonitrile

| entry | R$^3$R$^4$NH | Yield (%) |
|---|---|---|
| 1 | C$_4$H$_9$NH$_2$ | 96 |
| 2 | NH$_3$[a] | 90 |
| 3 | NH$_2$OH[b] | 78[c] |
| 4 | PhNH$_2$[d] | 88 |
| 5 | H$_2$N—CH$_2$—CO$_2$Me | 88 |
| 6 | HOCH$_2$CH$_2$NH$_2$ | 94 |
| 7 | (R)-PhCH(CH$_3$)NH$_2$ | 89[e] |
| 8 | (C$_2$H$_3$)$_2$NH | 77 |
| 9 | morphorine | 92 |

[a]10% Aqueous solution was used.
[b]50% of aqueous solution and one equivalent of triethylamine were used
[c]Carried out at −25° C. for 2 h.
[d]0.1 equivalents of DMAP was added.
[e]A mixture of diastereomer (1:1) was obtained.

TABLE 2

Preparation α-siloxyamides from conjugated aldehydes by with butylamine (1.1 eq) and H-MAC-TBS (1.2 eq) at 0° C. for 5 min in acetonitrile.

| entry | aldehyde | Isolated Yield (%) |
|---|---|---|
| 1 | 4-H$_3$C—C$_6$H$_4$—CHO | 96 |
| 2 | 2-HO—C$_6$H$_4$—CHO | 95 |
| 3 | furan-2-carbaldehyde | 94 |
| 4 | 2-Br—C$_6$H$_4$—CHO | 92 |
| 5 | 4-NC—C$_6$H$_4$—CHO | 97[a] |
| 6 | C$_6$H$_5$CH=CHCHO | 91 |
| 7 | CH$_3$CH=CHCHO | 82 |
| 8 | C$_6$H$_5$CH$_2$CH$_2$CHO | 63[b] |

[a]Direct synthesis of the corresponding α-hydroxyamide from 4-NC—C$_6$H$_4$CHO was also performed. The overall yield is 94%.
[b]Cyanohydrin of the starting aldehyde was obtained as a byproduct.

TABLE 3

Influence of solvent on the reaction of 2-ethylhexanal with butylamine (1.1 eq) and H-MAC-TBS (1.2 eq). Reaction conditions: −25° C. for 24 h

| entry | solvent | Isolated Yield (%) |
|---|---|---|
| 1 | acetonitrile | 54 |
| 2 | THF | 73 |
| 3 | THF + MS4Å | 80 |
| 4 | ether | 94 |
| 5 | CH$_2$Cl$_2$ | 67 |
| 6 | toluene | 92 |
| 7 | hexane | 90 |

TABLE 4

Reactions of various aldehydes and ketones in acetonitrile or ether

| entry | aldehyde | conditions[a] | Yield |
|---|---|---|---|
| 1 | C$_6$H$_5$CH$_2$CH$_2$CHO | A-y | 82 |
| 2 |  | E-y | 85 |
| 3 | Ph$_2$CHCHO | E-y | 84 |
| 4 | (CH$_3$)$_3$CCHO | E-z | 23 |
| 5 | 4-O$_2$N—C$_6$H$_4$COCH$_3$ | A-x | 94 |
| 6 | 4-H$_3$C—C$_6$H$_4$COCH$_3$ | E-y | 73 |
| 7 |  | A-z | 96 |
| 8 | cyclohexanone | E-x | 98 |
| 9 | 3-pentanone | E-z | 75 |

[a]A: in acetonitrile, E: in ether
x: H-MAC-TBS (1.2 eq), butylamine (1.1 eq), 0° C., 5 min
y: H-MAC-TBS (1.2 eq), butylamine (1.1 eq), −25° C., 2 h
z: H-MAC-TBS (3.0 eq), butylamine (3.0 eq), −25° C., 2 h Scheme 1

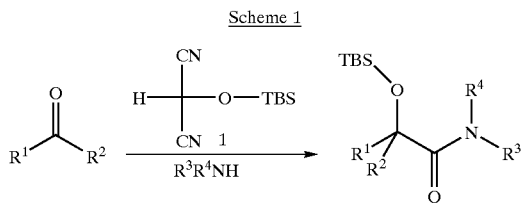

FIG. 1

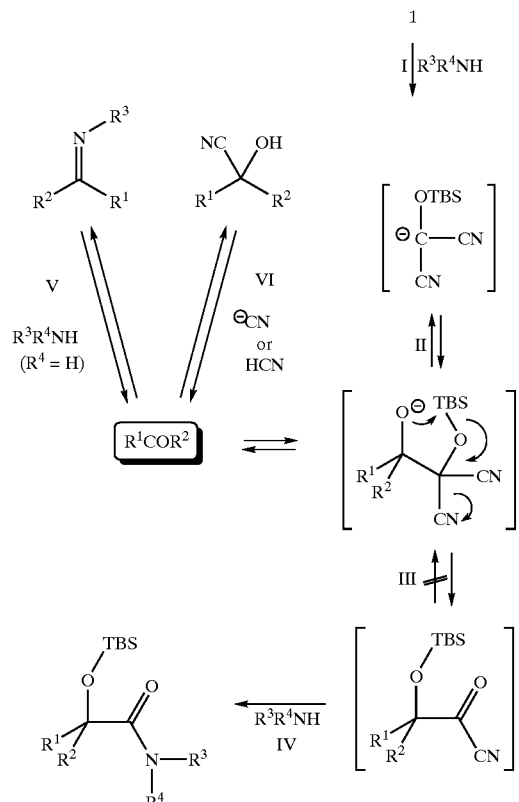

What is claimed is:

1. A process for producing an α-hydroxy-carbonyl compound or an α-protected hydroxy-carbonyl compound represented by the formula (IV) or (IV'):

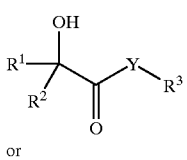
(IV)

or

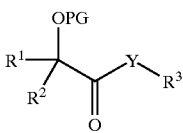
(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

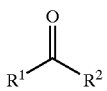
(I)

wherein, $R^1$ and $R^2$ are the same as or different from each other and each represents an organic group;

$$R^3\text{—YH} \qquad \text{(II)}$$

wherein, $R^3$ represents an organic group, and Y represents oxygen atom, sulfur atom or the formula $R^4N$ (wherein $R^4$ represents an organic group); and

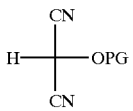
(III)

wherein, PG represents:
- a) a silyl group which may be substituted by at least one selected from the group consisting of an alkyl group, an alkoxy group, a cycloalkyl group, an optionally substituted aryl group and an optionally substituted heteroaryl group;
- b) an alkanoyl group;
- c) an alkenoyl group;
- d) an alkynoyl group;
- e) an aryloyl group;
- f) a heteroaryloyl group;
- g) an arylalkanoyl group;
- h) a heteroarylalkanoyl group;
- i) an alkylarylalkanoyl group;
- j) an alkylsulfonyl group;
- k) an alkylsulfinyl group;
- l) an arylsulfonyl group;
- m) an arylsulfinyl group;
- n) a heteroarylsulfonyl group;
- o) a heteroarylsulfinyl group;
- p) an arylalkylsulfonyl group;
- q) an arylalkylsulfinyl group;
- r) a heteroarylalkylsulfonyl group;
- r) a heteroarylalkylsulfinyl group;
- t) an alkylarylsulfonyl group;
- u) an alkylarylsulfinyl group;
- v) an alkylheteroarylsulfonyl group;
- w) an alkylheteroarylsulfinyl group;
- x) an alkylphosphonyl group;
- y) an arylphosphonyl group; or
- z) a heteroarylphosphonyl group.

2. A process for producing an α-hydroxy-carbonyl compound or an α-protected hydroxy-carbonyl compound represented by the formula (IV) or (IV'):

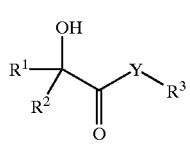
(IV)

or

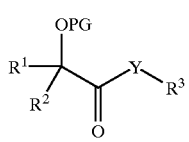
(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

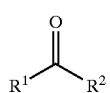
(I)

wherein, $R^1$ and $R^2$ are the same as or different from each other and each represents an aliphatic, alicyclic or aromatic hydrocarbon group, which may be protected, have at least one substituent and have at least one heteroatom;

$$R^3\text{—YH} \qquad \text{(II)}$$

wherein, $R^3$ represents an aliphatic, alicyclic or aromatic hydrocarbon group, which may be protected, have at least one substituent and have at least one heteroatom, and an amino group or alkoxy group, which may be protected, have at least one substituent and have at least one heteroatom; and Y represents oxygen atom, sulfur atom or the formula $R^4 N$ (wherein $R^4$ represents an aliphatic, alicyclic or aromatic hydrocarbon group, which may be protected, have at least one substituent and have at least one heteroatom); and

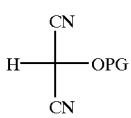

(III)

wherein, PG represents:
  a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
  b) a $C_{2-9}$ alkanoyl group;
  c) a $C_{3-9}$ alkenoyl group;
  d) a $C_{3-9}$ alkynoyl group;
  e) a $C_{7-13}$ aryloyl group;
  f) a 5 to 12-membered heteroaryloyl group;
  g) a $C_{6-12}$ aryl $C_{2-9}$ alkanoyl group;
  h) a 5 to 12-membered heteroaryl $C_{2-9}$ alkanoyl group;
  i) a $C_{1-8}$ alkyl $C_{6-12}$ aryl $C_{2-9}$ alkanoyl group;
  j) a $C_{1-8}$ alkylsulfonyl group;
  k) a $C_{1-8}$ alkylsulfinyl group;
  l) a $C_{6-12}$ arylsulfonyl group;
  m) a $C_{6-12}$ arylsulfinyl group;
  n) a 5 to 12-membered heteroarylsulfonyl group;
  o) a 5 to 12-membered heteroarylsulfinyl group;
  p) a $C_{6-12}$ aryl $C_{1-8}$ alkylsulfonyl group;
  q) a $C_{6-12}$ aryl $C_{1-8}$ alkylsulfinyl group;
  r) a 5 to 12-membered heteroaryl $C_{1-8}$ alkylsulfonyl group;
  s) a 5 to 12-membered heteroaryl $C_{1-8}$ alkylsulfinyl group;
  t) a $C_{1-8}$ alkyl $C_{6-12}$ arylsulfonyl group;
  u) a $C_{1-8}$ alkyl $C_{6-12}$ arylsulfinyl group;
  v) a $C_{1-8}$ alkyl 5 to 12-membered heteroarylsulfonyl group;
  w) a $C_{1-8}$ alkyl 5 to 12-membered heteroarylsulfinyl group;
  x) a $C_{1-6}$ alkylphosphonyl group;
  y) a $C_{6-12}$ arylphosphonyl group; or
  z) a 5 to 12-membered heteroarylphosphonyl group.

3. A process for producing an α-hydroxy-carbonyl compound or an α-protected hydroxy-carbonyl compound represented by the formula (IV) or (IV'):

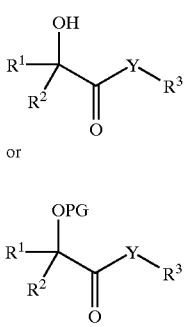

(wherein, $R^1$, $R^2$, $R^3$, PG and Y respectively have the same meanings as defined below), which comprises the steps of reacting the compound represented by the formula (I):

(I)

(wherein, $R^1$ and $R^2$ are the same as or different from each other and each represents hydrogen atom, a $C_{1-8}$ alkyl group, a $C_{3-8}$ cycloalkyl group, a $C_{4-8}$ bicycloalkyl group, a $C_{1-8}$ alkyl $C_{3-8}$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl alkenyl group, a $C_{1-8}$ alkylsulfinyl alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonylalkynyl group, a $C_{1-8}$ alkylsulfinylalkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a C5-12 alkynyl 5- to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ aklynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{1-8}$ alkynyl $C_{6-12}$ aryl $C_{1-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl a $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a C$_{2-8}$ alkynyl 5 to 12-membered heteroaryl C$_{2-8}$ alkenyl group, a C$_{2-8}$ alkynyl 5 to 12-membered heteroaryl C$_{2-8}$ alkynyl group, an amino C$_{1-8}$ alkyl group, a C$_{1-8}$ alkylamino C$_{1-8}$ alkyl group, di(C$_{1-8}$ alkyl)amino C$_{1-8}$ alkyl group, a C$_{1-8}$ alkoxyamino C$_{1-8}$ alkyl group, a C$_{2-9}$ alkanoylamino C$_{1-8}$ alkyl group, a C$_{6-12}$ arylamino C$_{1-8}$ alkyl group, di(C$_{6-12}$ aryl)amino C$_{1-8}$ alkyl group, a C$_{1-8}$ alkyl(C$_{6-12}$ aryl)amino C$_{1-8}$ alkyl group, a 5 to 12-membered heteroarylamino C$_{1-8}$ alkyl group, di(5 to 12-membered heteroaryl) amino C$_{1-8}$ alkyl group, a C$_{1-8}$ alkyl(5 to 12-membered heteroaryl) C$_{1-8}$ alkylamino group, an amino C$_{2-8}$ alkenyl group, a C$_{1-8}$ alkylamino C$_{2-8}$ alkenyl group, di(C$_{1-8}$ alkyl) amino C$_{2-8}$ alkenyl group, a C$_{1-8}$ alkoxyamino C$_{2-8}$ alkenyl group, a C$_{2-9}$ alkanoylamino C$_{2-8}$ alkenyl group, a C$_{6-12}$ arylamino C$_{2-8}$ alkenyl group, di(C$_{6-12}$ aryl)amino C$_{2-8}$ alkenyl group, a C$_{1-8}$ alkyl(C$_{6-12}$ aryl)amino C$_{2-8}$ alkenyl group, a 5 to 12-membered heteroarylamino C$_{2-8}$ alkenyl group, di(5 to 12-membered heteroaryl)amino C$_{2-8}$ alkenyl group, a C$_{1-8}$ alkyl(5 to 12-membered heteroaryl)amino C$_{2-8}$ alkenyl group, an amino C$_{2-8}$ alkynyl group, a C$_{1-8}$ alkylamino C$_{2-8}$ alkynyl group, di(C$_{1-8}$ alkyl)amino C$_{2-8}$ alkynyl group, a C$_{1-8}$ alkoxyamino C$_{2-8}$ alkynyl group, a C$_{2-9}$ alkanoylamino C$_{2-8}$ alkynyl group, a C$_{6-12}$ arylamino C$_{2-8}$ alkynyl group, di(C$_{6-12}$ aryl)amino C$_{2-8}$ alkynyl group, a C$_{1-8}$ alkyl(C$_{6-12}$ aryl)amino C$_{2-8}$ alkynyl group, a 5 to 12-membered heteroarylamino C$_{2-8}$ alkynyl group, di(5 to 12-membered heteroaryl)amino C$_{2-8}$ alkynyl group or a C$_{1-8}$ alkyl(5 to 12-membered heteroaryl)amino C$_{2-8}$ alkynyl group, which may be respecteively protected if necessary, and are independent of each other and may be substituted by at least one optional group selected from the group represented by Z$^1$ (wherein, Z$^1$ has the same meaning as Z$^3$); provided that the compound in which both R$^1$ and R$^2$ are hydrogen atoms is excluded), the compound represented by the formula (II):

R$^3$—YH        (II)

(wherein, R$^3$ represents hydrogen atom, hydroxy group, a C$_{1-8}$ alkyl group, a C$_{3-8}$ cycloalkyl group, a C$_{4-8}$ bicycloalkyl group, a C$_{1-8}$ alkyl C$_{3-8}$ cycloalkyl group, a C$_{1-8}$ alkoxy C$_{1-8}$ alkyl group, a hydroxy C$_{1-8}$ alkyl group, a mercapto C$_{1-8}$ alkyl group, a C$_{1-8}$ alkylthio C$_{1-8}$ alkyl group, a C$_{1-8}$ alkylsulfonyl C$_{1-8}$ alkyl group, a C$_{1-8}$ alkylsulfinyl C$_{1-8}$ alkyl group, a halogeno C$_{1-8}$ alkyl group, a nitro C$_{1-8}$ alkyl group, a cyano C$_{1-8}$ alkyl group, a C$_{1-8}$ alkoxycarbonyl C$_{1-8}$ alkyl group, C$_{1-8}$ alkylthiocarbonyl C$_{1-8}$ alkyl group, a C$_{1-8}$ alkylaminocarbonyl C$_{1-8}$ alkyl group, di C$_{1-8}$ alkylaminocarbonyl C$_{1-8}$ alkyl group, a C$_{2-9}$ alkanoyl C$_{1-8}$ alkyl group, a C$_{2-9}$ alkanoyloxy C$_{1-8}$ alkyl group, a C$_{2-8}$ alkenyl group, a C$_{3-8}$ cycloalkenyl group, a C$_{1-8}$ alkyl C$_{3-8}$ cycloalkenyl group, a C$_{1-8}$ alkoxyl C$_{1-8}$ alkenyl group, a hydroxy C$_{1-8}$ alkenyl group, a mercapto C$_{1-8}$ alkenyl group, a C$_{1-8}$ alkylthio C$_{1-8}$ alkenyl group, a C$_{1-8}$ alkylsulfonyl C$_{1-8}$ alkenyl group, a C$_{1-8}$ alkylsulfinyl C$_{1-8}$ alkenyl group, a halogeno C$_{1-8}$ alkenyl group, a nitro C$_{1-8}$ alkenyl group, a cyano C$_{1-8}$ alkenyl group, a C$_{2-8}$ alkynyl group, C$_{3-8}$ cycloalkynyl group, a C$_{1-8}$ alkyl C$_{3-8}$ cycloalkynyl group, a C$_{1-8}$ alkoxy C$_{1-8}$ alkynyl group, a hydroxy C$_{1-8}$ alkynyl group, a mercapto C$_{1-8}$ alkynyl group, a C$_{1-8}$ alkylthio C$_{1-8}$ alkynyl group, a C$_{1-8}$ alkylsulfonyl C$_{1-8}$ alkynyl group, a C$_{1-8}$alkylsulfinyl C$_{1-8}$ alkynyl group, a halogeno C$_{1-8}$ alkynyl group, a nitro C$_{1-8}$ alkynyl group, a cyano C$_{1-8}$ alkynyl group, a C$_{6-12}$ aryl group, a 5 to 12-membered heteroaryl group, a C$_{1-8}$ alkyl C$_{6-12}$ aryl group, a C$_{2-8}$ alkenyl C$_{6-12}$ aryl group, a C$_{2-8}$ alkynyl C$_{6-12}$ aryl group, a C$_{1-8}$ alkyl 5 to 12-membered heteroaryl group, a C$_{2-8}$ alkenyl 5-12-membered heteroaryl group, a C$_{5-12}$ alkynyl 5 to 12-membered heteroaryl group, a hydroxy C$_{6-12}$ aryl group, a mercapto C$_{6-12}$ aryl group, a C$_{1-8}$ alkylthio C$_{6-12}$ aryl group, a C$_{1-8}$ alkylsulfonyl C$_{6-12}$ aryl group, a C$_{1-8}$ alkylsulfinyl C$_{1-12}$ aryl group, a hydroxy 5 to 12-membered heteroaryl group, a mercapto 5 to 12-membered heteroaryl group, a C$_{1-8}$ alkylthio 5 to 12-membered heteroaryl group, a C$_{1-8}$ alkylsulfonyl 5 to 12-membered heteroaryl group, a C$_{1-8}$ alkylsulfinyl 5 to 12-membered heteroaryl group, a halogeno C$_{6-12}$ aryl group, a nitro C$_{6-12}$ aryl group, a cyano C$_{6-12}$ aryl group, a halogeno 5 to 12-membered heteroaryl group, a nitro 5 to 12-membered heteroaryl group, a cyano 5 to 12-membered heteroaryl group, a C$_{6-12}$ aryl C$_{1-8}$ alkyl group, a C$_{6-12}$ aryl C$_{2-8}$ alkenyl group, a C$_{6-12}$ aryl C$_{2-8}$ alkynyl group, a 5 to 12-membered heteroaryl C$_{1-8}$ alkyl group, a 5 to 12-membered heteroaryl C$_{2-8}$ alkenyl group, a 5 to 12-membered heteroaryl C$_{2-8}$ alkynyl group, a C$_{1-8}$ alkyl C$_{6-12}$ aryl C$_{1-8}$ alkyl group, a C$_{1-8}$ alkyl C$_{6-12}$ aryl C$_{2-8}$ alkenyl group, a C$_{1-8}$ alkyl C$_{6-12}$ aryl C$_{2-8}$ alkynyl group, C$_{2-8}$ alkenyl C$_{6-12}$ aryl C$_{1-8}$ alkyl group, a C$_{2-8}$ alkenyl C$_{6-12}$ aryl C$_{2-8}$ alkenyl group, a C$_{2-8}$ alkenyl C$_{6-12}$ aryl C$_{2-8}$ alkynyl group, a C$_{2-8}$ alkynyl C$_{6-12}$ aryl C$_{1-8}$ alkyl group, a C$_{2-8}$ alkynyl C$_{6-12}$ aryl C$_{2-8}$ alkenyl group, a C$_{2-8}$ alkynyl C$_{6-12}$ aryl C$_{2-8}$ alkynyl group, a C$_{1-8}$ alkyl 5 to 12-membered heteroaryl C$_{1-8}$ alkyl group, C$_{1-8}$ alkyl 5 to 12-membered heteroaryl C$_{2-8}$ alkenyl group, a C$_{1-8}$ alkyl 5 to 12-membered heteroaryl C$_{2-8}$ alkynyl group, a C$_{2-8}$ alkenyl 5 to 12-membered heteroaryl C$_{1-8}$ alkyl group, a C$_{2-8}$ alkenyl 5 to 12-membered heteroaryl C$_{2-8}$ alkenyl group, a C$_{2-8}$ alkenyl 5 to 12-membered heteroaryl C$_{2-8}$ alkynyl group, a C$_{2-8}$ alkynyl 5 to 12-membered heteroaryl C$_{1-8}$ alkyl group, a C$_{2-8}$ alkynyl 5 to 12-membered heteroaryl C$_{2-8}$ alkenyl group, a C$_{2-8}$ alkynyl 5 to 12-membered heteroaryl C$_{1-8}$ alkynyl group, an amino group, a C$_{1-8}$ alkylamino group, di(C$_{1-8}$ alkyl)amino group, a C$_{1-8}$ alkoxyamino group, a C$_{2-9}$ alkanoylamino group, a C$_{6-12}$ arylamino group, di(C$_{6-12}$ aryl)amino group, a C$_{1-8}$ alkyl (C$_{6-12}$ aryl)amino group, a 5 to 12-membered heteroarylamino group, di(5 to 12-membered heteroaryl)amino group, a C$_{1-8}$ alkyl(5 to 12-membered heteroaryl)amino group, an amino C$_{1-8}$ alkyl group, a C$_{1-8}$ alkylamino C$_{1-8}$ alkyl group, di(C$_{1-8}$ alkyl)amino C$_{1-8}$ alkyl gorup, a C$_{1-8}$ alkoxyamino C$_{1-8}$ alkyl gorup, a C$_{2-9}$ alkanoylamino C$_{1-8}$ alkyl group, a C$_{6-12}$ arylamino C$_{1-8}$ alkyl group, di(C$_{6-12}$ aryl)amino C$_{1-8}$ alkyl group, a C$_{1-8}$ alkyl(C$_{6-12}$ aryl)amino C$_{1-8}$ alkyl group, a 5 to 12-membered heteroarylamino C$_{1-8}$ alkyl group, di(5 to 12-membered heteroaryl)amino C$_{1-8}$ alkyl group, a C$_{1-8}$ alkyl(5 to 12-membered heteroaryl) C$_{1-8}$ alkylamino group, an amino C$_{2-8}$ alkenyl group, a C$_{1-8}$ alkylamino C$_{2-8}$ alkenyl group, di(C$_{1-8}$ alkyl)amino C$_{2-8}$ alkenyl group, a C$_{1-8}$ alkoxyamino C$_{2-8}$ alkenyl group, a C$_{2-9}$ alkanoylamino C$_{2-8}$ alkenyl group, a C$_{6-12}$ arylamino C$_{2-8}$ alkenyl group, di(C$_{6-12}$ aryl)amino C$_{2-8}$ a alkenyl group, a C$_{1-8}$ alkyl(C$_{6-12}$ aryl)amino C$_{2-8}$ alkenyl group, a 5 to 12-membered heteroarylamino C$_{2-8}$ alkenyl group, di(5 to 12-membered heteroaryl)amino C$_{2-8}$ alkenyl group, a C$_{1-8}$ alkyl(5 to 12-membered heteroaryl)amino C$_{2-8}$ alkenyl group, an amino C$_{2-8}$ alkynyl group, a C$_{1-8}$ alkylamino C$_{2-8}$ alkynyl group, di(C$_{1-8}$ alkyl)amino C$_{2-8}$ alkynyl group, a C$_{1-8}$ alkoxyamino C$_{2-8}$ alkynyl group, a C$_{2-9}$ alkanoylamino C$_{2-8}$ alkynyl group, a C$_{6-12}$ arylamino C$_{2-8}$ alkynyl group, di(C$_{6-12}$ aryl)amino C$_{2-8}$ alkynyl group, a C$_{1-8}$ alkyl(C$_{6-12}$ aryl)amino C$_{2-8}$ alkynyl group, a 5 to 12-membered heteroarylamino C$_{2-8}$ alkynyl group, di(5 to 12-membered heteroaryl)amino C$_{2-8}$ alkynyl group or a C$_{1-8}$ alkyl(5 to 12-membered heteroaryl)amino C$_{2-8}$ alkynyl group which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N—$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl)amino group, a 5 to 12-membered heteroarylamino group, di(5 to 12-membered heteroaryl)amino group, a $C_{1-8}$ alkyl(5 to 12-membered heteroaryl)amino group, a $C_{1-8}$ alkyl group, a $C_{3-8}$ cycloalkyl group, a $C_{4-8}$ bicycloalkyl group, a $C_{1-8}$ alkyl $C_{3-8}$ cyclo alkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkylthio group, a $C_{1-8}$ alkyl sulfonyl $C_{1-8}$ alkyl group, a $C_{1-8}$ alkylsulfinyl $C_{1-8}$ alkyl group, a halogeno $C_{1-8}$ alkyl gorup, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryll group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{6-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio 5 to 12-membered heteroaryl group, a $C_{1-8}$ alkylsulfonyl 5 to 12-membered heteroaryl group, a $C_{1-8}$ alkylsulfinyl 5 to 12-membered heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, a $C_{1-8}$ alkoxy group, a $C_{3-8}$ cycloalkoxy group, a $C_{4-8}$ bicycloalkoxy group, a $C_{1-8}$ alkyl $C_{3-8}$ cycloalkoxy group, a $C_{1-8}$ alkoxy $C_{1-8}$ alkoxy group, a hydroxy $C_{1-8}$ alkoxy group, a mercapto $C_{1-8}$ alkoxy group, a $C_{1-8}$ alkylthio $C_{1-8}$ alkoxy group, a $C_{1-8}$ alkylsulfonyl $C_{1-8}$ alkoxy group, a $C_{1-8}$ alkylsulfinyl $C_{1-8}$ alkoxy group, a halogeno $C_{1-8}$ alkoxy group, a nitro $C_{1-8}$ alkoxy group, a cyano $C_{1-8}$ alkoxy group, a $C_{1-8}$ alkoxycarbonyl $C_{1-8}$ alkoxy group, a $C_{1-8}$ alkylthiocarbonyl $C_{1-8}$ alkoxy group, a $C_{2-9}$ alkanoyl $C_{1-8}$ alkoxy group, a $C_{2-9}$ alkanoyloxy $C_{1-8}$ alkoxy group, a $C_{2-8}$ alkenyloxy group, a $C_{3-8}$ cycloalkenyloxy group, a $C_{1-8}$ alkyl $C_{3-8}$ cycloalkenyloxy group, a $C_{1-8}$ alkoxy $C_{1-8}$ alkenyloxy group, a hydroxy $C_{1-8}$ alkenyloxy group, a mercapto $C_{1-8}$ alkenyloxy group, a $C_{1-8}$ alkylthio $C_{1-8}$ alkenyloxy group, a $C_{1-8}$ alkylsulfonyl $C_{1-8}$ alkenyloxy group, a $C_{1-8}$ alkylsulfinyl $C_{1-8}$ alkenyloxy group, a halogeno $C_{1-8}$ alkenyloxy group, a nitro $C_{1-8}$ alkenyloxy group, a cyano $C_{1-8}$ alkenyloxy group, a $C_{2-8}$ alkynyloxy group, a $C_{3-8}$ cycloalkynyloxy group, a $C_{1-8}$ alkyl $C_{3-8}$ cycloalkynyl oxy group, a $C_{1-8}$ alkoxy $C_{1-8}$ alkynyloxy group, a hydroxy $C_{1-8}$ alkynyloxy group, a mercapto $C_{1-8}$ alkynyloxy group, a $C_{1-8}$ alkylthio $C_{1-8}$ alkynyloxy group, a $C_{1-8}$ alkylsulfonyl $C_{1-8}$ alkynyloxy group, a $C_{1-8}$ alkylsulfinyl $C_{1-8}$ alkynyloxy group, a halogeno $C_{1-8}$ alkynyloxy group, a nitro $C_{1-8}$ alkynyloxy group, a cyano $C_{1-8}$ alkynyloxy group, a $C_{6-12}$ aryloxy group, a 5 to 12-membered heteroaryloxy group, a $C_{1-8}$ alkyl $C_{6-12}$ aryloxy group, a $C_{2-8}$ alkenyl $C_{6-12}$ aryloxy group, a $C_{2-8}$ alkynyl $C_{6-12}$ aryloxy group, a $C_{1-8}$ alkyl 5 to 12-membered heteroaryloxy group, a $C_{2-8}$ alkenyl 5 to 12-membered heteroaryloxy group, a $C_{5-12}$ alkynyl 5 to 12-membered heteroaryloxy group, a hydroxy $C_{6-12}$ aryloxy group, a mercapto $C_{6-12}$ aryloxy group, a $C_{1-8}$ alkylthio $C_{6-12}$ aryloxy group, a $C_{1-8}$ alkylsulfonyl $C_{6-12}$ aryloxy group, a $C_{1-8}$ alkylsulfinyl $C_{6-12}$ aryloxy group, a hydroxy 5 to 12-membered heteroaryloxy group, a mercapto 5 to 12-membered heteroaryloxy group, a $C_{1-8}$ alkylthio $C_{6-12}$ heteroaryloxy group, a $C_{1-8}$ alkylsulfonyl $C_{6-12}$ heteroaryloxy group, a $C_{1-8}$ alkylsulfinyl $C_{6-12}$ heteroaryloxy group, a halogeno $C_{6-12}$ aryloxy group, a nitro $C_{6-12}$ aryloxy group, a cyano $C_{6-12}$ aryloxy group, a halogeno 5 to 12-membered heteroaryloxy group, a nitro 5 to 12-membered heteroaryloxy group, a cyano 5 to 12-membered heteroaryloxy group, a $C_{6-12}$ aryl $C_{1-8}$ alkoxyl group, a $C_{6-12}$ aryl $C_{2-8}$ alkenyloxy group, a $C_{6-12}$ aryl $C_{2-8}$ alkynyloxy group, a 5 to 12-membered heteroaryl $C_{1-8}$ alkoxy group, a 5 to 12-membered heteroaryl $C_{2-8}$ alkenyloxy group, a 5 to 12-membered heteroaryl $C_{2-8}$ alkynyloxy group, a $C_{1-8}$ alkyl $C_{6-12}$ aryl $C_{1-8}$ alkoxyl group, a $C_{1-8}$ alkyl $C_{6-12}$ aryl $C_{2-8}$ alkenyloxy group, a $C_{1-8}$ alkyl $C_{6-12}$ aryl $C_{2-8}$ alkynyloxy group, a $C_{2-8}$ alkenyl $C_{6-12}$ aryl $C_{1-8}$ alkoxy group, a $C_{2-8}$ alkenyl $C_{6-12}$ aryl $C_{2-8}$ alkenyloxy group, a $C_{2-8}$ alkenyl $C_{6-12}$ aryl $C_{2-8}$ alkynyloxy group, a $C_{2-8}$ alkynyl $C_{6-12}$ aryl $C_{1-8}$ alkoxy group, a $C_{2-8}$ alkynyl $C_{6-12}$ aryl $C_{2-8}$ alkenyloxy group, a $C_{2-8}$ alkynyl $C_{6-12}$ aryl $C_{2-8}$ alkynyloxy group, a $C_{1-8}$ alkyl 5 to 12-membered heteroaryl $C_{1-8}$ alkoxy group, a $C_{1-8}$ alkyl 5 to 12-membererd heteroaryl $C_{2-8}$ alkenyloxy group, a $C_{1-8}$ alkyl 5 to 12-membered heteroaryl $C_{2-8}$ alkynyloxy group, a $C_{2-8}$ alkenyl 5 to 12-membered heteroaryl $C_{1-8}$ alkoxy group, a $C_{2-8}$ alkenyl 5 to 12-membered heteroaryl $C_{2-8}$ alkenyloxy group, a $C_{2-8}$ alkenyl 5 to 12-membererd heteroaryl $C_{2-8}$ alkynyloxy group, a $C_{2-8}$ alkynyl 5 to 12-membered heteroaryl $C_{1-8}$ alkoxy group, a $C_{2-8}$ alkynyl 5 to 12-membered heteroaryl $C_{2-8}$ alkenyloxy group, a $C_{2-8}$ alkynyl 5 to 12-membered heteroaryl $C_{2-8}$ alkynyloxy group, a $C_{1-8}$ alkylthio group, a $C_{1-8}$ alkylsulfonyl group, a $C_{1-8}$ alkylsulfinyl group, a $C_{3-8}$ cycloalkylthio group, a $C_{3-8}$ cycloalkylsulfonyl group, a $C_{3-8}$ cycloalkylsulfinyl group, a $C_{4-8}$ bicycloalkylthio group, a $C_{4-8}$ bicycloalkylsulfonyl group, a $C_{4-8}$ bicycloalkylsulfinyl group, a $C_{1-8}$ alkyl $C_{3-8}$ cycloalkylthio group, a $C_{1-8}$ alkyl $C_{3-8}$ cycloalkylsulfonyl group, a $C_{1-8}$ alkyl $C_{3-8}$ cycloalkylsulfinyl group, a $C_{1-8}$ alkoxy $C_{1-8}$ alkylthio group, a $C_{1-8}$ alkoxy $C_{1-8}$ alkylsulfonyl group, a $C_{1-8}$ alkoxy $C_{1-8}$ alkylsulfinyl group, a hydroxy $C_{1-8}$ alkylthio group, a hydroxy $C_{1-8}$ alkylsulfonyl group, a hydroxy $C_{1-8}$ alkylsulfinyl group, a mercapto $C_{1-8}$ alkylthio group, a mercapto $C_{1-8}$ alkylsulfonyl group, a mercapto $C_{1-8}$ alkylsulfinyl group, a halogeno $C_{1-8}$ alkylthio group, a halogeno $C_{1-8}$ alkylsulfonyl group, a halogeno $C_{1-8}$ alkylsulfinyl group, a nitro $C_{1-8}$ alkylthio group, a nitro $C_{1-8}$ akylsulfonyl group, a nitro $C_{1-8}$ alkylsulfinyl group, a cyano $C_{1-8}$ alkylthio group, a cyano $C_{1-8}$ alkylsulfonyl group, a cyano $C_{1-8}$ alkylsulfinyl group, a $C_{1-8}$ alkoxycarbonyl $C_{1-8}$ alkylthio group, a $C_{1-8}$ alkoxycarbonyl $C_{1-8}$ alkylsulfonyl group, a $C_{1-8}$ alkoxycarbonyl $C_{1-8}$ alkylsulfinyl group, a $C_{1-8}$ alkylthiocarbonyl $C_{1-8}$ alkylthio group, a $C_{1-8}$ alkylthiocarbonyl $C_{1-8}$ alkylsulfonyl group, a $C_{1-8}$ alkylthiocarbonyl $C_{1-8}$ alkylsulfinyl group, a $C_{2-9}$ alkanoyl $C_{1-8}$ alkylthio group, a $C_{2-9}$ alkanoyl $C_{1-8}$ alkylsulfonyl group, a $C_{2-9}$ alkanoyl $C_{1-8}$ alkylsulfinyl group, a $C_{2-9}$ alkanoyloxy $C_{1-8}$ alkylthio group, a $C_{2-9}$ alkanoyloxy $C_{1-8}$ alkylsulfonyl group, a $C_{2-9}$ alkanoyloxy $C_{1-8}$ alkylsulfinyl group, a $C_{2-8}$ alkenylthio group, a $C_{2-8}$ alkenylsulfonyl group, a $C_{2-8}$ alkenylsulfinyl group, a $C_{3-8}$ cycloalkenylthio group, a $C_{3-8}$ cycloalkenylsulfonyl group, a $C_{3-8}$ cycloalkenylsulfinyl group, a $C_{1-8}$ alkyl $C_{3-8}$ cycloalkenylthio group, a $C_{1-8}$ alkyl $C_{3-8}$ cycloalkenylsulfonyl group, a $C_{1-8}$ alkyl $C_{3-8}$ cycloalkenylsulfinyl group, a $C_{1-8}$ alkoxy $C_{1-8}$ alkenylthio group, a $C_{1-8}$ alkoxy $C_{1-8}$ alkenylsulfonyl group, a $C_{1-8}$ alkoxy $C_{1-8}$ alkenylsulfinyl group, a hydroxy $C_{1-8}$ alkenylthio group, a hydroxy $C_{1-8}$ alkenylsulfonyl group, a hydroxy $C_{1-8}$ alkenylsulfinyl group, a mercapto $C_{1-8}$ alkenylthio group, a mercapto $C_{1-8}$ alkenylsulfonyl group, a mercapto $C_{1-8}$ alkenylsulfinyl group, a $C_{1-8}$ alkylthio $C_{1-8}$ alkenylthio group, a $C_{1-8}$ alkylthio $C_{1-8}$ alkenylsulfonyl group, a $C_{1-8}$ alkylthio $C_{1-8}$ alkenylsulfinyl group, a halogeno $C_{1-8}$ alkenylthio group, a halogeno $C_{1-8}$ alkenylsulfonyl group, a halogeno $C_{1-8}$ alkenylsulfinyl group, a nitro $C_{1-8}$ alkenylthio group, a nitro $C_{1-8}$ alkenylsulfonyl group, a nitro $C_{1-8}$ alkenylsulfinyl group, a cyano $C_{1-8}$ alkenylthio group, a cyano $C_{1-8}$ alkenylsulfonyl group, a cyano $C_{1-8}$ alkenylsulfinyl group, a $C_{2-8}$ alkynylthio group, a $C_{2-8}$ alkynylsulfonyl group, a $C_{2-8}$ alkynylsulfinyl group, a $C_{3-8}$ cycloalkynylthio group, a $C_{3-8}$ cycloalkynylsulfonyl group, a $C_{3-8}$ cycloalkynylsulfinyl group, a $C_{1-8}$ a alkyl $C_{3-8}$ cycloalkynylthio group, a $C_{1-8}$ alkyl $C_{3-8}$ cycloalkynylsulfonyl group, a $C_{1-8}$ alkyl $C_{3-8}$ cycloalkynylsulfinyl group, a $C_{1-8}$ alkoxy $C_{1-8}$ alkynylthio group, a $C_{1-8}$ alkoxy $C_{1-8}$ alkynylsulfonyl group, a $C_{1-8}$ alkoxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a hydroxy $C_{1-8}$ alkynylthio group, a hydroxy $C_{1-8}$ alkynylsulfonyl group, a hydroxy $C_{1-8}$ alkynylsulfinyl group, a mercapto $C_{1-8}$ alkynylthio group, a mercapto $C_{1-8}$ alkynylsulfonyl group, a mercapto $C_{1-8}$ alkynylsulfinyl group, a $C_{1-8}$ alkylthio $C_{1-8}$ alkynylthio group, a $C_{1-8}$ alkylthio $C_{1-8}$ alkynylsulfonyl group, a $C_{1-8}$ alkylthio $C_{1-8}$ alkynylsulfinyl group, a halogeno $C_{1-8}$ alkynylthio group, a halogeno $C_{1-8}$ alkynylsulfonyl group, a halogeno $C_{1-8}$ alkynylsulfinyl group, a nitro $C_{1-8}$ alkynylthio group, a nitro $C_{1-8}$ alkynylsulfonyl group, a nitro $C_{1-8}$ alkynylsulfinyl group, a cyano $C_{1-8}$ alkynylthio group, a cyano $C_{1-8}$ alkynylsulfonyl group, a cyano $C_{1-8}$ alkynylsulfinyl group, a $C_{6-12}$ arylthio group, a $C_{6-12}$ sulfonyl group, a $C_{6-12}$ arylsulfinyl group, a 5 to 12-membered heteroarylthio group, a 5 to 12-membered heteroarylsulfonyl group, a 5 to 12-membered heteroarylsulfinyl group, a $C_{1-8}$ alkyl $C_{6-12}$ arylthio group, a $C_{1-8}$ alkyl $C_{6-12}$ arylsulfonyl group, a $C_{1-8}$ alkyl $C_{6-12}$ arylsulfinyl group, a $C_{2-8}$ alkenyl $C_{6-12}$ arylthio group, a $C_{2-8}$ alkenyl $C_{6-12}$ arylsulfonyl group, a $C_{2-8}$ alkenyl $C_{6-12}$ arylsulfinyl group, a $C_{2-8}$ alkynyl $C_{6-12}$ arylthio group, a $C_{2-8}$ alkynyl $C_{6-12}$ arylsulfonyl group, a $C_{2-8}$ alkynyl $C_{6-12}$ arylsulfinyl group, a $C_{1-8}$ alkyl 5 to 12-membered heteroarylthio group, a $C_{2-8}$ alkenyl 5 to 12-membered heteroarylthio group, a $C_{5-12}$ alkynyl 5 to 12-membered heteroarylthio group, a hydroxy $C_{6-12}$ arylthio group, a mercapto $C_{6-12}$ arylthio group, a $C_{1-8}$ alkylthio $C_{6-12}$ arylthio group, a hydroxy 5 to 12-membered heteroarylthio group, a hydroxy 5 to 12-membered heteroarylsulfonyl group, a hydroxy 5 to 12-membered heteroarylsulfinyl group, a mercapto 5 to 12-membered heteroarylthio group, a mercapto 5 to 12-membered heteroarylsulfonyl group, a mercapto 5 to 12-membered heteroarylsulfinyl group, a $C_{1-8}$ alkylthio $C_{6-12}$ heteroarylthio group, a $C_{1-8}$ alkylthio $C_{6-12}$ heteroarylsulfonyl group, a $C_{1-8}$ alkylthio $C_{6-12}$ heteroarylsulfinyl group, a halogeno $C_{6-12}$ arylthio group, a halogeno $C_{6-12}$ aryl sulfonyl group, a halogeno $C_{6-12}$ arylsulfinyl group, a nitro $C_{6-12}$ arylthio group, a nitro $C_{6-12}$ arylsulfonyl group, anitro $C_{6-12}$ arylsulfinyl group, a cyano $C_{6-12}$ arylthio group, a cyano $C_{6-12}$ arylsulfonyl group, a cyano $C_{6-12}$ arylsulfinyl group, a halogeno 5 to 12-membered heteroarylthio group, a halogeno 5 to 12-membered heteroaryl sulfonyl group, a halogeno 5 to 12-membered heteroaryl sulfinyl group, a nitro 5 to 12-membered heteroarylthio group, a nitro 5 to 12-membered heteroarylsulfonyl group, a nitro 5 to 12-membered heteroarylsulfinyl group, a cyano 5 to 12-membered heteroarylthio group, a cyano 5 to 12-membered heteroaryl sulfonyl group, a cyano 5 to 12-membered heteroaryl sulfinyl group, a $C_{6-12}$ aryl $C_{1-8}$ alkylthio group, a $C_{6-12}$ aryl $C_{1-8}$ alkylsulfonyl group, a $C_{6-12}$ aryl $C_{1-8}$ alkylsulfinyl group, a $C_{6-12}$ aryl $C_{2-8}$ alkenylthio group, a $C_{6-12}$ aryl $C_{2-8}$ alkenylsulfonyl group, a $C_{6-12}$ aryl $C_{2-8}$ alkenylsulfinyl group, a $C_{6-12}$ aryl $C_{2-8}$ alkynylthio group, a $C_{6-12}$ aryl $C_{2-8}$ alkynylsulfonyl group, a $C_{6-12}$ aryl $C_{2-8}$ alkynylsulfinyl group, a 5 to 12-membered heteroaryl $C_{1-8}$ alkylthio group, a 5 to 12-membered heteroaryl $C_{1-8}$ alkylsulfonyl group, a 5 to 12-membered heteroaryl $C_{1-8}$ alkylsulfinyl group, a 5 to 12-membered heteroaryl $C_{2-8}$ alkenylthio group, a 5 to 12-membered heteroaryl $C_{2-8}$ alkenylsulfonyl group, a 5 to 12-membered heteroaryl $C_{2-8}$ alkenylsulfinyl group, a 5 to 12-membered heteroaryl $C_{2-8}$ alkynylthio group, a 5 to 12-membered heteroaryl $C_{2-8}$ alkynylsulfonyl a 5 to 12-membered heteroaryl $C_{2-8}$ alkynylsulfinyl group, a $C_{1-8}$ alkyl $C_{6-12}$ aryl $C_{1-8}$ alkylthio group, a $C_{1-8}$ alkyl $C_{6-12}$ aryl $C_{1-8}$ alkylsulfonyl group, a $C_{1-8}$ alkyl $C_{6-12}$ aryl $C_{1-8}$ alkylsulfinyl group, a $C_{1-8}$ alkyl $C_{6-12}$ aryl $C_{2-8}$ alkenylthio group, a $C_{1-8}$ alkyl $C_{6-12}$ aryl $C_{2-8}$ alkenylsulfonyl group, a $C_{1-8}$ alkyl $C_{6-12}$ aryl $C_{2-8}$ alkenylsulfinyl group, a $C_{1-8}$ alkyl $C_{6-12}$ aryl $C_{2-8}$ alkynylthio group, a $C_{1-8}$ alkyl $C_{6-12}$ aryl $C_{2-8}$ alkynylsulfonyl group, a $C_{1-8}$ alkyl $C_{6-12}$ aryl $C_{2-8}$ alkynylsulfinyl group, a $C_{2-8}$ alkenyl $C_{6-12}$ aryl $C_{1-8}$ alkylthio group, $C_{2-8}$ alkenyl $C_{6-12}$ aryl $C_{1-8}$ alkylsulfonyl group, a $C_{2-8}$ alkenyl $C_{6-12}$ aryl $C_{1-8}$ alkylsulfinyl group, a $C_{2-8}$ alkenyl $C_{6-12}$ aryl $C_{2-8}$ alkenylthio group, a $C_{2-8}$ alkenyl $C_{6-12}$ aryl $C_{2-8}$ alkenylsulfonyl group, a $C_{2-8}$ alkenyl $C_{6-12}$ aryl $C_{2-8}$ alkenylsulfinyl group, a $C_{2-8}$ alkenyl $C_{6-12}$ aryl $C_{2-8}$ alkynylthio group, a $C_{2-8}$ alkenyl $C_{6-12}$ aryl $C_{2-8}$ alkynylsulfonyl group, a $C_{2-8}$ alkenyl $C_{6-12}$ aryl $C_{2-8}$ alkynylsulfinyl group, a $C_{2-8}$ alkynyl $C_{6-12}$ aryl $C_{1-8}$ alkylthio group, a $C_{2-8}$ alkynyl $C_{6-12}$ aryl $C_{1-8}$ alkylsulfonyl group, a $C_{2-8}$ alkynyl $C_{6-12}$ aryl $C_{1-8}$ alkylsulfinyl group, a $C_{2-8}$ alkynyl $C_{6-12}$ aryl $C_{2-8}$ alkenylthio group, a $C_{2-8}$ alkynyl $C_{6-12}$ aryl $C_{2-8}$ alkenylsulfonyl group, a $C_{2-8}$ alkynyl $C_{6-12}$ aryl $C_{2-8}$ alkenylsulfinyl group, a $C_{2-8}$ alkynyl $C_{6-12}$ aryl $C_{2-8}$ alkynylthio group, a $C_{2-8}$ alkynyl $C_{6-12}$ aryl $C_{2-8}$ alkynylsulfonyl group, a $C_{2-8}$ alkynyl $C_{6-12}$ aryl $C_{2-8}$ alkynylsulfinyl group, a $C_{1-8}$ alkyl 5 to 12-membered heteroaryl $C_{1-8}$ alkylthio group, a $C_{1-8}$ alkyl 5 to 12-membered heteroaryl $C_{1-8}$ alkylsulfonyl group, a $C_{1-8}$ alkyl 5 to 12-membered heteroaryl $C_{1-8}$ alkylsulfinyl group, a $C_{1-8}$ alkyl 5 to 12-membered heteroaryl $C_{2-8}$ alkenylthio group, a $C_{1-8}$ alkyl 5 to 12-membered heteroaryl $C_{2-8}$ alkenylsulfonyl group, a $C_{1-8}$ alkyl 5 to 12-membered heteroaryl $C_{2-8}$ alkenylsulfinyl group, a $C_{1-8}$ alkyl 5 to 12-membered heteroaryl $C_{2-8}$ alkynylthio group, a $C_{1-8}$ alkyl 5 to 12-memberd heteroaryl $C_{2-8}$ alkynylsulfonyl group, a $C_{1-8}$ alkyl 5 to 12-membered heteroaryl $C_{2-8}$ alkynylsulfinyl group, a $C_{2-8}$ alkenyl 5 to 12-membered heteroaryl $C_{1-8}$ alkylthio group, a $C_{2-8}$ alkenyl 5 to 12-membered heteroaryl $C_{1-8}$ alkylsulfonyl group, a $C_{2-8}$ alkenyl 5 to 12-membered heteroaryl $C_{1-8}$ alkylsulfinyl group, a $C_{2-8}$ alkenyl 5 to 12-membered heteroaryl $C_{2-8}$ alkenylthio group, a $C_{2-8}$ alkenyl 5 to 12-membered heteroaryl $C_{2-8}$ alkenylsulfonyl group, a $C_{2-8}$ alkenyl 5 to 12-membered heteroaryl $C_{2-8}$ alkenylsulfinyl group, a $C_{2-8}$ alkenyl 5 to 12-membered heteroaryl $C_{2-8}$ alkynylthio group, a $C_{2-8}$ alkenyl 5 to 12-membered heteroaryl $C_{2-8}$ alkynylsulfonyl group, a $C_{2-8}$ alkenyl 5 to 12-membered heteroaryl $C_{2-8}$ alkynylsulfinyl group, a $C_{2-8}$ alkynyl 5 to 12-membered heteroaryl $C_{1-8}$ alkylthio group, a $C_{2-8}$ alkynyl 5 to 12-membered heteroaryl $C_{1-8}$ alkylsulfonyl group, a $C_{2-8}$ alkynyl 5 to 12-membered heteroaryl $C_{1-8}$ alkylsulfinyl group, a $C_{2-8}$ alkynyl 5 to 12-membered heteroaryl $C_{2-8}$ alkenylthio group, a $C_{2-8}$ S alkynyl 5 to 12-membered heteroaryl $C_{2-8}$ alkenylsulfonyl group, a $C_{2-8}$ alkynyl 5 to 12-membered heteroaryl $C_{2-8}$ alkenylsulfinyl group, a $C_{2-8}$ alkynyl 5 to 12-membered heteroaryl $C_{2-8}$ alkynylthio group, a $C_{2-8}$ alkynyl 5 to 12-membered heteroaryl $C_{2-8}$ alkynylsulfonyl group, a $C_{2-8}$ alkynyl 5 to 12-membered heteroaryl $C_{2-8}$ alkynyl sulfinyl group, an amino $C_{1-8}$ alkyl group, a $C_{1-8}$ alklylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroaryamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkodyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membererd heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl gorup, 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected); Y represents oxygen atom, sulfur atom or the formula $R^4N$ (wherein $R^4$ represents hydrogen atom, hydroxy group, a $C_{1-8}$ alkyl group, a $C_{3-8}$ cycloalkyl group, a $C_{4-8}$ bicycloalkyl group, a $C_{1-8}$ alkyl $C_3$ cycloalkyl group, a $C_{1-8}$ alkoxy $C_{1-8}$ alkyl group, a hydroxy $C_{1-8}$ alkyl group, a mercapto $C_{1-8}$ alkyl group, a $C_{1-8}$ alkylthio $C_{1-8}$ alkyl group, a $C_{1-8}$ alkylsulfonyl $C_{1-8}$ alkyl group, a $C_{1-8}$ alkylsulfinyl $C_{1-8}$ alkyl group, a halogeno $C_{1-8}$ alkyl group, a nitro $C_{1-8}$ alkyl group, a cyano $C_{1-8}$ alkyl group, a $C_{1-8}$ alkoxycarbonyl $C_{1-8}$ alkyl group, a $C_{1-8}$ alkylthiocarbonyl $C_{1-8}$ alkyl group, a $C_{1-8}$ alkylaminocarbonyl $C_{1-8}$ alkyl group, di $C_{1-8}$ alkylaminocarbonyl $C_{1-8}$ alkyl group, a $C_{2-9}$ alkanoyl $C_{1-8}$ alkyl group, a $C_{2-9}$ alkanoyloxy $C_{1-8}$ alkyl group, a $C_{2-8}$ alkenyl group, a $C_{3-8}$ cycloalkenyl group, a $C_{1-8}$ alkyl $C_{3-8}$ cycloalkenyl group, a $C_{1-8}$ alkoxy $C_{1-8}$ alkenyl group, a hydroxy $C_{1-8}$ alkenyl group, a mercapto $C_{1-8}$ alkenyl group, a $C_{1-8}$ alkylthio $C_{1-8}$ alkenyl group, a $C_{1-8}$ alkylsulfonyl $C_{1-8}$ alkenyl group, a $C_{1-8}$ alkylsulfinyl $C_{1-8}$ alkenyl group, a halogeno $C_{1-8}$ alkenyl group, a nitro $C_{1-8}$ alkenyl group, a cyano $C_{1-8}$ alkenyl group, a $C_{2-8}$ alkynyl group, a $C_{3-8}$ cycloalkynyl group, a $C_{1-8}$ alkyl $C_{3-8}$ cycloalkynyl group, a $C_{1-8}$ alkoxy $C_{1-8}$ alkynyl group, a hydroxy $C_{1-8}$ alkynyl group, a mercapto $C_{1-8}$ alkynyl group, a $C_{1-8}$ alkylthio $C_{1-8}$ alkynyl group, a $C_{1-8}$ alkylsulfonyl $C_{1-8}$ alkynyl group, a $C_{1-8}$ alkylsulfinyl $C_{1-8}$ alkynyl group, a halogeno $C_{1-8}$ alkynyl group, a nitro $C_{1-8}$ alkynyl group, a cyano $C_{1-8}$ alkynyl group, a $C_{6-12}$ aryl group, a 5 to 12-membered heteroaryl group, a $C_{1-8}$ alkyl $C_{6-12}$ aryl group, a $C_{2-8}$ alkenyl $C_{6-12}$ aryl group, a $C_{2-8}$ alkynyl $C_{6-12}$ aryl group, a $C_{1-8}$ alkyl 5 to 12-membered heteroaryl group, a $C_{2-8}$ alkenyl 5 to 12-membered heteroaryl group, a $C_{5-12}$ alkynyl 5 to 12-membered heteroaryl group, a hydroxy $C_{6-12}$ aryl group, a mercapto $C_{6-12}$ aryl group, a $C_{1-8}$ alkylthio $C_{6-12}$ aryl group, a $C_{1-8}$ alkylsulfonyl $C_{1-12}$ aryl group, a $C_{1-8}$ alkylsulfinyl $C_{6-12}$ aryl group, a hydroxy 5 to 12-membered heteroaryl group, a mercapto 5 to 12-membered heteroaryl group, a $C_{1-8}$ alkylthio $C_{6-12}$ heteroaryl group, a $C_{1-8}$ alkylsulfonyl $C_{6-12}$ heteroaryl group, $C_{1-8}$ alkylsulfinyl $C_{6-12}$ heteroaryl group, a halogeno $C_{6-12}$ aryl group, a nitro $C_{6-12}$ aryl group, a cyano $C_{6-12}$ aryl group, a halogeno 5 to 12-membered heteroaryl group, a nitro 5 to 12-membered heteroaryl group, a cyano 5 to 12-membered heteroaryl group, a $C_{6-12}$ aryl $C_{1-8}$ alkyl group, a $C_{6-12}$ aryl $C_{2-8}$ alkenyl group, a $C_{6-12}$ aryl $C_{2-8}$ alkynyl group, a 5 to 12-membered heteroaryl $C_{1-8}$ alkyl group, a 5 to 12-membered heteroaryl $C_{2-8}$ alkenyl group, a 5 to 12-membered heteroaryl $C_{2-8}$ alkynyl group, a $C_{1-8}$ alkyl $C_{6-12}$ aryl $C_{1-8}$ alkyl group, a $C_{1-8}$ alkyl $C_{6-12}$ aryl $C_{2-8}$ alkenyl group, a $C_{1-8}$ alkyl $C_{6-12}$ aryl $C_{2-8}$ alkynyl group, a $C_{2-8}$ alkenyl $C_{6-12}$ aryl $C_{1-8}$ alkyl group, a $C_{2-8}$ alkenyl $C_{6-12}$ aryl $C_{2-8}$ alkenyl group, a $C_{2-8}$ alkenyl $C_{6-12}$ aryl $C_{2-8}$ alkynyl group, a $C_{2-8}$ alkynyl $C_{6-12}$ aryl $C_{1-8}$ alkyl group, a $C_{2-8}$ alkynyl $C_{6-12}$ aryl $C_{2-8}$ alkenyl group, a $C_{2-8}$ alkynyl $C_{6-12}$ aryl $C_{2-8}$ alkynyl group, a $C_{1-8}$ alkyl 5 to 12-membered heteroaryl $C_{1-8}$ alkyl group, a $C_{1-8}$ alkyl 5 to 12-membered heteroaryl $C_{2-8}$ alkenyl group, a $C_{1-8}$ alkyl 5 to 12-membered heteroaryl $C_{2-8}$ alkynyl group, a $C_{2-8}$ alkenyl 5 to 12-membered heteroaryl $C_{1-8}$ alkyl group, a $C_{2-8}$ alkenyl 5 to 12-membered heteroaryl $C_{2-8}$ alkenyl group, a $C_{2-8}$ alkenyl 5 to 12-membered heteroaryl $C_{2-8}$ alkynyl group, a $C_{2-8}$ alkynyl 5 to 12-membered heteroaryl $C_{1-8}$ alkyl group, a $C_{2-8}$ alkynyl 5 to 12-membered heteroaryl $C_{2-8}$ alkenyl group, a $C_{2-8}$ alkynyl 5 to 12-membered heteroaryl $C_{2-8}$ alkynyl group, an amino $C_{1-8}$ alkyl group, a $C_{1-8}$ alkylamino $C_{1-8}$ alkyl group, di($C_{1-8}$ alkyl)amino $C_{1-8}$ alkyl group, a $C_{1-8}$ alkoxyamino $C_{1-8}$ alkyl group, a $C_{2-9}$ alkanoylamino $C_{1-8}$ alkyl group, a $C_{6-12}$ arylamino $C_{1-8}$ alkyl group, di($C_{6-12}$ aryl)amino $C_{1-8}$ alkyl group, a $C_{1-8}$ alkyl($C_{6-12}$ aryl)amino $C_{1-8}$ alkyl group, a 5 to 12-membered heteroarylamino $C_{1-8}$ alkyl group, di(5 to 12-membered heteroaryl)amino $C_{1-8}$ alkyl group, a $C_{1-8}$ alkyl(5 to 12-membered heteroaryl) $C_{1-8}$ alkylamino group, an amino $C_{2-8}$ alkenyl group, a $C_{1-8}$ alkylamino $C_{2-8}$ alkenyl group, di($C_{1-8}$ alkyl)amino $C_{2-8}$ alkenyl group, a $C_{1-8}$ alkoxyamino $C_{2-8}$ alkenyl group, a $C_{2-9}$ alkanoylamino $C_{2-8}$ alkenyl group, a $C_{6-12}$ arylamino $C_{2-8}$ alkenyl group, di($C_{6-12}$ aryl)amino $C_{2-8}$ alkenyl group, a $C_{1-8}$ alkyl($C_{6-12}$ aryl)amino $C_{2-8}$ alkenyl group, a 5 to 12-membered heteroarylamino $C_{2-8}$ alkenyl group, di(5 to 12-membered heteroaryl)amino $C_{2-8}$ alkenyl group, a $C_{1-8}$ alkyl(5 to 12-membered heteroaryl)amino $C_{2-8}$ alkenyl group, an amino $C_{2-8}$ alkynyl group, a $C_{1-8}$ alkylamino $C_{2-8}$ alkynyl group, di($C_{1-8}$ alkyl)amino $C_{2-8}$ alkynyl group, a $C_{1-8}$ alkoxyamino $C_{2-8}$ alkynyl group, a $C_{2-9}$ alkanoylamino $C_{2-8}$ alkynyl group, a $C_{6-12}$ arylamino $C_{2-8}$ alkynyl group, di($C_{6-12}$ aryl)amino $C_{2-8}$ alkynyl group, a $C_{1-8}$ alkyl($C_{6-12}$ aryl)amino $C_{2-8}$ alkynyl group, a 5 to 12-membered heteroarylamino $C_{2-8}$ alkynyl group, di(5 to 12-membered heteroaryl)amino $C_{2-8}$ alkynyl group or a $C_{1-8}$ alkyl(5 to 12-membered heteroaryl)amino $C_{2-8}$ alkynyl group, which may be respectively protected if necessary and may be substituted by at least one $Z^4$ which have the same meaning as $Z^3$, and $R^4$ may form, together with $R^3$, 5, 6 or 7-membered heterocyclic group of monocycle or bicycle, which may further contains 0 to 4 hetero atoms selected from N, O, S(O)$_n$ (wherein, n represents 0, 1 or 2); provided that the case $R^3$ is hydrogen atom or hydroxy group when Y is oxygen atom or sulfur atom is excluded), and the compound represented by the formula (III):

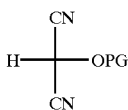

(III)

(wherein, PG represents:
  a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
  b) a $C_{2-9}$ alkanoyl group;
  c) a $C_{3-9}$ alkenoyl group;
  d) a $C_{3-9}$ alkynoyl group;
  e) a $C_{7-13}$ aryloyl group;
  f) a 5 to 12-membered heteroaryloyl group;
  g) a $C_{6-12}$ aryl $C_{2-9}$ alkanoyl group;
  h) a 5 to 12-membered heteroaryl $C_{2-9}$ alkanoyl group;
  i) a $C_{1-8}$ alkyl $C_{6-12}$ aryl $C_{2-9}$ alkanoyl group;
  j) a $C_{1-8}$ alkylsulfonyl group;
  k) a $C_{1-8}$ alkylsulfinyl group;
  l) a $C_{6-12}$ arylsulfonyl group;
  m) a $C_{6-12}$ arylsulfinyl group;
  n) a 5 to 12-membered heteroarylsulfonyl group;
  o) a 5 to 12-membered heteroarylsulfinyl group;
  p) a $C_{6-12}$ aryl $C_{1-8}$ alkylsulfonyl group;
  g) a $C_{6-12}$ aryl $C_{1-8}$ alkylsulfinyl group;
  r) a 5 to 12-membered heteroaryl $C_{1-8}$ alkylsulfonyl group;
  s) a 5 to 12-membered heteroaryl $C_{1-8}$ alkylsulfinyl group;
  t) a $C_{1-8}$ alkyl $C_{6-12}$ arylsulfonyl group;
  u) a $C_{1-8}$ alkyl $C_{6-12}$ arylsulfinyl group;
  v) a $C_{1-8}$ alkyl 5 to 12-membered heteroarylsulfonyl group;
  w) a $C_{1-8}$ alkyl 5 to 12-membered heteroarylsulfinyl group;
  x) a $C_{1-6}$ alkylphosphonyl group;
  y) a $C_{6-12}$ arylphosphonyl group or
  z) a 5 to 12-membered heteroarylphosphonyl group) by one-pot under the condition of, if necessary, activating the compound represented by the above formula (III); and deprotecting, if necessary.

4. A process for producing an α-hydroxy-carbonyl compound or an α-protected hydroxy-carbonyl compound represented by the formula (IV) or (IV'):

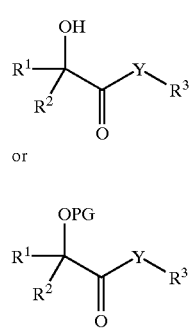

(IV)

or (IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

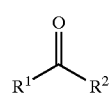

(I)

wherein, $R^1$ and $R^2$ are the same as or different from each other and each represents hydrogen atom, a $C_{1-8}$ alkyl group, a $C_{3-8}$ cycloalkyl group, a $C_{2-8}$ alkenyl group, a $C_{6-12}$ aryl group, a $C_{1-8}$ alkyl $C_{6-12}$ aryl group, a $C_{2-8}$ alkenylaryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group, a $C_{1-8}$ alkyl $C_{6-12}$ aryl $C_{1-8}$ alkyl group or a 5 to 12-membered heteroaryl group, which may be respecteively protected if necessary, and are independent of each other and may be substituted by at least one optional group selected from the group represented by $Z^1$ (wherein, $Z^1$ has the same meaning as $Z^3$), provided that the compound in which both $R^1$ and $R^2$ are hydrogen atoms is excluded;

$$R^3-YH \qquad (II)$$

wherein, $R^3$ represents hydrogen atom, a hydroxy group, a $C_{1-8}$ alkyl group, a $C_{3-8}$ cycloalkyl group, a $C_{2-8}$ alkenyl group, a $C_{6-12}$ aryl group, a $C_{1-8}$ alkyl $C_{6-12}$ aryl group, a $C_{2-8}$ alkenylaryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group, a $C_{1-8}$ alkyl $C_{6-12}$ aryl $C_{1-8}$ alkyl group, a 5 to 12-membered heteroaryl group, an amino group or a $C_{1-6}$ alkylamino group, which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N—$C_{1-8}$ alkylcarbamoyl group, an N,N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl)amino group, a 5 to 12-membered heteroarylamino group, di(5 to 12-membered heteroaryl)amino group or a $C_{1-8}$ alkyl(5 to 12-membered heteroaryl)amino group, which may be respectively protected if necessary); Y represents oxygen atom, sulfur atom or the formula $R^4$N (wherein $R^4$ represents hydrogen atom, a hydroxy group, a $C_{1-8}$ alkyl group, a $C_{3-8}$ cycloalkyl group, a $C_{1-8}$ hydroxyalkyl group, a $C_{1-8}$ alkoxycarbonyl $C_{1-8}$ alkyl group, a $C_{2-8}$ alkenyl group, a $C_{6-12}$ aryl group, a $C_{1-8}$ alkyl $C_{6-12}$ aryl group, a $C_{2-8}$ alkenyl $C_{6-12}$ aryl group, a hydroxy $C_{6-12}$ aryl group, a halogeno $C_{6-12}$ aryl group, a nitro $C_{6-12}$ aryl group, a cyano $C_{6-12}$ aryl group, a $C_{6-12}$ aryl $C_{1-8}$ alkyl group, a $C_{6-12}$ aryl $C_{2-8}$ alkenyl group or a $C_{1-8}$ alkyl $C_{6-12}$ aryl $C_{1-8}$ alkyl group, which may be respectively protected if necessary and may be substituted by at least one $Z^4$ which have the same meaning as $Z^3$, or, in case of $R^4$ forming together with $R^3$, 5, 6 or 7-membered heterocyclic group of monocycle or bicycle, which may further contains 0 to 4 hetero atoms selected from N, O, S (O)$_n$ (wherein, n represents 0, 1 or 2)); provided that the case $R^3$ is hydrogen atom or hydroxy group when Y is oxygen atom or sulfur atom is excluded;

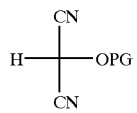

(III)

wherein, PG represents:
a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
b) a $C_{2-9}$ alkanoyl group;
c) a $C_{3-9}$ alkenoyl group;
d) a $C_{3-9}$ alkynoyl group;
e) a $C_{7-13}$ aryloyl group;
f) a 5 to 12-membered heteroaryloyl group;
g) a $C_{6-12}$ aryl $C_{2-9}$ alkanoyl group;
h) a 5 to 12-membered heteroaryl $C_{2-9}$ alkanoyl group;
i) a $C_{1-8}$ alkyl $C_{6-12}$ aryl $C_{2-9}$ alkanoyl group;
j) a $C_{1-8}$ alkylsulfonyl group;
k) a $C_{1-8}$ alkylsulfinyl group;
l) a $C_{6-12}$ arylsulfonyl group;
m) a $C_{6-12}$ arylsulfinyl group;
n) a 5 to 12-membered heteroarylsulfonyl group;
o) a 5 to 12-membered heteroarylsulfinyl group;
p) a $C_{6-12}$ aryl $C_{1-8}$ alkylsulfonyl group;
q) a $C_{6-12}$ aryl $C_{1-8}$ alkylsulfinyl group;
r) a 5 to 12-membered heteroaryl $C_{1-8}$ alkylsulfonyl group;
s) a 5 to 12-membered heteroaryl $C_{1-8}$ alkylsulfinyl group;
t) a $C_{1-8}$ alkyl $C_{6-12}$ arylsulfonyl group;
u) a $C_{1-8}$ alkyl $C_{6-12}$ arylsulfinyl group;
v) a $C_{1-8}$ alkyl 5 to 12-membered heteroarylsulfonyl group;
w) a $C_{1-8}$ alkyl 5 to 12-membered heteroarylsulfinyl group;
x) a $C_{1-6}$ alkylphosphonyl group;
y) a $C_{6-12}$ arylphosphonyl group; or
z) a 5 to 12-membered heteroarylphosphonyl group.

5. A process for producing an α-hydroxy-carbonyl compound or an α-protected hydroxy-carbonyl compound represented by the formula (IV) or (IV'):

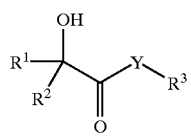

(IV)

or

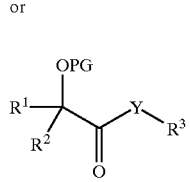

(IV')

(wherein, $R^1$, $R^2$, $R^3$, PG and Y respectively have the same meanings as defined below), which comprises the steps of reacting the compound represented by the formula (I), the compound represented by the formula (II) and the compound represented by the formula (III) by one-pot, if necessary, under the condition of activating the compound represented by the formula (III), and deprotecting, if necessary:

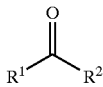
(I)

wherein, $R^1$ and $R^2$ are the same as or different from each other and each represents hydrogen atom, a $C_{1-8}$ alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respecteively protected if necessary, and are independent of each other and may be substituted by at least one optional group selected from the group represented by $Z^1$ (wherein, $Z^1$ has the same meaning as $Z^3$), provided that the compound in which both $R^1$ and $R^2$ are hydrogen atoms is excluded;

(II)

wherein, $R^3$ represents hydrogen atom, a hydroxy group, a $C_{1-8}$ alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respectively protected if necessary and may be substituted by at least one optional group selected from the group represented by $Z^3$ (wherein, $Z^3$ represents hydroxy group, mercapto group, amino group, hydroxyamino group, carboxyl group, thiocarboxyl group, dithiocarboxyl group, sulfonyl group, sulfonylamido group, azido group, cyano group, nitro group, ureido group, guanidino group, a $C_{1-8}$ alkylguanidino group, di$C_{1-8}$ alkylguanidino group, hydrazino group, hydrazinocarbonyl group, amidino group, a $C_{1-8}$ alkylamidino group, isocyano group, cyanate group, isocyanate group, thiocyanate group, isothiocyanate group, nitroso group, thioformyl group, a $C_{1-12}$ acyl group, a $C_{2-12}$ acyloxy group, a $C_{1-12}$ acyl $C_{1-8}$ alkyl group, carbamoyl group, a N—$C_{1-8}$ alkylcarbamoyl group, an N, N-di-($C_{1-8}$ alkyl)carbamoyl group, carbamyl group, a halogen atom, trifluoromethyl group, trifluoromethoxy group, morpholino group, thiomorpholino group, piperazino group, an N-alkylpiperazino group, piperidino group, pyrazolidino group, pyrrolinyl group, pyrrolidinyl group, imidazolidyl group, a $C_{1-8}$ alkylsulfonyl group, a $C_{1-8}$ alkylsulfinyl group, a $C_{6-12}$ arylsulfonyl group, a $C_{6-12}$ arylsulfinyl group, an amino group, a $C_{1-8}$ alkylamino group, di($C_{1-8}$ alkyl)amino group, a $C_{1-8}$ alkoxyamino group, a $C_{2-9}$ alkanoylamino group, a $C_{2-9}$ alkanoyloxyamino group, a $C_{6-12}$ arylamino group, di($C_{6-12}$ aryl)amino group, a $C_{1-8}$ alkyl($C_{6-12}$ aryl) amino group, a 5 to 12-membered heteroarylamino group, di(5 to 12-membered heteroaryl)amino group or a $C_{1-8}$ alkyl(5 to 12-membered heteroaryl)amino group, which may be respectively protected if necessary); Y represents oxygen atom or the formula $R^4N$ (wherein $R^4$ represents hydrogen atom, a hydroxy group, a $C_{1-8}$ alkyl group, a $C_{1-8}$ alkoxy group, a $C_{3-8}$ cycloalkyl group, a $C_{2-8}$ alkenyl group, a $C_{2-8}$ alkynyl group, a $C_{6-12}$ aryl group or a 5 to 12-membered heteroaryl group, which may be respectively protected if necessary and may be substituted by at least one $Z^4$ which have the same meaning as $Z^3$, or, in case of $R^4$ forming together with $R^3$, 5 or 6-membered heterocyclic group, which may further contains 0 to 4 hetero atoms selected from N, O, S(O)$_n$ (wherein, n represents 0, 1 or 2)); provided that the case $R^3$ is hydrogen atom or hydroxy group when Y is oxygen atom is excluded;

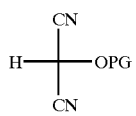
(III)

wherein, PG represents:
a) a silyl group which may be substituted by at least one selected from the group consisting of a $C_{1-8}$ alkyl group, a $C_{1-8}$ alkoxy group, a $C_{3-8}$ cycloalkyl group, an optionally substituted $C_{6-12}$ aryl group and an optionally substituted 5 to 12-membered heteroaryl group;
b) a $C_{2-9}$ alkanoyl group;
c) a $C_{3-9}$ alkenoyl group;
d) a $C_{3-9}$ alkynoyl group;
e) a $C_{7-13}$ aryloyl group;
f) a 5 to 12-membered heteroaryloyl group;
g) a $C_{6-12}$ aryl $C_{2-9}$ alkanoyl group;
h) a 5 to 12-membered heteroaryl $C_{2-9}$ alkanoyl group;
i) a $C_{1-8}$ alkyl $C_{6-12}$ aryl $C_{2-9}$ alkanoyl group;
j) a $C_{1-8}$ alkylsulfonyl group;
k) a $C_{1-8}$ alkylsulfinyl group;
l) a $C_{6-12}$ arylsulfonyl group;
m) a $C_{6-12}$ arylsulfinyl group;
n) a 5 to 12-membered heteroarylsulfonyl group;
o) a 5 to 12-membered heteroarylsulfinyl group;
p) a $C_{6-12}$ aryl $C_{1-8}$ alkylsulfonyl group;
q) a $C_{6-12}$ aryl $C_{1-8}$ alkylsulfinyl group;
r) a 5 to 12-membered heteroaryl $C_{1-8}$ alkylsulfonyl group;
s) a 5 to 12-membered heteroaryl $C_{1-8}$ alkylsulfinyl group;
t) a $C_{1-8}$ alkyl $C_{6-12}$ arylsulfonyl group;
u) a $C_{1-8}$ alkyl $C_{6-12}$ arylsulfinyl group;
v) a $C_{1-8}$ alkyl 5 to 12-membered heteroarylsulfonyl group;
w) a $C_{1-8}$ alkyl 5 to 12-membered heteroarylsulfinyl group;
x) a $C_{1-6}$ alkylphosphonyl group;
y) a $C_{6-12}$ arylphosphonyl group; or
z) a 5 to 12-membered heteroarylphosphonyl group.

6. The process for producing an α-hydroxy-carbonyl compound or an α-protected hydroxy-carbonyl compound as defined in claim 1, wherein the compound represented by the formula (III) is activated under the presence of bases, under the presence of a Pd complex or under an extra-high pressure.

7. The process for producing an α-hydroxy-carbonyl compound or an α-protected hydroxy-carbonyl compound as defined in claim 1, wherein the compound represented by the formula (III) is activated under the presence of bases.

8. The process for producing an α-hydroxy-carbonyl compound or an α-protected hydroxy-carbonyl compound as defined in claim 1, wherein the base is a tertiary amine or $K_2CO_3$.

9. The process for producing an α-hydroxy-carbonyl compound or an α-protected hydroxy-carbonyl compound as defined in claim 1, wherein the PG is a trimethylsilyl group, a t-butyldimethylsilyl group or a t-butyldiphenylsilyl group.

10. The process for producing an α-hydroxy-carbonyl compound or an α-protected hydroxy-carbonyl compound as defined in claim 1, wherein the PG is a $C_{2-9}$ alkanoyl group, a $C_{7-13}$ aryloyl group, a 5 to 12-membered group, a $C_{6-12}$ aryl $C_{2-9}$ alkanoyl group, a 5 to 12-membered heteroaryl $C_{2-9}$ alkanoyl group or a $C_{1-8}$ alkyl $C_{6-12}$ aryl $C_{2-9}$ alkanoyl group.

* * * * *